United States Patent [19]
Cunningham et al.

[11] Patent Number: 6,004,931
[45] Date of Patent: Dec. 21, 1999

[54] METHOD FOR INHIBITING GROWTH HORMONE ACTION

[75] Inventors: Brian C. Cunningham, San Bruno; James A. Wells, Burlingame; Ross G. Clark, Pacifica; Kenneth Olson, Burlingame; Germaine G. Fuh, Pacifica, all of Calif.

[73] Assignee: Genentech, Inc., South San Francisco, Calif.

[21] Appl. No.: 09/028,648

[22] Filed: Feb. 24, 1998

Related U.S. Application Data

[60] Division of application No. 08/717,394, Sep. 20, 1996, Pat. No. 5,849,535, which is a continuation-in-part of application No. 08/537,067, Sep. 21, 1995, abandoned, and a continuation-in-part of application No. 08/537,068, Sep. 21, 1995, abandoned, which is a continuation-in-part of application No. 08/067,160, May 25, 1993, abandoned.

[51] Int. Cl.$^6$ .............................. A61K 38/27; C07K 14/61
[52] U.S. Cl. ............................ 514/12; 514/866; 530/399; 530/402
[58] Field of Search ................................. 530/399, 402; 514/12, 866

[56] References Cited

U.S. PATENT DOCUMENTS

| | | |
|---|---|---|
| 3,853,832 | 12/1974 | Li . |
| 3,853,833 | 12/1974 | Li . |
| 4,446,235 | 5/1984 | Seeburg . |
| 4,665,160 | 5/1987 | Seeburg . |
| 4,670,393 | 6/1987 | Seeburg . |
| 4,699,897 | 10/1987 | Jones et al. . |
| 4,871,835 | 10/1989 | Aviv et al. . |
| 4,880,910 | 11/1989 | de Boer et al. . |
| 4,888,286 | 12/1989 | Crea . |
| 5,223,409 | 6/1993 | Ladner et al. . |
| 5,350,836 | 9/1994 | Kopchick et al. . |
| 5,534,617 | 7/1996 | Cunningham et al. . |

FOREIGN PATENT DOCUMENTS

| | | |
|---|---|---|
| 0 089 666A3 | 9/1993 | European Pat. Off. . |
| WO 88/07084 | 9/1988 | WIPO . |
| WO 88/07578 | 10/1988 | WIPO . |
| WO 90/02809 | 3/1990 | WIPO . |
| WO 90/04788 | 5/1990 | WIPO . |
| WO 90/05185 | 5/1990 | WIPO . |
| WO 90/08823 | 8/1990 | WIPO . |
| WO 92/01047 | 1/1992 | WIPO . |
| WO 92/09690 | 6/1992 | WIPO . |
| WO 92/19736 | 11/1992 | WIPO . |
| WO 92/21029 | 11/1992 | WIPO . |
| WO 93/00109 | 1/1993 | WIPO . |
| WO 95/08571 | 3/1995 | WIPO . |
| WO 96/40203 | 12/1996 | WIPO . |
| WO 96/40731 | 12/1996 | WIPO . |

OTHER PUBLICATIONS

S. Abdel–Meguid, et al. "Three–Dimensional Structure of a Genetically Engineered Variant of Procine Growth Hormone", Proc. Natl. Acad. Sci. USA, 84:6434–6437, 1987.

P. Argos, "An Investigation of Protein Subunit and Domain Interfaces", Protein Eng. 2:101–113, 1988.

J. Armstrong, et al. "Domain Structure of Bacteriophage fd Adsorption Protein", FEBS Letters, 135:167–172, 1981.

R. Aston and J. Ivanyi, "Monoclonal Antibodies to Growth Hormone and Prolactin", Parmac. Ther., 27:403–424, 1985.

M. Bajt, et al., "Characterization of a Gain of Function Mutation of Integrin $\alpha_{IIb}\beta3$ (Platelet Glycoprotein IIb–IIIa)", J. Biol. Chem., 267:22211–22216, 1992.

G. Barany and R. Merrifield, "Solid Phase Peptide Synthesis", 2:3–254, Gross & Meienhofer, eds., Academic Press, Inc. New York 1979.

D. Barlow, et al. "Continuous and Discontinuous Protein Antigenic Determinants", Nature, 322:747–748, 1986.

S. Bass, et al., "Hormone Phage: An Enrichment Method for Variant Proteins With Altered Binding Properties", Proteins: Struct. Funct., Genet., 8:309–314, 1990.

G. Baumann, et al., "A Specific Growth Hormone–Binding Protein in Human Plasma: Initial Characterization", Journal of Clinical Endocrinology and Metabolism, 62:134–141, 1986.

W. Bennett, et al., "High Resolution Analysis of Functional Determinants on Human Tissue–type Plasminogen Activator", J. Biol. Chem., 266:5191–5201, 1991.

A. Berendt, et al., "The Binding Site on ICAM–1 for Plasmodium Falciparum–Infected Erythrocytes Overlaps, but is Distinct From the LFA–1–Binding Site", Cell, 68:71–81, 1992.

C. Berlot and H. Bourne, "Identification of Effector–Activating Residues of $G_{s\alpha}$", Cell, 68:911–922, 1992.

B. Bettler, et al., "Immunoglobulin E–binding Site of $Fc_\epsilon$ Receptor ($Fc_\epsilon$RII/CD23) Identified by Homolog–Scanning Mutagenesis", J. Biol. Chem., 267:185–191, 1992.

J. Boutin, et al., "Cloning and Expression of the Rat Prolactin Receptor, a Member of the Growth Hormone/Prolactin Receptor Gene Family", Cell, 53:69–77, 1988.

J. Bowie, et al., "Deciphering the Message in Protein Sequences: Tolerance to Amino Acid Substitutions", Science, 247:1306–1310, 1990.

S. Burstein, et al., "Immunoreactivity and Receptor Binding of Mixed Recombinants of Human Growth Hormone and Chorionic Somatomammotropin", Proc. Natl. Acad. Sci. USA, 75:5391–5394, 1978.

R. Camble, et al., "Properties of Interferon–$\alpha_2$ Analogues Produced From Synthetic Genes", Peptides Structure and Function: Proceedings of the Ninth American Peptide Symposium, 375–384, (Deber, et al., eds., Pierce Chemical Co., Chicago, IL 1985).

(List continued on next page.)

*Primary Examiner*—John Ulm
*Assistant Examiner*—Christine Saoud
*Attorney, Agent, or Firm*—Merchant, Gould, Smith, Edell, Welter & Schmidt

[57] ABSTRACT

Human growth hormone variants are disclosed having enhanced affinity for the growth hormone receptor. Also disclosed are human growth hormone variants conjugated to one or more chemical groups, such as poly(ethylene glycol), which is believed to prolong the in vivo half-life of the variants.

12 Claims, 17 Drawing Sheets

OTHER PUBLICATIONS

P. Carter, et al., "Improved Oligonucleotide Site–directed Mutagenesis Using M13 Vectors", Nucl. Acids Res., 13:4431–4443, 1985.

C. Chang, et al., "High–Level Secretion of Human Growth Hormone by *Escherichia Coli*", Gene, 55:189–196, 1987.

R. Chawla, et al., "Structural Variants of Human Growth Hormone: Biochemical, Genetic, and Clinical Aspects", Ann. Rev. Med.. 34:519–547, 1983.

C. Chotia, "The Nature of the Accessible and Buried Surfaces in Proteins", J. Mol. Biol., 105:1–12, 1976.

L. Clayton, et al., "Substitution of Murine for Human CD4 Residues Identifies Amino Acids Critical for HIV–gp120 Binding", Nature, 335:363–366, 1988.

J. Crissman and G. Smith, "Gene–III Protein of Filamentous Phages: Evidence for a Carboxyl–Terminal Domain with a Role in Morphogenesis", Virology, 132:445–455, 1984.

B. Cunningham, et al., "Receptor and Antibody Epitopes in Human Growth Hormone Identified by Homolog–Scanning Mutagenesis", Science, 243:1330–1336, 1989.

B. Cunningham and J. Wells, "High–Resolution Epitope Mapping of hGH–Receptor Interaction by Alanine–Scanning Mutagenesis", Science, 244:1081–1085, 1989.

B. Cunningham, et al., "Engineering Human Prolactin to Bind to the Human Growth Hormone Receptor", Science, 247:1461–1465, 1990.

B. Cunningham, et al., "Dimerization of the Extracellular Domain of the Human Growth Hormone Receptor by a Single Hormone Molecule", Science, 254:821–825, 1991.

B. Cunningham and J. Wells, "Rational Design of Receptor-specific Variants of Human Growth Hormone", Proc. Natl. Acad. Sci. USA, 88:3407–3411, 1991.

S. Cwirla, et al., "Peptides on Phage: A Vast Library of Peptides for Identifying Ligands", Proc. Natl. Acad. Sci. USA, 87:6378–6382, 1990.

D. Davies and E. Paoland, "Antibody–Antigen Complexes", Ann. Rev. Biochem., 59:439–473, 1990.

V. de la Cruz, et al., "Immunogenicity and Epitope Mapping of Foreign Sequences via Genetically Engineered Filamentous Phage", J. Biol. Chem., 263:4318–4322, 1988.

A. de Vos, et al., "Human Growth Hormone and Extracellular Domain of Its Receptor Crystal Structure of the Complex", Science, 255:306–312, 1992.

J. Devlin, et al., "Random Peptide Libraries: A Source of Specific Protein Binding Molecules", Science, 249:404–406, 1990.

C. Edwards, et al., "A Newly Defined Property of Somatotropin: Proming of Macrophages for Production of Superoxide Anion", Science, 239:769–771, 1988.

G. Fuh, et al., "The Human Growth Hormone Receptor", J. Biol. Chem., 265–3111–3115, 1990.

G. Fuh, et al., "Rational Design of Potent Antagonists to the Human Growth Hormone Receptor", Science, 256:1677–1680, 1992.

A. Ge, et al., "Functional Domains of Bacillus Thuringiensis Insecticidal Crystal Proteins", J. Biol. Chem., 266:17954–17958, 1991.

H. Geysen, et al., "Use of Peptide Synthesis to Probe Viral Antigens for Epitopes to a Resolution of a Single Amino Acid", Proc. Natl. Acad. Sci. USA, 81:3998–4002, 1984.

H. Geysen, et al., "Antigen–Antibody Interactions at the Molecular Level: Adventures in Peptide Synthesis", Immun. Today, 6:364–369, 1985.

H. Geysen, et al., "A Priori Delineation of a Peptide Which Mimics a Discontinuous Antigenic Determinant", Mol. Immunology, 23:709–715, 1986.

D. Goeddel, et al., "Direct Expression in *Escherichia coli* of a DNA Sequence Coding for Human Growth Hormone", Nature, 281:544–548, 1979.

G. Gray, et al., "Periplasmic Production of Correctly Processed Human Growth in *Escherichia coli*: Natural and Bacterial Signal Sequences are Interchangeable", Gene, 39:247–254, 1985.

D. Güssow, et al., "Generating Biding Activities From *Escherichia coli* by Expression of a Repertoire of Immunoglobulin Variable Domains", Cold Spring Harbor Symposia on Quantitative Biology, LIV:265–272, 1989.

A. Herington, et al., "Identification and Characterization of Specific Binding Proteins for Growth Hormone in Normal Human Sera", J. Clin. Invest., 77:1817–1823, 1986.

J. Hughes, and H. Friesen, "The Nature and Regulation of the Receptors for Pituitary Growth Hormone", Ann. Rev. Physiol., 47:469–482, 1985.

O. Isaksson, et al., "Mode of Action of Pituitary Growth Hormone on Target Cells", Ann. Rev. Physiol., 47:483–499, 1985.

J. Janin, et al., "Surface, Subunit Interfaces and Interior of Oligomeric Proteins", J. Mol. Biol., 204:155–164, 1988.

P. Jones, et al., "Replacing the Complementarity–Determining Regions in a Human Antibody With Those From a Mouse", Nature, 321:522–525, 1986.

B. Kobilka, et al., "Chimeric α2–, β2–Adrenergic Receptors: Delineation of Domains Involved in Effector Coupling and Ligand Binding Specificity", Science, 240:1310–1316, 19088.

J. Kostyo, et al., "Biological Characterization of Purified Native 20–kDa Human Growth Hormone", Biochemica et Biophysica Acta, 925:314–324, 1987.

Krivi, et al., "Immunohistochemical Expression of Insulin–Like Growth Factor I During Skeletal Muscle Regeneration in Normal . . . ", Intl, Symp. on Growth Hormone, Abstract, 1–18 (Serono Symposia, USA 1987).

M. Laskowski, et al., "Positive Darwinian Selection in Evolution of Protein Inhibitors of Serine Proteinases", Cold Spring Harbor Symp. Quant. Biol., 52:545–553, 1987.

D. Leung, et al., "Growth Hormone Receptor and Serum Binding Protein: Purification, Cloning and Expression", Nature, 330:537–543, 1987.

U. Lewis, et al., "A Naturally Occurring Structural Variant of Human Growth Hormone", J. Biol. Chem., 253:2679–2687, 1978.

U. Lewis, et al., "Variants of Growth Hormone and Prolactin and Their Posttranslational Modifications", Ann. Rev. Physiol., 46:33–42, 1984.

C. Li, et al., "Human Pituitary Growth Hormone. XII. The Amino Acid Sequence of the Hormone", J. Am. Chem. Soc., 88:2050–2051, 1966.

C. Li, "Human Growth Hormone: 1974–1981", Mol. Cell. Biochem., 46:31–41, 1982.

H. Lowman and J. Wells, "Monovalent Phage Display: A Method for Selecting Variant Proteins From Random Libraries", Methods: Companion Methods Enzymol., 3:205–216, 1991.

H. Lowman, et al., "Selecting High–Affinity Binding Proteins by Monovalent Phage Display", Biochemistry, 30:10832–10838, 1991.

H. Lowman and J. Wells, "Selection of High–Affinity Variants of Human Growth Hormone by Monovalent Phage Display", Discussion of Mutations at American Society of Cell Biology Meeting, 1992.

M Mandel and A. Higa, "Calcium–dependent Bacteriophage DNA Infection", J. Mol. Biol., 53:159–162, 1970.

I. Marseigne, et al., "Synthesis and Biological Activity of $CCK_{26-33}$–Related Analogues Modified in Position 31", J. Med. Chem., 31:966–970, 1998.

J. Martal, et al., "Involvement of Lysine Residues in the Binding of hGH and bGH to Somatrotrpic Receptors", FEBS Lett., 180:295–299, 1985.

K. McFarland, et al., "Lutropin–Choriogonadotropin Receptor: An Unusual Member of the G Protein–Coupled Receptor Family", Science, 245:494–499, 1989.

S. Miller, "The Structure of Interfaces Between Subunits of Dimeric and Tetrameric Proteins", Protein Eng., 3:77–83, 1989.

J. Mills, et al., "Fragments of Human Growth Hormone Produced by Digestion With Thrombin: Chemistry and Biological Properties", Endocrinology, 107:391–399, 1980.

M. Nagashima, et al., "Alanine–Scanning Mutagenesis of the Epidermal Growth Factor–Like Domains of Human Thrombomodulin Identifies Critical Residues for its Cofactor Activity", J. Biol. Chem., 268:2888–2892, 1993.

C. Nicoll, et al., "Structural Features of Prolactins and Growth Hormones That Can be Related to Their Biological Properties", Endocrine Reviews, 7:169–203, 1986.

A. Paladini, et al., "Molecular Biology of Growth Hormone", CRC Crit. Rev. Biochem., 15:25–56, 1983.

S. Parmley and G. Smith, "Antibody–Selectable Filamentous fd Phage Vectors: Affinity Purification of Target Genes", Gene, 73:305–318, 1988.

C. Queen, et al., "A Humanized Antibody That Binds to the Interleukin 2 Receptor", Proc. Natl. Acad. Sci. USA 86:10029–10033, 1989.

I. Rasched and E. Oberer, "Ff Coliphages: Structural and Functional Relationships", Microbiological Reviews, 50:401–427, 1986.

B. Roberts, et al., "Directed Evolution of a Protein: Selection of Potent Neutrophil Elastase Inhibitors Displayed on M13 Fusion Phage", Proc. Natl. Acad. Sci. USA, 89:2429–2433, 1992.

J. Russell, et al., "Recombinant Hormones From Fragments of Human Growth Hormone and Human Placental Lactogen", J. Biol. Chem. 256:296–300, 1981.

W. Rutter, et al., "Redesigning Proteins Via Genetic Engineering", Protein Engineering, 257–267 (Oxender & Fox, eds., Alan R. Liss, Inc. New York 1987).

K. Sato, et al., "Synthesis and In Vitro Bioactivity of Human Growth Hormone–Releasing Factor Analogs Substituted With a Single D–Amino Acid", Biochem. and Biophys. Res. Comm., 149:531–537, 1987.

J. Scott, and G. Smith, "Searching for Peptide Ligands With an Epitope Library", Science, 249:386–390, 1990.

P. Seeburg, "The Human Growth Hormone Gene Family: Nucleotide Sequences Show Recent Divergence and Predict a New Polypeptide Hormone", DNA, 1:239–249, 1982.

D. Shortle, "Genetic Strategies for Analyzing Proteins", Protein Engineering, 103–108 (Oxender & Fox, eds., Alan R. Liss, Inc. New York 1987).

G. Smith, "Filamentous Fusion Phage: Novel Expression Vectors That Display Coned Antigens on the Virion Surface", Science, 228:1315–1317, 1985.

M. Thorner and M. Vance, "Growth Hormone, 1988", J. Clin. Invest., 82:745–747, 1988.

T. Tokunaga, et al., "Synthesis and Expression of Human Growth Hormone (Somatotropin) Gene Mutated to Change Cysteine–165 to Alanine", Eur. J. Biochem., 153:445–449, 1985.

M. Venuti, "The Impact of Biotechnology on Drug Discovery", Annual Reports in Medicinal Chemistry, 289–298 (Vinick, ed., Academic Press, Inc. 1989).

J. Wells, et al., "Cassette Mutagenesis: An Efficient Method for Generation of Multiple Mutations at Defined Sites", Gene, 34:315–323, 1985.

J. Wells, et al., "Importance of Hydrogen–Bond Formation in Stabilizing the Transition State of Subtilisin", Phil. Trans. R. Soc. Lond., A317:415–423, 1986.

J. Wells, "Additivity of Mutational Effects in Proteins", Biochem., 29:8509–8517, 1990.

J. Wells, "Systematic Mutational Analyses of Protein–Protein Interfaces", Methods in Enzymology, 202:390–411, 1991.

J. Wells, and A. deVos, "Structure and Function of Human Growth Hormone: Implications for the Hematopoietins", Ann. Rev. Biophys. Biomol. Struct., 22:329–351, 1993.

K. Wertman, et al., "Systematic Mutational Analysis of the Yeast ACT1 Gene", Genetics, 132:337–350, 1992.

R. Wharton, et al., "Substituting an α–Helix Switches the Sequence–Specific DNA Interactions of a Repressor", Cell, 38:361–369, 1984.

R. Wharton and M. Ptashne, "Changing the Binding Specificity of a Repressor by Redesigning an α–Helix", Nature, 316:601–605, 1985.

X. Zhang, et al., "Toward a Simplification of the Protein Folding Problem: A Stabilizing Polyalanine α–Helix Engineered in T4 Lysozyme", Biochemistry, 30:2012–2017, 1991.

M. Zoller and M. Smith, "Oligonucleotide–directed Mutagenesis Using M13–derived Vectors: An Efficient and General Procedure for the Production of Point Mutations in nay Fragment of DNA", Nucl. Acad. Res., 10:6487–6500, 1982.

M. Zoller, "New Molecular Biology Methods for Protein Engineering", Current Opinion in Structural Biology, 1:605–610, 1991.

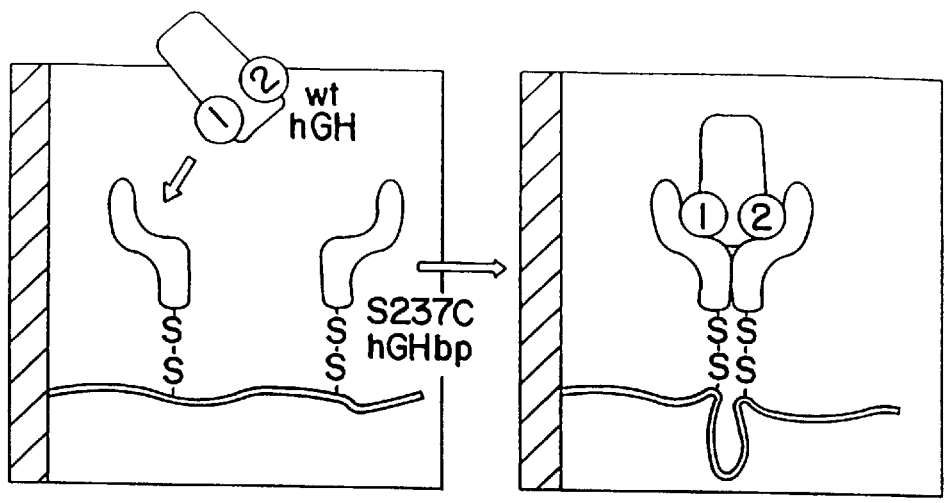
FIG. IA
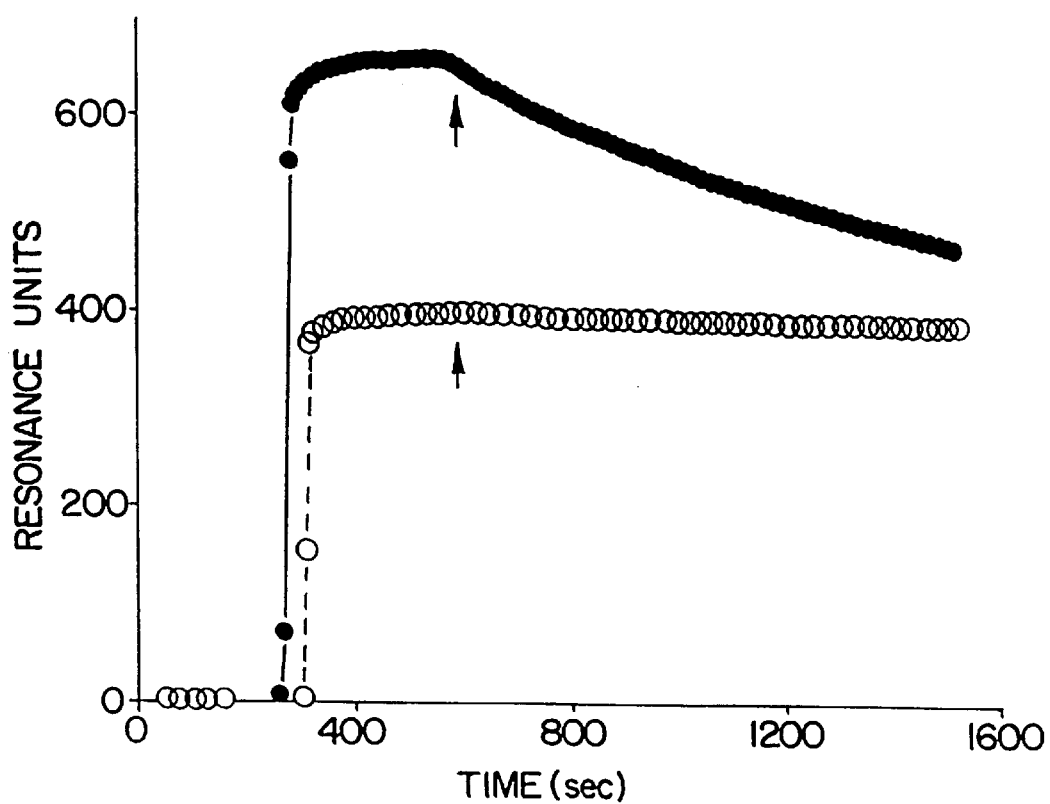
FIG. IB

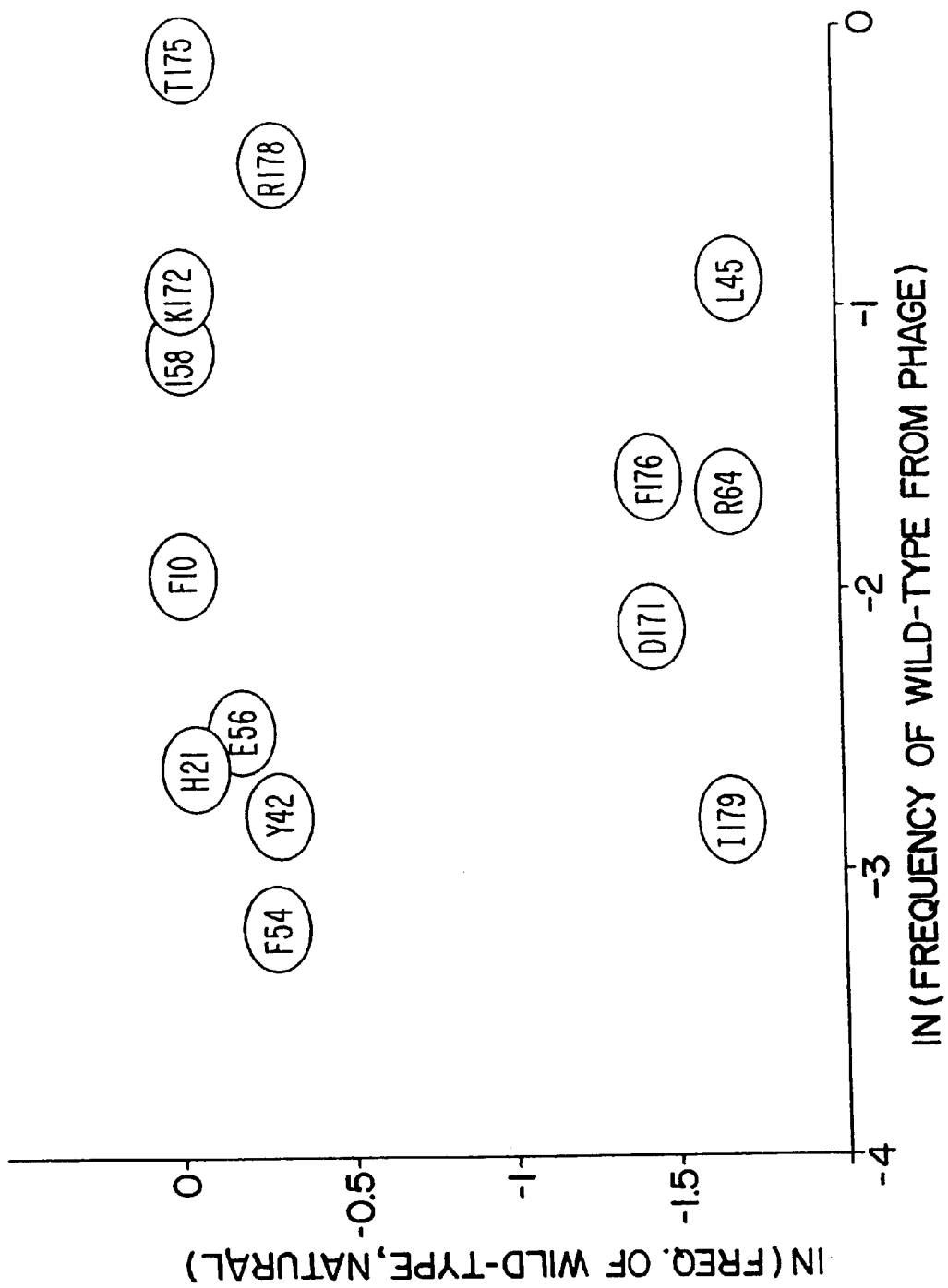

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 21 base pairs
      (B) TYPE: Nucleic Acid
      (C) STRANDEDNESS: Single
      (D) TOPOLOGY: Linear (xi) SEQUENCE DESCRIPTION: SEQ ID NO:1:

GCCACCTGAT GTCTAAGAAA C                                                  21

(2) INFORMATION FOR SEQ ID NO:2:

(i) SEQUENCE CHARACTERISTICS:
      (A) LENGTH: 33 base pairs
      (B) TYPE: Nucleic Acid
      (C) STRANDEDNESS: Single
      (D) TOPOLOGY: Linear (xi) SEQUENCE DESCRIPTION: SEQ ID NO:2:

TTTGAAGAGG CCTATATGGC CAAGGAACAG AAG                                     33

(2) INFORMATION FOR SEQ ID NO:3:

(i) SEQUENCE CHARACTERISTICS:
      (A) LENGTH: 29 base pairs
      (B) TYPE: Nucleic Acid
      (C) STRANDEDNESS: Single
      (D) TOPOLOGY: Linear (xi) SEQUENCE DESCRIPTION: SEQ ID NO:3:

CAGAACCCCC ATTGACGTCC CTCTGTTTC                                          29

(2) INFORMATION FOR SEQ ID NO:4:

(i) SEQUENCE CHARACTERISTICS:

(A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO:4:

TCCCGAAGGA GCAGNNSNNS TCGTTCNNSN NSAACCCGCA GACGT                45

(2) INFORMATION FOR SEQ ID NO:5:

(i) SEQUENCE CHARACTERISTICS:
        (A) LENGTH: 44 base pairs
        (B) TYPE: Nucleic Acid
        (C) STRANDEDNESS: Single
        (D) TOPOLOGY: Linear (xi) SEQUENCE DESCRIPTION: SEQ ID NO:5:

CTGCGGGTTS NNSNNGAACG ASNNSNNCTG CTCCTTCGGG ATAT                 44

(2) INFORMATION FOR SEQ ID NO:6:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO:6:

AACCCCCAGA CGTCCCTCTG T                                         21

(2) INFORMATION FOR SEQ ID NO:7:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:7:

GAAACACAAC AGTAAAGGTA ACCTAGAGCT GCT                            33

(2) INFORMATION FOR SEQ ID NO:8:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO:8:

CGTCTTCAAG AGTTCAACTT CTCC                                      24

(2) INFORMATION FOR SEQ ID NO:9:

(i) SEQUENCE CHARACTERISTICS:
        (A) LENGTH: 60 base pairs
        (B) TYPE: Nucleic Acid
        (C) STRANDEDNESS: Single
        (D) TOPOLOGY: Linear (xi) SEQUENCE DESCRIPTION: SEQ ID NO:9:

CCCTCTGTNN STCANNSTCT NNSCCGACAC CCAGTAATNN SGAGGAAACA          50

CAACAGAAGA                                                      60

(2) INFORMATION FOR SEQ ID NO:10:

(i) SEQUENCE CHARACTERISTICS:

```
            (A) LENGTH: 69 base pairs
            (B) TYPE: Nucleic Acid
            (C) STRANDEDNESS: Single
            (D) TOPOLOGY: Linear (xi) SEQUENCE DESCRIPTION: SEQ ID NO:10:

GTTACTCTTC TGTTGTGTTT CCTCSNNATT ACTGGGTGTC GGSNNAGASN              50

NTGASNNACA GAGGGACGT                                                69

(2) INFORMATION FOR SEQ ID NO:11:

(i) SEQUENCE CHARACTERISTICS:
            (A) LENGTH: 34 base pairs
            (B) TYPE: Nucleic Acid
            (C) STRANDEDNESS: Single
            (D) TOPOLOGY: Linear (xi) SEQUENCE DESCRIPTION: SEQ ID NO:11:

CTGCGTGCTC ACCGTCTTCA CCAGTTGGCC TTTG                               34

(2) INFORMATION FOR SEQ ID NO:12:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (xi) SEQUENCE DESCRIPTION: SEQ ID NO:12:

GTCAGCACAT TCCTGCGCAC C                                             21

(2) INFORMATION FOR SEQ ID NO:13:

(i) SEQUENCE CHARACTERISTICS:
            (A) LENGTH: 36 base pairs
            (B) TYPE: Nucleic Acid
            (C) STRANDEDNESS: Single
            (D) TOPOLOGY: Linear (xi) SEQUENCE DESCRIPTION: SEQ ID NO:13:

CTCTCGCGGC TCTTCGACAA CGCGATGCTG CGTGCT                             36

(2) INFORMATION FOR SEQ ID NO:14:

(i) SEQUENCE CHARACTERISTICS:
            (A) LENGTH: 33 base pairs
            (B) TYPE: Nucleic Acid
            (C) STRANDEDNESS: Single
            (D) TOPOLOGY: Linear (xi) SEQUENCE DESCRIPTION: SEQ ID NO:14:

TACTGCTTCA GGAAGGACAT GGACAAGGTC AGC                                33

(2) INFORMATION FOR SEQ ID NO:15:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:15:

CTGCGCATCG TGCAGTGC                                                 18

(2) INFORMATION FOR SEQ ID NO:16:

(i) SEQUENCE CHARACTERISTICS:
```

-continued (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO:16:

CTCTCGAGGC TCTTCGACAA CGCGTGG                                  27

(2) INFORMATION FOR SEQ ID NO:17:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:17:

CAGACCTCCC TCTGTCCCTC AGAGTCTATT CCG                           33

(2) INFORMATION FOR SEQ ID NO:18:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO:18:

ACACCCTCCA ACAAGGAGGA AACACAACAG                               30

(2) INFORMATION FOR SEQ ID NO:19:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO:19:

CCAAAGGAAC AGATTCATTC ATTCTGGTGG AACCCCCAGA CCTCC               45

METHOD FOR INHIBITING GROWTH HORMONE ACTION

This application is a divisional application of Ser. No. 08/717,394, filed Sep. 20, 1996, now U.S. Pat. No. 5,849,535, which is a continuation-in-part application of Ser. No. 08/537,067, filed Sep. 21, 1995 (now abandoned), and a continuation-in-part application of Ser. No. 08/537,068, filed Sep. 21, 1995 (now abandoned), both of which were continuation-in-part applications of Ser. No. 08/067,160, filed May 25, 1993 (now abandoned). The specification of the above-referenced applications.

BACKGROUND OF THE INVENTION

1. Field of the Invention

This invention relates to certain growth hormone variants, and pegylated forms thereof, for use as agonists or antagonists of human growth hormone.

2. Description of the Related Art

Human growth hormone (hGH) participates in much of the regulation of normal human growth and development. This 22,000-dalton pituitary hormone exhibits a multitude of biological effects, including linear growth (somatogenesis), lactation, activation of macrophages, and insulin-like and diabetogenic effects, among others. Chawla, *Annu. Rev. Med.*, 34: 519 (1983); Edwards et al., *Science*, 239: 769 (1988); Isaksson et al., *Annu. Rev. Physiol.*, 47: 483 (1985); Thorner and Vance, *J. Clin. Invest.*, 82: 745 (1988); Hughes and Friesen, *Annu. Rev. Physiol.*, 47: 469 (1985). These biological effects derive from the interaction between hGH and specific cellular receptors. Growth hormone deficiency in children leads to dwarfism, which has been successfully treated for more than a decade by exogenous administration of hGH. There is also interest in the antigenicity of hGH to distinguish among genetic and post-translationally modified forms of hGH (Lewis, *Ann. Rev. Physiol.*, 46: 33 [1984]), to characterize any immunological response to hGH when it is administered clinically, and to quantify circulating levels of the hormone.

hGH is a member of a family of homologous hormones that include placental lactogens, prolactins, and other genetic and species variants of growth hormone. Nichol et al., *Endocrine Reviews*, 7: 169 (1986). hGH is unusual among these in that it exhibits broad species specificity and binds to either the cloned somatogenic (Leung et al., *Nature*, 330: 537 [1987]) or prolactin (Boutin et al., *Cell*, 53: 69 [1988]) receptor. The cloned gene for hGH has been expressed in a secreted form in *E. coli* (Chang et al., *Gene*, 55: 189 [1987]) and its DNA and amino acid sequences have been reported. Goeddel et al., *Nature*, 281: 544 (1979); Gray et al., *Gene*, 39: 247 (1985). The three-dimensional folding pattern for porcine growth hormone (pGH) has been reported at moderate resolution and refinement. Abdel-Meguid et al., *Proc. Natl. Acad. Sci. USA*, 84: 6434 (1987). The receptor and antibody epitopes of hGH have been identified by homolog-scanning mutagenesis and alanine-scanning mutagenesis as described in the priority application to this application and in Cunningham et al., *Science*, 243: 1330–1336 (1989) and Cunningham and Wells, *Science*, 244: 1081–1085 (1989).

There are a large number of high-resolution structures that show the molecular details of protein—protein interfaces (for reviews, see Argos, *Protein Eng.*, 2: 101–113 [1988]; Janin et al., *J. Mol. Biol.*, 204: 155–164 [1988]; Miller, *Protein Eng.*, 3: 77–83 [1989]; Davies et al., *Annu. Rev. Biochem.*, 59: 439–473 [1990]). These define contact residues, but not the energetics for them nor do they show how docking occurs. A comprehensive understanding of the role of contact residues in affecting association and dissociation is fundamental to molecular recognition processes, and is practically important for the rational protein and drug design.

Perhaps the best characterized hormone-receptor complex is that between hGH and the extracellular domain of its receptor (hGHbp). For a review, see Wells and De Vos, *Annu. Rev. Biophys. Biomol. Struct.*, 22: 329–351 (1993). High-resolution structural and mutational analysis (Cunningham and Wells, supra; Cunningham et al., *Science*, 254: 821–825 [1991]) and structural analysis (De Vos et al., *Science*, 255: 306–312 [1992]) has shown that one molecule of hGH binds two receptor molecules sequentially using distinct sites on the hormone, called Sites 1 and 2.

A number of naturally occurring mutants of hGH have been identified. These include hGH-V [Seeberg, *DNA*, 1: 239 (1982); U.S. Pat. Nos. 4,446,235, 4,670,393, and 4,665,180] and 20K hGH containing a deletion of residues 32–46 of hGH. Kostyo et al., *Biochem. Biophys. Acta*, 925: 314 (1987); Lewis et al. *J. Biol. Chem.*, 253: 2679 (1978).

One investigator has reported the substitution of cysteine at position 165 in hGH with alanine to disrupt the disulfide bond which normally exists between Cys-53 and Cys-165. Tokunaga et al., *Eur. J. Biochem.*, 153: 445 (1985). This single substitution produced a mutant that apparently retained the tertiary structure of hGH and was recognized by receptors for hGH.

Another investigator has reported the in vitro synthesis of hGH on a solid resin support. The first report by this investigator disclosed an incorrect 188 amino acid sequence for hGH. Li et al., *J. Am. Chem. Soc.*, 88: 2050 (1966); U.S. Pat. No. 3,853,832. A second report disclosed a 190-amino acid sequence. U.S. Pat. No. 3,853,833. This latter sequence is also incorrect. In particular, hGH has an additional glutamine after position 68, a glutamic acid rather than glutamine at position 73, an aspartic acid rather than asparagine at position 106, and an asparagine rather than aspartic acid at position 108.

In addition to the foregoing, hybrid interferons have been reported that have altered binding to a particular monoclonal antibody. Camble et al., "Properties of Interferon-α2 Analogues Produced from Synthetic Genes" in *Peptides: Structure and Function. Proceedings of the Ninth American Peptide Symposium*, Deber et al., eds. (Pierce Chemical Co., Chicago, Ill., 1985), pp. 375–384. As disclosed therein, amino acid residues 101–114 from α-1 interferon or residues 98–114 from γ-interferon were substituted into α-2 interferon. α-2 interferon binds NK-2 monoclonal antibody, whereas α-1 interferon does not. This particular region in α-2 interferon apparently was chosen because 7 of the 27 amino acid differences between α-1 and α-2 interferon were located in this region. The hybrids so obtained reportedly had substantially reduced activity with NK-2 monoclonal antibody. When tested for antiviral activity, such hybrids demonstrated antiviral activity on a par with the activity of wild-type α-2 interferon. Substitutions of smaller sections within these regions were also reported. Sequential substitution of clusters of 3 to 7 alanine residues was also proposed. However, only one analog [Ala-30,32,33] IFN-α2 was disclosed.

Alanine substitution within a small peptide fragment of hen egg-while lysozyme and the effect of such substitutions on the stimulation of 2A11 or 3A9 cells has also been reported. Allen et al., *Nature*, 327: 713–715 (1987).

Others have reported that binding properties can be engineered by replacement of entire units of secondary structure including antigen binding loops (Jones et al., *Nature,* 321: 522–525 [1986]) or DNA recognition helices. Wharton et al., *Nature,* 316: 601–605 (1985).

The structure of amino-terminal methionyl bovine growth hormone (bGH) containing a spliced-in sequence of hGH including histidine 18 and histidine 21 has been shown. U.S. Pat. No. 4,880,910. Additional hGH variants are described in the priority applications for this application and in copending U.S. Ser. Nos. 07/715,300 filed Jun. 14, 1991 and 07/743,614 filed Aug. 9, 1991, and WO 92/09690 published Jun. 11, 1992. hGH variants are also disclosed (WO 93/00109 published Jan. 7, 1993) having the GH moiety covalently attached to poly(ethylene glycol) (PEG) at one or more amino acids, including those wherein the PEG molecule is attached to the lysine at position 41.

hGH variants are also reported in WO 92/21029 published Nov. 26, 1992, which discloses the 1:2 complex dimer between GH and two receptor molecules. The variant is a monomeric polypeptide ligand which comprises in its native conformation four amphipathic alpha helices and which binds to its receptor through two sites in sequential order. This variant comprises a mutation introduced into site 1 or site 2, provided that when the ligand is GH, at least two residues are mutated, one each in the N-terminal about 15 residues of the wild-type hormone and in helix C, or site 1 is mutated so as to increase the affinity of the ligand for its receptor at site 1.

It has previously been shown that monovalent phage display (Bass et al., *Proteins,* 8: 309–314 [1990]) can be used to improve the affinity of Site 1 in hGH for the hGHbp. Lowman et al., *Biochemistry,* 30: 10832–10838 (1991). Modest improvements in binding affinity (3 to 8-fold tighter than wild-type hGH) were produced by sorting three independent libraries each mutated at four different codons in Site 1. An hGH mutant slightly enhanced in binding affinity for Site 1 and blocked in its ability to bind Site 2 was a better antagonist of the hGH receptor than the Site 2 mutant alone. Fuh et al., *Science,* 256: 1677–1680 (1992). It would be desirable to improve Site 1 affinity further to obtain an even better antagonist that can have utility in treating conditions of GH excess such as acromegaly.

Additional improvements in Site 1 affinity might be obtained by mutating more residues per library. However, it was not feasible to generate enough transformants to ensure that all possible residue combinations were represented when more than about five codons were randomized simultaneously. Lowman and Wells, *Methods: Companion Methods Enzymol.,* 3: 205–216 (1991). Mutations at protein—protein interfaces usually exhibit additive effects upon binding. Wells, *Biochemistry,* 29: 8509–8517 (1990).

It is desired to obtain much larger improvements in affinity. It has been disclosed that the lysine residues of hGH and bGH are involved in the interaction of hGH and bGH with somatotropic receptors, with the structure-function relationship particularly implicating the lysine or arginine residues at positions 41, 64, 70, and 115. Martal et al., *FEBS Lett.,* 180: 295–299 (1985). Lysine residues were chemically modified by methylation, ethylation, guanidination, and acetimidination, resulting in reduced activity by radioreceptor assay.

The in vivo efficacy of hGH and hGH variants is determined, in part, by affinity for hGH receptor and by the rate of clearance from the circulation. The in vivo half-life of certain other therapeutic proteins has been increased by conjugating the proteins with PEG, which is termed "pegylation." See, e.g., Abuchowski et al., *J. Biol. Chem.,* 252:3582–3586 (1977). PEG is typically characterized as a non-immunogenic uncharged polymer with three water molecules per ethylene oxide monomer. PEG is believed to slow renal clearance by providing increased hydrodynamic volume in pegylated proteins. Maxfield et al., *Polymer,* 16:505–509 (1975). In one study, Katre and co-workers (Knauf, M. J. et al., *J. Biol. Chem.,* 363:15064–15070 [1988]; Goodson, R. J. & Katre, N. V., *Bio/Technology,* 8:343–346 [1990]) showed that the in vivo half-life of PEG-interleukin-2 increased with effective molecular weight. In addition, pegylation has been reported to reduce immunogenicity and toxicity of certain therapeutic proteins. Abuchowski et al., *J. Biol. Chem.,* 252:3578–3581 (1977).

SUMMARY OF THE INVENTION

The present invention provides a human growth hormone (hGH) variant including the following set of amino acid substitutions:

H18D, H21N, R167N, K168A, D171S, K172R, E174S, I179T.

Also provided is a human growth hormone variant including the following set of amino acid substitutions:

H18A, Q22A, F25A, D26A, Q29A, E65A, K168A, E174A.

These substitutions increase binding affinity for the hGH receptor at Site 1. An hGH variant including one of these sets of amino acid substitutions acts as an hGH agonist in the absence of an additional modification that disrupts binding to the hGH receptor at Site 2.

The substitution of a different amino acid at G120 is one modification that disrupts Site 2 binding. Accordingly, an hGH variant including an amino acid substitution at G120 acts as an hGH antagonist. The present invention provides hGH variants wherein a G120 amino acid substitution is combined with one of the sets of Site 1 amino acid substitutions. Thus, in one embodiment, an hGH variant includes the following set of amino acid substitutions:

H18D, H21N, G120K, R167N, K168A, D171S, K172R, E174S, I179T (hereinafter the "B2036 variant").

In another embodiment, an hGH variant includes the following set of amino acid substitutions:

H18A, Q22A, F25A, D26A, Q29A, E65A, G120K, K168A, E174A (hereinafter the "B2024 variant").

Further aspects of the invention include nucleic acid sequences, vectors, host cells, and processes for expression of these hGH variants.

The invention also includes hGH variants conjugated to one or more chemical groups that increase the molecular weight of the variant, as determined by mass spectrometry (hereinafter "actual molecular weight"), to at least about 40 kilodaltons. In one embodiment, an hGH variant is conjugated to one or more polyols, such as poly(ethylene glycol) (PEG). Also provided is a method of producing an hGH variant conjugated to PEG.

A further aspect of the invention is a method for inhibiting growth hormone action in a patient comprising administering to the patient an effective amount of an antagonist hGH variant of the invention.

BRIEF DESCRIPTION OF THE DRAWINGS

FIGS. 1A and 1B show the reaction (FIG. 1A) and kinetics (FIG. 1B) for binding of human growth hormone (hGH) or (G120R)hGH to the (S237C)hGHbp coupled to the BIAcore™ biosensor. The (S237C)hGHbp was immobilized on the thiol-dextran matrix (FIG. 1A) at a level of 1220 RU's, which corresponds to 1.2 ng/mm$^2$. In the binding-profile example (FIG. 1B), hGH (open symbols) or (G120R)hGH (filled symbols) was injected at saturating concentrations (>200 nM) to follow association and establish the limiting amount of bound hormone from which a stoichiometry was calculated. After saturation, the injector loop was switched to buffer to follow dissociation (indicated by the arrow).

FIG. 6A shows the hGH site-1 functional epitope. Residues involved in receptor binding, according to alanine-scanning mutagenesis, are shown on a cartoon model of hGH, derived from the hGH(hGHbp)$_2$ crystal structure. de Vos et al., supra. The effects of alanine substitutions (or Gln substitution in the case of K41) are shown based on BIAcore™ kinetics measurements, except for sites M14, H21, F54, E56, I58, S62, N63, and Y164. At these sites, BIAcore™ data were either not available or indicated a negligible effect on binding, and so the effect shown is based on RIA data. The change in binding free energy ($\Delta\Delta G$) was calculated as $-RT \ln[K_d(\text{Ala mutant})/K_d(\text{hGH})]$. Dark spheres show alanine substitutions that improved binding ($\Delta\Delta G=-1$ to $-0.5$ kcal/mol). The four white spheres of increasing size denote alanine substitutions that reduced binding energy by +0.5 to 1.0 kcal/mol, +1.0 to 1.5 kcal/mol, +1.5 to 2.0 kcal/mol, or +2.0 to 2.5 kcal/mol, respectively.

FIG. 6B is the hGH site-1 structural epitope. The four white spheres of increasing size represent a change in solvent-accessible area of −20 to 0 Å$^2$, 0 to 20 Å$^2$, 20 to 40 Å$^2$, or 40 to 60 Å$^2$, respectively, at each residue upon alanine substitution, as calculated from the hGH(hGHbp)$_2$ X-ray crystal structure.

FIG. 6C denotes the conservation of hGH residues in randomized phagemid libraries. Residues that were randomized, four positions at a time, in phage-displayed hGH libraries are shown: helix-1 [F10, M14, H18, H21]; minihelix-1 [K41, Y42, L45, Q46]; Loop-A [F54, E56, I58, R64]; helix-4A [K172, E174, F176, R178]; helix-4B [R167, D171, T175, I179]. The fraction of wild-type hGH residues found at each position after sorting for hGHbp binding [data reported herein and in Lowman et al., supra] is indicated by the size of black spheres: The smallest black sphere is 0–10% conserved, the next larger is 10–25% conserved, the next larger is 25–50% conserved, and the largest is >50% conserved.

FIGS. 8A, 8B, and 8C depict the relationship among the hGH structural epitope, phage-derived epitope, and evolutionary variants, respectively. The natural logarithm of the frequency with which the wild-type hGH residues appeared in hGH-phagemid pools (Lowman et al., supra) sorted for receptor binding is shown on the x-axis. Data from the Combinatorial libraries were not included. The log scale was chosen for comparison with buried surface areas. Residues M14, H18, K41, Q46, R167, and E174 do not appear on this graph, because no wild-type residues were found among any of the selected libraries.

FIG. 8A depicts a comparison with x-ray structure of hGH-(hGHbp)$_2$. The side-chain area of hGH residues buried by receptor-1 binding (solvent accessible area of: [free hGH]–[hGH-hGHbp complex] is plotted.

FIG. 8B depicts the results of phage display and alanine-scanning mutagenesis. The functional effect of Ala substitutions in hGH is plotted as in $[K_d (\text{Ala mutant})/K_d(\text{hGH})]$. Binding data were taken from BIAcore™ biosensor measurements, except where kinetics data were not available. For these non-contact residues (F10, F54, I58), values for $K_d$ obtained from radio-immunoprecipitation assays were used. Cunningham et al., 1989, supra.

FIG. 8C denotes conservation of residues among evolutionary variants. The amino acid sequences (Genbank, vol. 75, February 1993) of growth hormones from monkey, pig, elephant, hamster, whale, alpaca, fox, horse, sheep, rat, turtle, chicken, mink, cow, salmon, frog, and trout, as well as human placental lactogen, hGH(20K), and hGH-V were compared with that of wild-type hGH. Prolactin evolutionary variants were not included. The natural logarithm of the frequency with which the wild-type hGH residues appear among these variants is plotted.

DESCRIPTION OF THE PREFERRED EMBODIMENTS

Variants

Figure 2A:
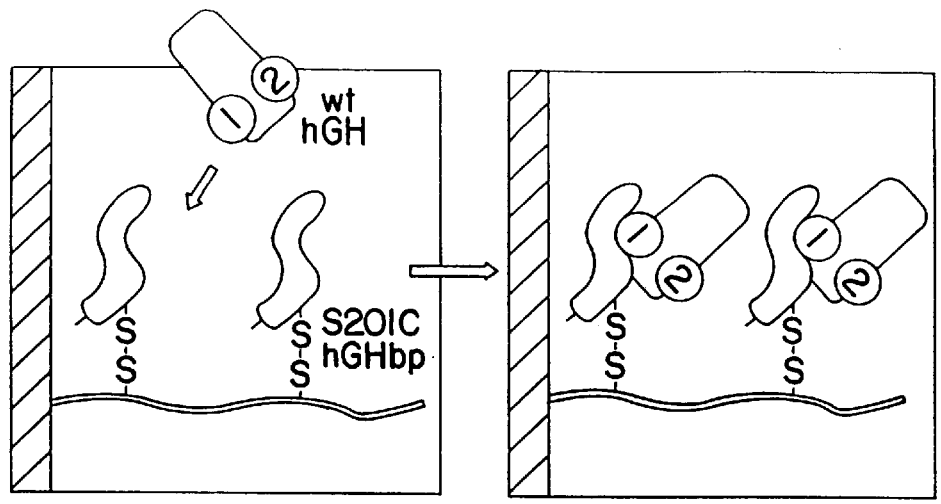
FIGS. 2A and 2B show the reaction (FIG. 2A) and kinetics (FIG. 2B) for binding of hGH (open symbols) or (G120R)hGH (closed symbols) to the (s201C)hGHbp coupled on the BIAcore™ biosensor. The (S201C)hGHbp was immobilized at a level of 1480 RU's (1.48 ng/mm$^2$) on the biosensor. Binding conditions and profiles are analogous to those in FIGS. 1A and 1B.

The DNA and amino acid sequences of human growth hormone (hGH) have been reported. Goeddel et al., supra; Gray et al., supra. The present invention describes novel hGH variants produced using either the alanine-scanning methodology or phagemid selection methods. The hGH variants of the present invention can be expressed in any recombinant system that is capable of expressing wild-type or met hGH.

Variant hGH sequence notation defines the actual amino acid substitutions in the hGH variants of the present invention. For a variant, substitutions are indicated by a letter representing the wild-type residue (in single-letter code), a number indicating the amino acid position in the wild-type sequence, and a second letter indicating the substituted amino acid residue. For example, R64K indicates a mutation in which Arg 64 is converted to Lys. Multiple mutants are indicated by a series of single mutants separated by commas.

Alanine-Scanning Mutagenesis

In one embodiment, the invention herein utilizes a systematic analysis of hGH to determine one or more active sites in the polypeptide that are involved in the interaction of the polypeptide with its receptor. Such analysis is conveniently performed using recombinant DNA technology. In general, the DNA sequence encoding hGH is cloned and manipulated so that it can be expressed in a convenient host. DNA encoding hGH can be obtained from a genomic library, from cDNA derived from mRNA in cells expressing the hGH, or by synthetically constructing the DNA sequence. Maniatis et al., *Molecular Cloning: A Laboratory Manual,* Cold Spring Harbor Laboratory, N.Y. (1982).

The wild-type hGH DNA is then inserted into an appropriate plasmid or vector that is used to transform a host cell. Prokaryotes are preferred for cloning and expressing DNA sequences to produce the hGH variants. For example, *E. coli* K12 strain 294 (ATCC No. 31446) can be used, as well as *E. coli* B, *E. coli* X1776 (ATCC No. 31537), and *E. coli* c600 and c600hfl, and *E. coli* W3110 (F$^-$, γ$^-$, prototrophic, ATCC No. 27325), bacilli such as *Bacillus subtilis,* and other enterobacteriaceae such as *Salmonella typhimurium* or *Serratia marcescens,* and various Pseudomonas species. The preferred prokaryote is *E. coli* W3110 (ATCC 27325). When expressed intracellularly in prokaryotes, the hGH typically contains an N-terminal methionine or a formyl methionine and is not glycosylated. When expressed extracellularly into the medium or the periplasm, the hGH does not contain an N-terminal methionine. These examples are, of course, intended to be illustrative rather than limiting.

In addition to prokaryotes, eukaryotic organisms, such as yeast cultures, or cells derived from multicellular organisms, can be used. In principle, any such cell culture is workable. However, interest has been greatest in vertebrate cells, and propagation of vertebrate cells in culture (tissue culture) has become a repeatable procedure. *Tissue Culture,* Academic Press, Kruse and Patterson, editors (1973). Examples of such useful host cell lines are VERO and HeLa, Chinese hamster ovary (CHO), W138, BHK, COS-7, and MDCK cell lines.

In general, plasmid vectors containing replication and control sequences that are derived from species compatible with the host cell are used in connection with these hosts. The vector ordinarily carries a replication site, as well as sequences that encode proteins that are capable of providing phenotypic selection in transformed cells. For example, *E. coli* can be transformed using pBR322, a plasmid derived from an *E. coli* species. Mandel et al., *J. Mol. Biol.,* 53: 154 (1970). Plasmid pBR322 contains genes for am picillin and tetracycline resistance and thus provides easy means for selection. One preferred vector is pBO475, described in Example 1 of a priority application to this application (U.S. Ser. No. 07/428,066 filed Oct. 26, 1989). This vector contains origins of replication for phage and *E. coli* that allow it to be shuttled between such hosts, thereby facilitating mutagenesis and expression. "Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector can be a plasmid, a phage particle, or simply a potential genomic insert. Once transformed into a suitable host, the vector can replicate and function independently of the host genome, or can, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

"Operably linked" when describing the relationship between two DNA or polypeptide regions simply means that they are functionally related to each other. For example, a presequence is operably linked to a peptide if it functions as a signal sequence, participating in the secretion of the mature form of the protein, most probably involving cleavage of the signal sequence. A promoter is operably linked to a coding sequence if it controls the transcription of the sequence; a ribosome binding site is operably linked to a coding sequence if it is positioned so as to permit translation.

Once the hGH is cloned, site-specific mutagenesis (Carter et al., *Nucl. Acids. Res.,* 13: 4331 [1986]; Zoller et al., *Nucl. Acids Res.,* 10: 6487 [1987]), cassette mutagenesis (Wells et al., *Gene,* 34, 315 [1985]), restriction selection mutagenesis (Wells et al., *Philos. Trans. R. Soc. London SerA,* 317: 415 [1986]), or other known techniques can be performed on the cloned hGH DNA to produce the variant DNA that encodes for the changes in amino acid sequence defined by the residues being substituted. When operably linked to an appropriate expression vector, active-domain-substituted hGH variants are obtained. In some cases, recovery of the hGH variant can be facilitated by expressing and secreting such molecules from the expression host by use of an appropriate signal sequence operably linked to the DNA sequence encoding the hGH parent or variant. Such methods are well known to those skilled in the art. Of course, other methods can be employed to produce such polypeptides such as the in vitro chemical synthesis of the desired hGH variant. Barany et al. in *The Peptides,* eds. E. Gross and J. Meienhofer (Academic Press: N.Y. 1979), Vol. 2, pp. 3–254.

Once the different GH variants are produced, they are contacted with the receptor and the interaction, if any, between the receptor and each variant is determined. These activities are compared to the activity of the wild-type hGH with the same receptor to determine which of the amino acid residues in the active domain are involved in the interaction with the receptor. The scanning amino acid used in such an analysis can be any different amino acid from that substituted, i.e., any of the 19 other naturally occurring amino acids.

The target receptor can be isolated from natural sources or prepared by recombinant methods by procedures known in the art. By way of illustration, the receptor can be prepared by the technique described by McFarland et al., *Science,* 245: 494–499 (1989).

The interaction between the receptor and parent and variant can be measured by any convenient in vitro or in vivo assay. Thus, in vitro assays can be used to determine any detectable interaction between a receptor and hGH. Such detection can include the measurement of calorimetric changes, changes in radioactivity, changes in solubility, changes in molecular weight as measured by gel electrophoresis, and/or gel exclusion methods, etc. In vivo assays include, but are not limited to, assays to detect physiological effects, e.g., weight gain or change in electrolyte balance. Generally, any in vivo assay can be used so long as a variable parameter exists so as to detect a change in the interaction between the receptor and the hGH of interest.

While any number of analytical measurements can be used to compare activities, a convenient one for binding of receptor is the dissociation constant $K_d$ of the complex formed between the hGH variant and receptor as compared to the $K_d$ for the wild-type hGH. Generally, a two-fold increase or decrease in $K_d$ per analogous residue substituted by the substitution indicates that the substituted residue(s) is active in the interaction of the wild-type hGH with the target.

When a suspected or known active amino acid residue is subjected to scanning amino acid analysis, the amino acid residues immediately adjacent thereto should be scanned. Three residue-substituted polypeptides can be made. One contains a scanning amino acid, preferably alanine, at position N which is the suspected or known active amino acid. The two others contain the scanning amino acid at position N+1 and N−1. If each substituted hGH causes a greater than about two-fold effect on $K_d$ for the receptor, the scanning amino acid is substituted at position N+2 and N−2. This is repeated until at least one, and preferably four, residues are identified in each direction which have less than about a two-fold effect on $K_d$ or either of the ends of the wild-type hGH are reached. In this manner, one or more amino acids along a continuous amino acid sequence which are involved in the interaction with the particular receptor can be identified.

The active amino acid residue identified by amino acid scan is typically one that contacts the receptor target directly. However, active amino acids can also indirectly contact the target through salt bridges formed with other residues or small molecules such as $H_2O$ or ionic species such as $Na^+$, $Ca^{-2}$, $Mg^{+2}$, or $Zn^{+2}$.

In some cases, the substitution of a scanning amino acid at one or more residues results in a residue-substituted polypeptide which is not expressed at levels which allow for the isolation of quantities sufficient to carry out analysis of its activity with the receptor. In such cases, a different scanning amino acid, preferably an isosteric amino acid, can be used.

Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions. Creighton, *The Proteins* (W. H. Freeman & Co., N.Y.); Chothia, *J. Mol. Biol.,* 150: 1 (1976). If alanine substitution does not yield adequate amounts of hGH variant, an isosteric amino acid can be used. Alternatively, the following amino acids in decreasing order of preference can be used: Ser, Asn, and Leu.

Once the active amino acid residues are identified, isosteric amino acids can be substituted. Such isosteric substitutions need not occur in all instances and can be performed before any active amino acid is identified. Such isosteric amino acid substitution is performed to minimize the potential disruptive effects on conformation that some substitutions can cause. Isosteric amino acids are shown in the table below:

| Polypeptide Amino Acid | Isosteric scanning Amino Acid |
| --- | --- |
| Ala (A) | Ser, Gly |
| Glu (E) | Gln, Asp |
| Gln (Q) | Asn, Glu |
| Asp (D) | Asn, Glu |
| Asn (N) | Ala, Asp |
| Leu (L) | Met, Ile |
| Gly (G) | Pro, Ala |
| Lys (K) | Met, Arg |
| Ser (S) | Thr, Ala |
| Val (V) | Ile, Thr |
| Arg (R) | Lys, Met, Asn |
| Thr (T) | Ser, Val |
| Pro (P) | Gly |
| Ile (I) | Met, Leu, Val |
| Met (M) | Ile, Leu |
| Phe (F) | Tyr |
| Tyr (Y) | Phe |
| Cys (C) | Ser, Ala |
| Trp (W) | Phe |
| His (H) | Asn, Gln |

The method herein can be used to detect active amino acid residues within different active domains. Once this identification is made, various modifications to the wild-type hGH can be made to modify the interaction between the parent hGH and one or more of the targets.

For hGH in particular, exemplary of the present invention is a preferred embodiment wherein the active domains and active residues which determine its activity with its somatogenic receptor (hGHbp) are identified. In carrying out this embodiment of the invention, hGH variants, including amino-acid-residue substituted hGH variants, have been made or identified which have different binding interactions with hGHbp as compared to naturally occurring hGH. Some can have a higher affinity for hGHbp and enhanced potency for somatogenesis in rats. Others have a decreased activity with hGHbp. Such hGH variants are useful as hGH agonists or antagonists and can have a higher potency for stimulating other receptors for hGH, if such variants are freed from substantial interaction with hGHbp. Further, such variants are useful in immunoassays for hGH as an hGH standard or tracer. Some variants can be identified which have a significant decrease in reactivity with human and mouse serum containing anti-hGH polyclonal antibodies. Others have the same binding affinity for hGHbp as hGH but increased potency to stimulate growth.

The method for determining the active domains and residues for hGH that interact with its somatogenic receptor from liver is shown schematically in FIG. 1, and the segments selected are shown in FIG. 2, of a priority application to this application (U.S. Ser. No. 07/428,066 filed Oct. 26, 1989).

Phagemid-Display Method

Additionally, the variants can be analyzed by phagemid display. This method involves (a) constructing a replicable expression vector comprising a first gene encoding the hGH, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a hGH receptor molecule (hGHbp) so that at least a portion of the phagemid particles bind to the receptor molecule; and (g) separating the phagemid particles that bind from those that do not. Preferably, the method further comprises transforming suitable host cells with recombinant phagemid particles that bind to the hGHbp and repeating steps (d) through (g) one or more times.

Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%.

Typically in this method, the expression vector further contains a secretory signal sequence fused to the DNA encoding each subunit of the polypeptide and the transcription regulatory element is a promoter system. Preferred promoter systems are selected from lac Z, $\lambda_{PL}$, tac, T7 polymerase, tryptophan, and alkaline phosphatase promoters and combinations thereof. Also, normally the method employs a helper phage selected from M13Ko7, M13R408, M13-VCS, and Phi X 174. The preferred helper phage is M13K07, and the preferred coat protein is the M13 Phage gene III coat protein. The preferred host is E. coli, and protease-deficient strains of E. coli. Novel hGH variants selected by the method of the present invention have been detected. Phagemid expression vectors were constructed that contain a suppressible termination codon functionally located between the nucleic acids encoding the polypeptide and the phage coat protein.

In detail, repeated cycles of hGH selection are used to select for higher and higher affinity binding by the phagemid selection of multiple amino acid changes which are selected by multiple selection cycles. Following a first round of phagemid selection, involving a first region or selection of amino acids in the ligand polypeptide, additional rounds of phagemid selection in other regions or amino acids of the ligand polypeptide are conducted. The cycles of phagemid selection are repeated until the desired affinity properties of the ligand polypeptide are achieved. To illustrate this process, phagemid selection of hGH was conducted in cycles. In the fist cycle hGH amino acids 172, 174, 176, and 178 can be mutated and phagemid selected. In a second cycle hGH amino acids 167, 171, 175, and 179 can be phagemid selected. In a third cycle hGH amino acids 10, 14, 18, and 21 can be phagemid selected. Optimum amino acid changes from a previous cycle can be incorporated into the polypeptide before the next cycle of selection. For example, hGH amino acids substitutions 174 (serine) and 176 (tyrosine) were incorporated into the hGH before the phagemid selection of hGH amino acids 167, 171, 175, and 179.

From the foregoing it will be appreciated that the amino acid residues that form the binding domain of the hGH are not sequentially linked and can reside on different subunits of the polypeptide. That is, the binding domain tracks with the particular secondary structure at the binding site and not the primary structure. Thus, generally, mutations are introduced into codons encoding amino acids within a particular secondary structure at sites directed away from the interior of the polypeptide so that they have the potential to interact with the receptor. The location of residues in hGH that strongly modulate its binding to the hGH receptor (Cunningham et al., Science, 1990, supra) are known. Hence, representative sites suitable for mutagenesis would include residues 172, 174, 176, and 178 on helix-4, as well as residue 64 located in a "non-ordered" secondary structure.

In this phagemid-display method, once the hGH gene has been isolated, it can be inserted into a suitable vector (preferably a plasmid) for amplification, as described generally by Sambrook et al., Molecular Biology: A Laboratory Manual, Cold Spring Harbor Press, Cold Spring Harbor, N.Y. 1989. While several types of vectors are available and can be used to practice this invention, plasmid vectors are the preferred vectors for use herein, as they can be constructed with relative ease, and can be readily amplified. Plasmid vectors generally contain a variety of components, including promoters, signal sequences, phenotypic selection genes, origin of replication sites, and other necessary components as are known to those of ordinary skill in the art.

Promoters most commonly used in prokaryotic vectors include the lac Z promoter system, the alkaline phosphatase pho A promoter, the bacteriophage $\lambda_{PL}$ promoter (a temperature-sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al., supra. While these are the most commonly used promoters, other suitable microbial promoters can be used as well.

Preferred promoters for practicing this invention for phagemid display are those that can be tightly regulated such that expression of the fusion gene can be controlled. It is believed that the problem that went unrecognized in the prior art was that display of multiple copies of the fusion protein on the surface of the phagemid particle lead to multipoint attachment of the phagemid with the target. This effect, referred to as the "chelate effect," is believed to result in selection of false "high affinity" polypeptides when multiple copies of the fusion protein are displayed on the phagemid particle in close proximity to one another so that the target was "chelated." When multipoint attachment occurs, the effective or apparent $K_d$ can be as high as the product of the individual $K_d$s for each copy of the displayed fusion protein.

It has been discovered that by tightly regulating expression of the fusion protein so that no more than a minor amount, i.e., fewer than about 1%, of the phagemid particles contain multiple copies of the fusion protein, the "chelate effect" is overcome, allowing proper selection of high-affinity polypeptides. Thus, depending on the promoter, culturing conditions of the host are adjusted to maximize the number of phagemid particles containing a single copy of the fusion protein and minimize the number of phagemid particles containing multiple copies of the fusion protein.

Preferred promoters used to practice this invention are the lac Z promoter and the pho A promoter. The lac Z promoter is regulated by the lac repressor protein lac i, and thus transcription of the fusion gene can be controlled by manipulation of the level of the lac repressor protein. By way of illustration, the phagemid containing the lac Z promoter is grown in a cell strain that contains a copy of the lac i repressor gene, a repressor for the lac Z promoter. Exemplary cell strains containing the lac i gene include JM 101 and XL1-blue. In the alternative, the host cell can be cotransfected with a plasmid containing both the repressor lac i and the lac Z promoter. Occasionally both of the above techniques are used simultaneously, that is, phagemid particles containing the lac Z promoter are grown in cell strains containing the lac i gene and the cell strains are cotransfected with a plasmid containing both the lac Z and lac i genes.

Normally when one wishes to express a gene, to the transfected host above one would add an inducer such as isopropylthiogalactoside (IPTG). In the present invention, however, this step is omitted to (a) minimize the expression of the gene III fusion protein, thereby minimizing the copy number (i.e., the number of gene III fusions per phagemid number) and to (b) prevent poor or improper packaging of the phagemid caused by inducers such as IPTG even at low concentrations. Typically, when no inducer is added, the number of fusion proteins per phagemid particle is about 0.1 (number of bulk fusion proteins/number of phagemid particles). The most preferred promoter used to practice this invention is pho A. This promoter is believed to be regulated by the level of inorganic phosphate in the cell where the phosphate acts to down-regulate the activity of the promoter. Thus, by depleting cells of phosphate, the activity of the promoter can be increased. The desired result is achieved by growing cells in a phosphate-enriched medium such as 2YT or LB, thereby controlling the expression of the gene III fusion.

One other useful component of vectors used to practice this invention is a signal sequence. This sequence is typically located immediately 5' to the gene encoding the fusion protein, and is thus transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence can be obtained as a restriction endonuclease fragment from any gene encoding a protein that has a signal sequence. Suitable prokaryotic signal sequences can be obtained from genes encoding, for example, lamB or ompF (Wong et al., *Gene,* 68: 193 [1983]), MalE, PhoA, and other genes. A preferred prokaryotic signal sequence for practicing this invention is the *E. coli* heat-stable enterotoxin II (STII) signal sequence as described by Chang et al., supra.

Another useful component of the vectors used to practice the phage-display method is phenotypic selection genes. Typical phenotypic selection genes are those encoding proteins that confer antibiotic resistance upon the host cell. By way of illustration, the ampicillin resistance gene (amp) and the tetracycline resistance gene (tet) are readily employed for this purpose.

Construction of suitable vectors comprising the aforementioned components as well as the gene encoding the hGH (gene 1) are prepared using standard recombinant DNA procedures as described in Sambrook et al., supra. Isolated DNA fragments to be combined to form the vector are cleaved, tailored, and ligated together in a specific order and orientation to generate the desired vector.

The DNA is cleaved using the appropriate restriction enzyme or enzymes in a suitable buffer. In general, about 0.2–1 $\mu$g of plasmid or DNA fragments is used with about 1–2 units of the appropriate restriction enzyme in about 20 $\mu$l of buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases, the ends are directly compatible after endonuclease digestion. However, it can be necessary to first convert the sticky ends commonly produced by endonuclease digestion to blunt ends to make them compatible for ligation. To blunt the ends, the DNA is treated in a suitable buffer for at least 15 minutes at 15° C. with 10 units of the Klenow fragment of DNA polymerase I (Klenow) in the presence of the four deoxynucleotide triphosphates. The DNA is then purified by phenol-chloroform extraction and ethanol precipitation.

The cleaved DNA fragments can be size-separated and selected using DNA gel electrophoresis. The DNA can be electrophoresed through either an agarose or a polyacrylamide matrix. The selection of the matrix depends on the size of the DNA fragments to be separated. After electrophoresis, the DNA is extracted form the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are put in solution in about equimolar amounts. The solution also contains ATP, ligase buffer, and a ligase such as T4 DNA ligase at about 10 units per 0.5 $\mu$g of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is transformed into a suitable host cell. Prokaryotes are the preferred host cells for this invention. Suitable prokaryotic host cells include *E. coli* strain JM101, *E. coli* K12 strain 294 (ATCC number 31,446), *E. coli* strain W3110 (ATCC number 27,325), *E. coli* X1776 (ATCC number 31,537), *E. coli* XL-1Blue (Stratagene), and *E. coli* B; however, many other strains of *E. coli,* such as HB101, NM522, NM538, and NM539, and many other species and genera of prokaryotes can be used as well. In addition to the *E. coli* strains listed above, bacilli such as *Bacillus subtilis,* other enterobacteriaceae such as *Salmonella typhimurium* or *Serratia marcescens,* and various Pseudomonas species can all be used as hosts.

Transformation of prokaryotic cells is readily accomplished using the calcium chloride method as described in section 1.82 of Sambrook et al., supra. Alternatively, electroporation (Neumann et al., *EMBO J.,* 1: 841 [1982]) can be used to transform these cells. The transformed cells are selected by growth on an antibiotic, commonly tet or amp, to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. Two suitable methods are the small-scale preparation of DNA and the large-scale preparation of DNA as described in sections 1.25–1.33 of Sambrook et al., supra. The isolated DNA can be purified by methods known in the art such as that described in section 1.40 of Sambrook et al., supra. This purified plasmid DNA is then analyzed by restriction mapping and/or DNA sequencing. DNA sequencing is generally performed by either the method of Messing et al., *Nucleic Acids Res.,* 9: 309 (1981), the method of Maxam et al., *Meth. Enzymol.,* 65: 499 (1980), or the method of Sanger et al., *Proc. Natl. Acad. Sci. USA,* 74: 5463–5467 (1977).

The phagemid-display method herein contemplates fusing the gene encoding the hGH (gene 1) to a second gene (gene 2) such that a fusion protein is generated during transcription. Gene 2 is typically a coat protein gene of a phage, and preferably it is the phage M13 gene III coat protein, or a fragment thereof. Fusion of genes 1 and 2 can be accomplished by inserting gene 2 into a particular site on a plasmid that contains gene 1, or by inserting gene 1 into a particular site on a plasmid that contains gene 2.

Insertion of a gene into a plasmid requires that the plasmid be cut at the precise location that the gene is to be inserted. Thus, there must be a restriction endonuclease site at this location (preferably a unique site such that the plasmid is only cut at a single location during restriction endonuclease digestion). The plasmid is digested, phosphatased, and purified as described above. The gene is then inserted into this linearized plasmid by ligating the two DNAs together. Ligation can be accomplished if the ends of the plasmid are compatible with the ends of the gene to be inserted. If the restriction enzymes are used to cut the plasmid and isolate the gene to be inserted to create blunt ends or compatible sticky ends, the DNAs can be ligated together directly with a ligase such as bacteriophage T4 DNA ligase by incubating the mixture at 16° C. for 1–4 hours in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the four deoxyribonucleotide triphosphates to fill in overhanging single-stranded ends of the digested DNA.

Alternatively, the ends can be blunted using a nuclease such as nuclease S1 or mung-bean nuclease, both of which function by cutting back the overhanging single strands of DNA. The DNA is then religated using a ligase as described above. In some cases, it may not be possible to blunt the ends of the gene to be inserted, as the reading frame of the coding region will be altered. To overcome this problem, oligonucleotide linkers can be used. The linkers serve as a bridge to connect the plasmid to the gene to be inserted. These linkers can be made synthetically as double-stranded or single-stranded DNA using standard methods. The linkers have one end that is compatible with the ends of the gene to be inserted; the linkers are first ligated to this gene using ligation methods described above. The other end of the linkers is designed to be compatible with the plasmid for ligation. In designing the linkers, care must be taken not to destroy the reading frame of the gene to be inserted or the reading frame of the gene contained on the plasmid. In some cases, it can be necessary to design the linkers such that they code for part of an amino acid, or such that they code for one or more amino acids.

Between gene 1 and gene 2, DNA encoding a termination codon can be inserted, such termination codons being UAG (amber), UAA (ocher), and UGA (opel). Davis et al., *Microbiology (Harper and Row: New York,* 1980), pages 237, 245–247, and 274. The termination codon expressed in a wild-type host cell results in the synthesis of the gene 1 protein product without the gene 2 protein attached. However, growth in a suppressor host cell results in the synthesis of detectable quantities of fused protein. Such suppressor host cells contain a tRNA modified to insert an amino acid in the termination codon position of the mRNA, thereby resulting in production of detectable amounts of the fusion protein. Such suppressor host cells are well known and described, such as *E. coli* suppressor strain. Bullock et al., *BioTechniques,* 5: 376–379 (1987). Any acceptable method can be used to place such a termination codon into the mRNA encoding the fusion polypeptide.

The suppressible codon can be inserted between the hGH gene and a second gene encoding at least a portion of a phage coat protein. Alternatively, the suppressible termination codon can be inserted adjacent to the fusion site by replacing the last amino acid triplet in the polypeptide or the first amino acid in the phage coat protein. When the phagemid containing the suppressible codon is grown in a suppressor host cell, it results in the detectable production of a fusion polypeptide containing the hGH and the coat protein. When the phagemid is grown in a non-suppressor host cell, the hGH is synthesized substantially without fusion to the phage coat protein due to termination at the inserted suppressible triplet encoding UAG, UAA, or UGA. In the non-suppressor cell the polypeptide is synthesized and secreted from the host cell due to the absence of the fused phage coat protein which otherwise anchored it to the host cell.

The hGH gene can be altered at one or more selected codons. An alteration is defined as a substitution, deletion, or insertion of one or more codons in the gene encoding the hGH that results in a change in the amino acid sequence of the hGH as compared with the unaltered or wild-type sequence of the hGH. Preferably, the alterations are by substitution of at least one amino acid with any other amino acid in one or more regions of the molecule. The alterations can be produced by a variety of methods known in the art. These methods include, but are not limited to, oligonucleotide-mediated mutagenesis and cassette mutagenesis.

Oligonucleotide-mediated mutagenesis is the preferred method for preparing substitution, deletion, or insertion variants of hGH. The technique is well known in the art as described by Zoller et al., supra. Briefly, the hGH gene is altered by hybridizing an oligonucleotide encoding the desired mutation to a DNA template, where the template is the single-stranded form of the plasmid containing the unaltered or wild-type DNA sequence for hGH. After hybridization, a DNA polymerase is used to synthesize an entire second complementary strand of the template, and thus incorporates the oligonucleotide primer and codes for the selected alteration in the hGH gene.

Generally, oligonucleotides of at least 25 nucleotides in length are used. Although smaller oligonucleotides can be employed, an optimal oligonucleotide has 12 to 15 nucleotides that are complementary to the template on either side of the nucleotide(s) coding for the mutation. This ensures that the oligonucleotide hybridizes properly to the single-stranded DNA template molecule. The oligonucleotides are readily synthesized using techniques known in the art such as that described by Crea et al., *Proc. Natl. Acad. Sci. USA,* 75: 5765 (1978).

The DNA template can only be generated by those vectors that are either derived from bacteriophage M13 vectors (the commercially available M13mp18 and M13mp19 vectors are suitable), or those vectors that contain a single-stranded phage origin of replication as described by Vieira and Messing, *Meth. Enzymol.,* 153: 3–11 (1987). Thus, the DNA that is to be mutated must be inserted into one of these vectors in order to generate single-stranded template. Production of the single-stranded template is described in sections 4.21–4.41 of Sambrook et al., supra.

To alter the wild-type DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the hGH gene, and the other strand (the original template) encodes the wild-type, unaltered sequence of the hGH gene. This heteroduplex molecule is then transformed into a suitable host cell, usually a prokaryote such as *E. coli* JM101. After the cells are grown, they are plated onto agarose plates and screened using the oligonucleotide primer radiolabeled with 32-Phosphate to identify the bacterial colonies that contain the mutated DNA.

The method described immediately above can be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA contains dCTP-(AS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted can be generated in one of several ways. If the amino acids are located close together in the polypeptide chain, they can be mutated simultaneously using one oligonucleotide that codes for all of the desired amino acid substitutions. If however, the amino acids are located some distance from each other (separated by more than about ten amino acids), it is more difficult to generate a single oligonucleotide that encodes all of the desired changes. Instead, one of two alternative methods can be employed.

In the first method, a separate oligonucleotide is generated for each amino acid to be substituted. The oligonucleotides are then annealed to the single-stranded template DNA simultaneously, and the second strand of DNA that is synthesized form the template encodes all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cassette mutagenesis is also a preferred method for preparing substitution, deletion, and insertion variants of hGH DNA. The method is based on that described by Wells et al., *Gene,* supra. The starting material is the plasmid (or other vector) comprising the hGH gene to be mutated. The codon(s) in the hGH gene to be mutated are identified. Optimally, there is a unique restriction endonuclease site on each side of the identified mutation site(s); however, this is not a requirement. If no such restriction sites exist, they can be generated using the above-described oligonucleotide-mediated mutagenesis method to introduce them at appropriate locations in the hGH gene. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of hGH.

For preparing the receptor molecule and binding it with the phagemid, the purified receptor is attached to a suitable matrix such as agarose beads, acrylamide beads, glass beads, cellulose, various acrylic copolymers, hydroxyalkyl methacrylate gels, polyacrylic acid, polymethacrylic copolymers, nylon, neutral and ionic carriers, and the like. Attachment of the receptor to the matrix can be accomplished by methods described in *Meth. Enzymol.*, 44: (1976), or by other means known in the art.

After attachment of the receptor to the matrix, the immobilized target is contacted with the library of phagemid particles under conditions suitable for binding of at least a portion of the phagemid particles with the immobilized target. Normally, the conditions, including pH, ionic strength, temperature, and the like mimic physiological conditions.

Bound phagemid particles ("binders") having high affinity for the immobilized receptor are separated from those having a low affinity (and thus do not bind to the target) by washing. Binders can be dissociated from the immobilized target by a variety of methods. These methods include competitive dissociation using the wild-type ligand, altering pH and/or ionic strength, and methods known in the art.

Suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected.

Optionally, the library of phagemid particles can be sequentially contacted with more than one immobilized receptor to improve selectivity for a particular receptor. Thus, hGH has more than one natural receptor: the GH receptor and the prolactin receptor. It may be desirable to improve the selectivity of hGH for the GH receptor over the prolactin receptor. This can be achieved by first contacting the library of phagemid particles with immobilized GH receptor, allowing binding to occur in the presence of a very high concentration of prolactin receptor in solution, and selecting for binders. In this case, an hGH mutant having a lower affinity for the prolactin receptor would have therapeutic utility even if the affinity for the GH receptor were somewhat lower than that of wild-type hGH.

Production of hGH Variants

The hGH variants of the present invention can be conveniently produced by standard recombinant techniques. More specifically, an hGH variant can be expressed using a vector-host cell system, such as described above in the discussion of alanine scanning.

In one embodiment, a phagemid of the present invention is used to produce an hGH variant free of the phage protein. For example, pSO643 and derivatives can simply be grown in a non-suppressor strain such as 16C9. In this case, the amber codon (TAG) leads to termination of translation, which yields free hormone. The hGH variant is secreted from the host cell and can be isolated from the culture medium as described below.

Host cells containing an hGH variant expression vector are cultured under conditions suitable for cell growth and for expression of the hGH variant. In particular, the culture medium contains appropriate nutrients and growth factors for the host cell employed. The nutrients and growth factors required for growth of a selected host cell are, in many instances, well known or can be readily determined empirically by those skilled in the art. Suitable culture conditions for mammalian host cells, for instance, are described in *Mammalian Cell Culture* (Mather, J. P. ed., Plenum Press 1984) and Barnes and Sato, *Cell,* 22:649 (1980).

In addition, the culture conditions should allow transcription, translation, and protein transport between cellular compartments. Factors that affect these processes are well-known and include, for example, DNA/RNA copy number; factors that stabilize RNA; nutrients, supplements, and transcriptional inducers or repressors present in the culture medium; temperature, pH, and osmolality of the culture; and cell density. The adjustment of these factors to promote expression in a particular vector-host cell system is within the level of skill in the art.

The cell culture procedure employed in the production of an hGH variant of the present invention can be any of a number of well-known procedures for large- or small-scale production of proteins. These include, but are not limited to, the use of: a fluidized bed bioreactor, a hollow fiber bioreactor, a roller bottle culture system, and a stirred tank bioreactor system. An hGH variant can be produced, for instance, in a batch, fed-batch, or continuous mode process.

Methods for recovery of recombinant proteins produced as described above are well-known and vary depending on the expression system employed. For example, if, as is typical, the expression vector contains a signal sequence, the hGH variant is recovered from the culture medium or the periplasm. Conveniently, the variant is secreted into the periplasmic space as a fully processed protein (i.e., lacking the secretion signal sequence). However, the hGH variant can also be expressed intracellularly and recovered from cell lysates.

The hGH variant can be purified from culture medium or a cell lysate by any method capable of separating the variant from components of the host cell or culture medium. Typically the hGH variant is separated from host cell and/or culture medium components that would interfere with pegylation, if desired, or with diagnostic or therapeutic use of the hGH variant.

As a first step, the culture medium or cell lysate is usually centrifuged or filtered to remove cellular debris. The supernatant is then typically concentrated or diluted to a desired volume or diafiltered into a suitable buffer to condition the preparation for further purification. Further purification of the hGH variant typically includes separating deamidated and clipped forms of the hGH variant from the intact form. For example, the intact hGH variant can be separated from the des-phe-hGH variant, which lacks the N-terminal phenylalanine.

In one variation of this embodiment, the hGH variant is purified (1) to a degree sufficient to obtain at least 15 residues of N-terminal or internal amino acid sequence, using a spinning cup sequenator, or (2) to homogeneity by SDS-PAGE under non-reducing or reducing conditions using Coomassie blue stain.

Any of the following exemplary procedures can be employed for purification of an hGH variant: affinity chromatography; anion- or cation-exchange chromatography (using, e.g., DEAE SEPHAROSE); chromatography on silica; reverse phase HPLC; gel filtration (using, e.g., SEPHADEX G-75); hydrophobic interaction chromatography; metal-chelate chromatography; ultrafiltration/diafiltration; ethanol precipitation; ammonium sulfate precipitation; chromatofocusing; and displacement chromatography. Exemplary protocols for purification of hGH variants (B2036 and B2024), using a combination of anion exchange chromatography and hydrophobic interaction chromatography, are set forth in Examples V and VI.

Modification of hGH Variants

The present invention provides hGH variants covalently attached (hereinafter "conjugated") to one or more chemical groups. Such conjugation produces an hGH variant conjugate having a greater actual molecular weight than the unmodified hGH variant. As used herein, the term "actual molecular weight" refers to the molecular weight, as measured by mass spectrometry (e.g., matrix-assisted laser desorption ionization mass spectrometry). The actual molecular weight of the hGH variant conjugate is usually at least about 30 kD; preferably, in the range of about 35 kD to about 55 kD; and more preferably, in the range of about 40 kD to about 50 kD. Generally, the actual molecular weight of the hGH variant conjugate does not exceed 100 kD.

Chemical groups suitable for use in an hGH variant conjugate of the present invention are preferably not significantly toxic or immunogenic, i.e., any toxicity or immunogenicity observed with an hGH variant conjugate is not significantly (i.e., less than 50%) greater than any toxicity or immunogenicity observed with the corresponding unmodified hGH variant. Typically, a chemical group is selected that reduces toxicity and/or immunogenicity associated with the unmodified hGH variant. In addition, the chemical group is conveniently selected to produce an hGH variant conjugate that can be stored and used under conditions suitable for storage and use of the unmodified hGH variant. Exemplary chemical groups include carbohydrates, such as, for example, those carbohydrates that occur naturally on glycoproteins, and non-proteinaceous polymers, such as polyols.

A polyol, for example, can be conjugated to an hGH variant molecule at one or more amino acid residues, including lysine residues, as disclosed in WO 93/00109, supra. The polyol employed can be any water-soluble poly(alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as poly(ethylene glycol) (PEG), and thus, for ease of description, the remainder of the discussion relates to an exemplary embodiment wherein the polyol employed is PEG and the process of conjugating the polyol to an hGH variant is termed "pegylation." However, those skilled in the art recognize that other polyols, such as, for example, poly(propylene glycol) and polyethylene-polypropylene glycol copolymers, can be employed using the techniques for conjugation described herein for PEG.

The average molecular weight of the PEG can range from about 500 to about 30,000 daltons (D); preferably, from about 1,000 to about 25,000 D; and more preferably, from about 4,000 to about 20,000 D. In one embodiment, pegylation is carried out with PEG having an average molecular weight of about 5,000 D (hereinafter "PEG(5000)"). As discussed below and in Example VII, the reaction conditions are adjusted to maximize production of hGH variant molecules conjugated to between about four and about six molecules of PEG(5000). In another embodiment, pegylation is carried out with PEG having an average molecular weight of about 20,000 D under conditions adjusted to maximize production of hGH molecules conjugated to one molecule of PEG(20,000). See Example VIII. In a variation of this embodiment, a branched-chain PEG having two chains of about 10,000 D each is employed. See Example IX.

PEG preparations that are commercially available, and suitable for use in the present invention, are nonhomogeneous preparations that are sold according to average molecular weight. For example, PEG(5000) preparations typically contain molecules that vary slightly in molecular weight, usually ±500 D.

A variety of methods for pegylating proteins have been described. See, e.g., U.S. Pat. No. 4,179,337 (issued to Davis et al.), disclosing the conjugation of a number of hormones and enzymes to PEG and polypropylene glycol to produce physiologically active non-immunogenic compositions. Generally, a PEG having at least one terminal hydroxy group is reacted with a coupling agent to form an activated PEG having a terminal reactive group. Id. This reactive group can then react with the α- and ε-amines of proteins to form a covalent bond. Conveniently, the other end of the PEG molecule can be "blocked" with a non-reactive chemical group, such as a methoxy group, to reduce the formation of PEG-crosslinked complexes of protein molecules.

For pegylation of an hGH variant, the activated PEG is one that can react with the variant under conditions that do not destroy Site 1 binding activity. For agonist hGH variants, Site 2 binding activity must also be preserved. Furthermore, for agonist and antagonist hGH variants, activated PEGs that introduce a toxic linking group into the conjugate are usually avoided.

Suitable activated PEGs can be produced by a number of conventional reactions. For example, an N-hydroxysuccinimide ester of a PEG (M-NHS-PEG) can be prepared from PEG-monomethyl ether (which is commercially available from Union Carbide) by reaction with N,N'-dicyclohexylcarbodiimide (DCC) and N-hydroxysuccinimide (NHS), according to the method of Buckmann and Merr, *Makromol. Chem.*, 182:1379–1384 (1981).

In addition, a PEG terminal hydroxy group can be converted to an amino group, for example, by reaction with thionyl bromide to form PEG-Br, followed by aminolysis with excess ammonia to form $PEG-NH_2$. The $PEG-NH_2$ is then conjugated to the protein of interest using standard coupling reagents, such as Woodward's Reagent K. Furthermore, a PEG terminal —$CH_2OH$ group can be converted to an aldehyde group, for example, by oxidation with $MnO_2$. The aldehyde group is conjugated to the protein by reductive alkylation with a reagent such as cyanoborohydride.

Alternatively, activated PEGs suitable for use in the present invention can be purchased from a number of vendors. For example, Shearwater Polymers, Inc. (Huntsville, Ala.) sells M-NHS-PEG as "SCM-PEG" in addition to a succinimidyl carbonate of methoxy-PEG ("SC-PEG") and methoxy-PEG succinimidyl propionate ("SPA-PEG"; hereinafter referred to as "M-SPA-PEG" to indicate the presence of the methoxy blocking group). The use of M-SPA-PEG to pegylate the B2036 variant is set forth in Examples VII and VIII. Shearwater Polymers also sells a branched-chain PEG having two 10,000 D chains (hereinafter "NHS-PEG2(20,000)," the use of which is described in Example IX.

The degree of pegylation of an hGH variant of the present invention can be adjusted to provide a desirably increased in vivo half-life (hereinafter "half-life"), compared to the corresponding non-pegylated protein. It is believed that the half-life of a pegylated hGH variant typically increases incrementally with increasing degree of pegylation. In studies of pegylated wild-type hGH, Applicants have observed that a wild-type hGH conjugate containing two PEG(5000) groups has about a 4-fold longer half-life in rats than the non-pegylated protein, a conjugate containing five PEG (5000) groups has about an 11-fold longer half-life, and a conjugate containing seven PEG groups has about an 18-fold longer half-life. The actual molecular weights of those PEG-wild-type hGH conjugates were approximately 33, 48, and 57 kD, respectively, as compared to 22 kD for the non-pegylated protein.

At higher degrees of pegylation, the increase in half-life of a pegylated hGH variant is believed to be partially offset by an increase in the dissociation constant ($K_d$) for Site 1 binding, indicating a decrease in Site 1 affinity. It is believed that this decrease in affinity is accompanied by a corresponding decrease in potency, which is reflected in an increase in the concentration of conjugate required for 50% maximal effect ($EC_{50}$). In studies of wild-type hGH pegylated with PEG(5000), a conjugate containing two PEG(5000) groups has about a 3-fold lower potency in a cell-based dimerization assay than the non-pegylated protein, a conjugate containing five PEG(5000) groups has about a 170-fold lower potency, and a conjugate containing seven PEG groups has about a 1500-fold lower potency.

Because Site 1 binding is essential for agonist and antagonist hGH variants of the present invention, increased pegylation reduces the potency of both types of hGH variants. However, the increase in half-life generally compensates for the reduction in potency, so that the in vivo efficacy of pegylated hGH variants is presently believed to be comparable to, or better than, that observed with the corresponding non-pegylated proteins. Accordingly, one skilled in the art can readily determine a suitable degree of pegylation for an hGH variant to produce a conjugate having a desirably increased half-life, compared to the non-pegylated protein, yet retaining sufficient potency to be efficacious in vivo.

Usually, the half-life is increased at least about five-fold; preferably, at least about 10-fold; more preferably, at least about 50-fold; and most preferably, at least about 100-fold. In addition, the degree and sites of pegylation are such that the PEG-hGH variant conjugate is capable of binding hGH receptor at Site 1, typically with a $K_d$ of about 400 nM or lower; preferably, with a $K_d$ of 150 nM or lower; and more preferably, with a $K_d$ of 100 nM or lower, as measured by an equilibrium binding assay, such as that described in Spencer et al., *J. Biol. Chem.*, 263:7862–7867 (1988).

Agonist PEG-hGH variant conjugates of the present invention are capable of binding at Site 2 as well as at Site 1, thus dimerizing hGH receptors. Dimerization capability can be measured, for example, by homoquenching of fluorescence, according to the method of Cunningham et al., *Science*, 254: 821–825 (1991), or in a cell-based dimerization assay, such as that described in Fuh et al., *Science*, 256:1677–1680 (1992), and in Examples XI and XII. Conveniently, the $EC_{50}$ for pegylated agonist hGH variants, as measured in the cell-based dimerization assay of Fuh et al., is about 100 nM or lower and more preferably, about 50 nM or lower. (The $EC_{50}$ is typically lower than the $K_d$, presumably because only a fraction of the available hGH receptors need to be dimerized to elicit a maximal response.) Pegylated hGH variants that meet these criteria have an actual molecular weight of at least about 40 kD. Exemplary conjugates include conjugates having about four to six, and preferably, five, molecules of PEG(5000) per molecule of hGH variant and conjugates having one molecule of PEG (20,000) per molecule of hGH variant.

The degree and sites of pegylation of a protein are determined by (1) the number and reactivities of pegylation sites (i.e., primary amines) and (2) pegylation reaction conditions. Wild-type hGH contains ten primary amines that are theoretically available to react with an activated PEG: the α-amino group of the N-terminal phenylalanine and the ε-amino groups of nine lysines. However, because some of the primary amines in hGH and the hGH variants are relatively unreactive, standard pegylation reactions typically result in less than complete pegylation (e.g., seven or eight PEGs per molecule for wild-type hGH).

The sites of pegylation of a protein are also somewhat constrained by the reactivities of the various primary amines. For example, a potential lysine in the Site 1 hormone-receptor binding interface of the B2036 variant (K41) is relatively unreactive with M-SPA-PEG(5000). See Example X. Thus, moderately pegylated B2036 variant preparations, having on the order of four to six PEGs per variant molecule, retain the ability to bind hGH receptor at Site 1, despite the presence of a potential pegylation site at this binding interface.

Standard mutagenesis techniques can be used to alter the number of lysines in the protein. Thus, to the extent that amino acid substitutions introduce or replace lysines, hGH variants of the present invention can contain a greater or lesser number of potential pegylation sites than wild-type hGH. The B2036 variant contains nine potential pegylation sites, one fewer than wild-type hGH, whereas the B2024 variant contains ten potential sites.

Furthermore, amino acid substitutions introducing or replacing lysines alter the locations of potential pegylation sites. For example, in the B2036 variant, the K168A and the K172R substitutions reduce the number of sites available for pegylation at the hormone-receptor Site 1 binding interface. The replacement of G120 with a different amino acid disrupts hGH binding at Site 2, converting the molecule to an hGH antagonist. The substitution of lysine for glycine at this position provides an additional potential pegylation site in Site 2, which is expected to impair any residual binding at this site. The reactivities of the primary amines in the B2036 variant are shown in Example X.

The degree and sites of pegylation can also be manipulated by adjusting reaction conditions, such as the relative concentrations of the activated PEG and the protein as well as the pH. Suitable conditions for a desired degree of pegylation can be determined empirically. Briefly, standard pegylation reactions are set up in which the above-noted parameters are varied. For example, hGH variant pegylation reactions (containing 10 mg/ml hGH variant in 0.05 M sodium borate buffer, pH 8.5) in which the number of equivalents of M-NHS-PEG(5000) per free amino group is varied between one and three produce the preparations shown below:

| Preparation | Molecules PEG(5000)/ Molecule hGH Variant |
| --- | --- |
| 1 | 2, 3, 4, 5 |
| 2 | 3, 4, 5, 6 |
| 3 | 4, 5, 6, 7 |

(As used with reference to the activated PEG, the phrase "equivalent per free amino group" refers to a molar amount of activated PEG equal to the molar amount of the molecule to be pegylated multiplied by the number of free amines in the molecule.) In preparations subjected to limited pegylation (such as preparation 1), the protein is pegylated at the most reactive sites, whereas, if pegylation is more extensive (as in preparation 3), less reactive sites are also pegylated.

Pegylation of hGH variants, such as B2036, is carried out by any convenient method. In an exemplary embodiment, hGH variants are pegylated with M-SPA-PEG(5000). See, Example VII. Briefly, solid SPA-PEG(5000) is added, with stirring, to an aqueous solution of hGH variant at room temperature. Typically, the aqueous solution is buffered with a buffer having a $pK_a$ near the pH at which the reaction is to be carried out (generally about pH 4–10). Examples of suitable buffers for pegylation at pH 7.5, for instance, include HEPES, phosphate, borate, Tris-HCl, EPPS, and TES. The pH is continuously monitored and adjusted if necessary. The reaction is allowed to continue for about one to about two hours.

The reaction products are then subjected to hydrophobic interaction chromatography to separate pegylated hGH variants from free M-SPA-PEG(5000) and any high-molecular weight complexes of the pegylated hGH variant. (High-molecular weight complexes arise when unblocked PEG is activated at both ends of the molecule, crosslinking hGH variant molecules.) The conditions during hydrophobic interaction chromatography are such that free M-SPA-PEG (5000) flows through the column, while any crosslinked pegylated hGH variant complexes elute after the desired forms, which contain one hGH variant molecule conjugated to one or more PEG groups. Suitable conditions vary depending on the relative sizes of the crosslinked complexes versus the desired conjugates and are readily determined by those skilled in the art. The eluent containing the desired conjugates is concentrated by ultrafiltration and desalted by diafiltration.

This preparation represents a heterogeneous mixture of PEG-hGH variant conjugates having between three and six PEG groups per molecule of hGH variant. In one embodiment, this mixture is subjected to an additional purification step that produces a more homogeneous preparation of pegylated hGH variants. More specifically, the mixture is subjected to cation exchange chromatography to fractionate the pegylated hGH variants according to the extent of pegylation. The conditions are such that the more highly pegylated hGH variants having a greater number of PEG groups elute early in the gradient.

In this manner, it is possible to obtain a pool of pegylated hGH variants containing primarily one or two forms. As used hereinafter, a "form" of a pegylated hGH variant is an PEG-hGH variant conjugate containing a particular number of PEG groups. Accordingly, different "forms" of a pegylated hGH variant have different numbers of PEG groups conjugated to the same hGH variant. In an exemplary embodiment, a pool of pegylated hGH variants is obtained that contains primarily two forms, namely, conjugates having 4 or 5 PEGs per molecule of hGH variant (hereinafter a "PEG-4/5-hGH variant preparation"). This pool can then be concentrated, desalted, and formulated for administration, as discussed below.

A composition containing a pegylated hGH variant for use in a therapeutic formulation can be heterogeneous or homogeneous, i.e., containing a single PEG-hGH form. Typically, the composition contains at least 70% one or two forms of PEG-hGH variant conjugates; preferably, at least 80% one or two forms; and more preferably, at least 90% one or two forms.

Therapeutic Formulations

Formulations of the hGH variants of the present invention for therapeutic administration are prepared for storage by mixing an hGH variant having the desired degree of purity with an optional pharmaceutically acceptable carrier, excipient, or stabilizer (*Remington's Pharmaceutical Sciences*, 16th edition, Oslo, A., Ed., [1980]) in the form of a lyophilized cake or an aqueous solution. Parenteral formulations can be prepared by mixing the hGH variant in a unit dosage injectable form (solution, suspension, or emulsion) with a pharmaceutically acceptable carrier. Pharmaceutically acceptable carriers, excipients, or stabilizers are non-toxic to recipients at the dosages and concentrations employed and are compatible with other ingredients of the formulation. For example, the formulation preferably does not include oxidizing agents and other compounds known to be deleterious to polypeptides.

Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counterions such as sodium; and/or nonionic surfactants such as Tween, Pluronics, or PEG.

Formulations of the present invention can additionally contain a pharmaceutically acceptable buffer, amino acid, bulking agent, and/or non-ionic surfactant. These include, for example, buffers, chelating agents, antioxidants, preservatives, cosolvents, and the like; specific examples of these could include trimethylamine salts (Tris buffer) and disodium edetate.

Additionally, the GH formulation set forth in WO 89/09614 can be employed, wherein the hGH variant is contained in a composition comprising glycine, mannitol and a buffer, such as a phosphate buffer. An exemplary version of this formulation is: 0.68 g/L glycine, 18.0 g/L mannitol, 5 mM sodium phosphate, pH 7.4. Alternatively, the hGH variant can be contained in a liquid formulation that does not necessarily contain mannitol or glycine and comprises 0.1 to 5% (w/v) of a non-ionic surfactant, such as polysorbate, or a poloxamer. An exemplary version of this formulation is: 5 mg/ml hGH variant, 8.77 mg/ml NaCl, 2.5 mg/ml phenol, 2.0 mg/ml polysorbate 20, and 10 mM sodium citrate, pH 6.0.

The hGH variant is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (U. Sidman et al., *Biopolymers*, 22, 547–556 [1983]), poly(2-hydroxyethyl methacrylate) (Langer et al., *J. Biomed. Mater. Res.*, 15: 167–277 [1981]; Langer, *Chem. Tech.*, 12: 98–105 [1982]), ethylene vinyl acetate (Langer et al., supra) or poly-D-(−)-3-hydroxybutyric acid (EP 133,988). Sustained-release hGH variant compositions also include liposomally entrapped hGH variants. Liposomes containing hGH variants are prepared by methods known per se: DE 3,218,121; Epstein et al., *Proc. Natl. Acad. Sci. U.S.A.*, 82: 3688–3692

(1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal hGH variant therapy.

The hGH variant can also be formulated for local administration. Suitable formulations vary depending on the site of administration and do not differ from those known in the art. For example, hGH can be formulated in a balanced salt solution for administration to the eye.

The hGH variant formulation for therapeutic administration is sterile. Sterility is readily accomplished by filtration through sterile filtration membranes (e.g., 0.2 micron membranes). Therapeutic hGH variant compositions generally are placed into a container having a sterile access port, for example, an intravenous solution bag or vial having a stopper pierceable by a hypodermic injection needle.

hGH variants ordinarily are stored in unit or multi-dose containers, for example, sealed ampoules or vials, as an aqueous solution or as a lyophilized formulation for reconstitution. As an example of a lyophilized formulation, 5-ml vials are filled with 2 ml of sterile-filtered 0.5% (w/v) aqueous hGH variant solution, and the resulting mixture is lyophilized. The infusion solution is prepared by reconstituting the lyophilized hGH variant using bacteriostatic water-for-injection and the like.

The formulation of pegylated hGH variants of the present invention is carried out as described above for hGH variants generally.

Therapeutic Uses

The present invention includes variants that act as agonists of hGH and variants that act as antagonists of hGH, the latter containing a Site 2-disruptive mutation. Agonist hGH variants are useful in increasing the anabolism or growth of a mammal. Growth refers to the dynamics of statural growth experienced by an individual during infancy, childhood, and adolescence as depicted by a normal growth curve. Thus, growth herein refers to the growth of linear-producing bone plate driven by chondrocytes, as distinguished from the growth of osteoblast cells, derived from a different part of the bone. Restoration of normal growth patterns would allow the patient to approach a more satisfactory growth curve. Examples of patients that are relatively resistant to GH but require treatment to induce an anabolic effect include those with Turner's Syndrome, GH-deficient children, children who experience a slowing or retardation in their normal growth curve about 2–3 years before their growth plate closes, that is, so-called short normal children, and patients where the insulin-like growth factor-I (IGF-I) response to GH has been blocked chemically (i.e., by glucocorticoid treatment) or by a natural condition such as in adult patients where the IGF-I response to GH is naturally reduced.

Immune disorders are also amenable to treatment with agonist hGH variants of the present invention. The expression "immune disorder" includes any condition in which the immune system of humans as well as animals has a smaller antibody response to antigens than normal, whether because their spleen size is smaller than it should be, whether the spleen is only partially functional, whether drugs such as chemotherapeutic agents are suppressing the normal immune function, whether the animal is functionally IGF-I- (or GH-) deficient, or due to any other factor. Examples include aged patients, patients undergoing chemotherapy or radiation therapy, recovering from a major illness, or about to undergo surgery, patients with AIDS, patients with congenital and acquired B-cell deficiencies such as hypogammaglobulinemia, common varied agammaglobulinemia, and selective immunoglobulin deficiencies, e.g., IgA deficiency, patients infected with a virus such as rabies with an incubation time shorter than the immune response of the patient, and patients with hereditary disorders such as diGeorge syndrome.

An agonist hGH variant can act to stimulate the immune system of a mammal by increasing its immune function, whether the increase is due to antibody mediation or cell mediation, and whether the immune system is endogenous to the host treated with the hGH variant or is transplanted from a donor to the host recipient given the hGH variant (as in bone marrow transplants). For example, the stimulation can result from an increased number of splenic cells such as splenic lymphocyte number, splenic T-cell population number (T-cell, $CD_4$ and $CD_8$), or splenic B-cell number, or from an increased number of thymocytes. Other cells involved in the immune system response include natural killer cells, macrophages, and neutrophils. In addition, the stimulation can be due to an increase in antibody production in response to an immunogen.

The agonist hGH variants of the present invention can also be used to stimulate heart function.

The antagonist hGH variants of the present invention, such as the B2036 and B2024 variants, are useful in treating conditions in which the inhibition of GH action is desirable. Particularly amenable to treatment with antagonist hGH variants are conditions in which a reduction of circulating levels of GH or of a mediator of GH action, such as IGF-I, provides a therapeutic benefit. Such conditions include conditions of GH excess such as, for example, giantism and acromegaly. Giantism results from GH excess before puberty, when the long bone growth is still possible.

Acromegaly results from GH excess after puberty, when the long bones have fused. Acromegaly is characterized by bony overgrowth and soft tissue swelling as well as hypertrophy of internal organs, especially the heart. Acromegaly is typically caused by a pituitary tumor that secretes GH. The hallmarks of the disease are high levels of circulating GH and IGF-I. The antagonist hGH variants of the present invention are presently believed to offer a significant therapeutic benefit by inhibiting GH action.

The antagonist hGH variants are also useful in treating the other conditions in which the inhibition of GH action provides therapeutic benefit. Examples include diabetes and its complications, such as for instance diabetic retinopathy and diabetic nephropathy. Diabetic retinopathy is characterized by proliferation of the cells making up the retinal blood vessels, growth of new vessels on top of the retina (neovascularization), development of microaneurysms, and leakage of fluid into the surrounding retinal tissue. The early hallmarks of diabetic nephropathy are renal hypertrophy and hyperfiltration. As the disease progresses, diffuse enlargement of the mesangial cells (which support the filtration apparatus of the kidney) is observed, accompanied by an absolute increase in the number of mesangial cells.

Vascular eye diseases that, like diabetic retinopathy, involve proliferative neovascularization are also believed to be amenable to treatment with antagonist hGH variants. Examples include retinopathy of prematurity, retinopathy associated with sickle cell anemia, and age-related macular degeneration, which is the most common cause of vision loss in persons over 55.

Other conditions in which the reduction of GH levels is presently believed to provide a therapeutic benefit include malignancies that respond to GH, or a mediator of GH action (such as IGF-1), by growing (hereinafter "GH-responsive malignancies"). Examples of GH-responsive malignancies include Wilm's tumor, various sarcomas (e.g., osteogenic sarcoma), and breast, colon, prostate, and thyroid cancer.

The antagonist hGH variants of the present invention inhibit the growth of cells expressing receptors to which the variants bind. A wide variety of tissues express such receptors. For example, GH receptor mRNA is expressed in cell lines from normal placenta, thymus, brain, salivary gland, prostate, bone marrow, skeletal muscle, trachea, spinal cord, retina, lymph node and from Burkitt's lymphoma, colorectal carcinoma, lung carcinoma, lymphoblastic leukemia, and melanoma. Thus, it is presently believed that antagonist hGH variants of the present invention are generally useful in treating cancers that express receptors to which the variants bind.

For the various purposes of this invention, the agonist or antagonist hGH variant is directly administered to the mammal by any suitable technique, including parenterally, and can be administered locally or systemically. The specific route of administration depends, e.g., on the medical history of the patient, including any perceived or anticipated side effects using the hGH variant. Examples of parenteral administration include subcutaneous, intramuscular, intravenous, intraarterial, and intraperitoneal administration.

The administration is by continuous infusion (using, e.g., minipumps such as osmotic pumps), or by injection using, e.g., intravenous or subcutaneous means. In one embodiment, the hGH variant is administered subcutaneously. The administration can also be as a single bolus or by slow-release depot formulation.

The hGH variant composition to be used in the therapy is formulated and dosed in a fashion consistent with good medical practice, taking into account the specific condition being treated, the clinical condition of the individual patient (especially the side effects of treatment with hGH variant alone), the site of delivery of the hGH variant composition, the method of administration, the scheduling of administration, and other factors known to practitioners. The "effective amount" of hGH variant for purposes herein (including an antagonist effective amount to counteract, e.g., acromegaly) is thus determined by such considerations.

As a general proposition, the total pharmaceutically effective amount of the hGH variant administered parenterally per dose is in the range of about 1 μg/kg/day to about 100 mg/kg/day of patient body weight, although, as noted above, this is subject to therapeutic discretion. Usually, this dose is between about 0.01 and about 10 mg/kg/day, and more usually for humans between about 0.01 and about 1 mg/kg/day. If given continuously, the hGH variant is typically administered at a dose rate of about 1 μg/kg/hour to about 50 μg/kg/hour, either by one to four injections per day or by continuous subcutaneous infusions, for example, using a mini-pump. An intravenous bag solution can also be employed. The key factor in selecting an appropriate dose is the result obtained, as measured for agonists, for example, by increases in long bone growth, antibody production, splenocyte or thymocyte number, and splenic B-cells, and as measured for antagonists, for example, by reduction in serum GH, serum IGF-I, and tumor growth, etc.

In general, a pegylated hGH variant of the present invention can be administered by any of the routes of administration described above. However, it is presently believed that a pegylated hGH variant need not be administered as frequently as a non-pegylated hGH variant. Non-pegylated hGH and hGH variants are typically administered at least three times a week and often daily. However, the pegylated forms of these proteins can be administered between about once every three days to about once a month, or more typically between about once every 6–7 days to once every two weeks.

The mammals potentially treatable by the hGH variants herein include mammals of economic importance such as bovine, ovine, and porcine animals. The preferred mammal herein is a human.

The following is presented by way of example and is not to be construed as a limitation to the scope of the invention. All citations used herein are expressly incorporated herein by reference.

EXAMPLE I

The kinetics and affinity of binding for alanine substitutions at 30 contact residues in Site 1 of hGH were evaluated. A biosensor device, called a BIAcore™ biosensor, was used that relies upon surface plasmon resonance to measure changes in refractive index upon hormone binding to an immobilized receptor. In this example it was found that affinity is dominated by less than one-quarter of the 31 contact side-chains, and these cluster in a small patch near the center of the contact epitope. Thus, the "structural epitope" is considerably larger than the "functional binding epitope."

Experimental Protocol

Alanine mutations of residues buried at Site 1 in hGH were available from the work described in Cunningham and Wells, supra, or newly made by site-directed mutagenesis. Kunkel et al., *Methods Enzymol.*, 154: 367–382 (1987). Variant proteins were produced and purified as described in Cunningham and Wells, supra. Yields were improved by extending the duration of the ammonium sulphate precipitations to one hour.

hGHbp (Wells and De Vos, supra) was immobilized on the Pharmacia BIAcore™ biosensor and changes in refractive index upon binding of hormone were used for kinetic measurements. The association and dissociation constants were calculated using software provided with the instrument. Karlsson et al., *J. Immunol. Methods*, 145: 229–240 (1991). The hGHbp was immobilized in discrete orientations on the sensor chip by fixing the hGHbp via a free thiol. This was accomplished by introducing a cysteine residue at one of two specific sites (S201C or S237C) using site-directed mutagenesis (Kunkel et al., supra). The thiol variants of the hGHbp were expressed in *E. coli* and purified to homogeneity. Fuh et al., *J. Biol. Chem.*, 265: 3111–3115 (1990). These proteins were coupled to the chip surface by activating the carboxyl-dextran matrix with N-ethyl-N'-(3-diethylaminopropyl)-carbodiimide (EDC) and reacting it with N-hydroxysuccinimide (NHS). The NHS-ester was reacted with 2-(2-pyridinyldithio)ethaneamine (PEDA). Remaining unreacted NHS-ester groups were displaced by addition of ethanolamine. The hGHbp variants were reacted with the matrix (at 50 μg/ml in 50 mM sodium acetate, pH 4.5) until approximately 1000 RU's were coupled (1.0 ng/mm$^2$; see the BIAcore™ manual).

Association rates were measured from binding profiles obtained by injecting increasing concentrations of each hGH variant. Five serial dilutions (each 2-fold) were made starting at 200 or 1000 nM hormone depending on the affinity for the hGHbp. A maximum flow rate of 20 µl/min. was applied to minimize potential mass transport effects. High salt buffer (150 mM NaCl, 10 mM sodium phosphate, pH 7.4) was used to prevent long-range electrostatic effects and to mimic physiological ionic strength. Also included was 0.02% Tween 20 to reduce non-specific binding. The matrix was regenerated by washing for 20 seconds with 4.5 M $MgCl_2$. Control experiments showed this was sufficient to remove all the bound hormone, and the matrix could be re-used more than 50 times without significant change in the binding kinetics.

Dissociation rates were measured by saturating the biosensor with 5 µM hGH mutant and switching to buffer without hormone. Buffer flow rates and regeneration conditions were identical to those used to measure the association profiles. Potential rebinding effects were minimized by using only the initial 10 minutes of each dissociation profile for calculation of the dissociation constant. Both association and dissociation constants were determined using the Pharmacia Kinetics Evaluation software to solve the rate equations. Karlsson et al., supra.

The average standard deviation within triplicate determinations of association constants on the same biosensor chip was ±4% of the value reported. Values determined between different biosensor chips vary up to 60%. However, because a wild-type reference was always included, the standard errors for the relative values reported here are the same as determinations made on the same chip. The concentration of hGH and variants was determined by densitometry of Coomassie blue-stained proteins after SDS polyacrylamide gel electrophoresis. This method confirms the purity and integrity of the variant hormones as well as providing a protein concentration independent of the substitution with a precision of ±10%. Cunningham and Wells, supra. Thus, the average cumulative errors in relative association, dissociation, and affinity constants are about 17%, 14%, and 21%, respectively.

Results

The binding of hGH to the hGHbp was studied by immobilizing a variant of the hGHbp, (S237C)hGHbp [Ser237 is converted to Cys in the hGHbp] to the thiol-derivatized matrix on the BIAcore™ biosensor via a mixed disulfide bond. FIG. 1A. The S237C(hGHbp) mutation does not affect binding affinity to hGH and has been used to attach a single thiol-specific fluorescent probe to follow hGH-induced dimerization of the hGHbp in solution. Cunningham et al., 1991, supra. This attachment ensured uniform orientation of the hGHbp on the matrix unlike that obtained if random coupling through primary amine groups had been used. From the change in refractive index resonance units (RUs) that occurred during the coupling reaction, the amount of attached hGHbp was calculated from calibration curves supplied by Pharmacia (see the BIAcore™ biosensor manual).

When excess hGH was added to the (s237C)hGHbp-matrix, rapid association and extremely slow dissociation was observed. FIG. 1B. From the change in RU, a molar ratio of 0.4 hGH bound per immobilized hGHbp was calculated. See Table 1. This indicated that hGH dimerized the immobilized hGHbp as it did in solution. FIG. 1A. Dimerization on the matrix was further tested by measuring the binding to hGHbp of a non-dimerizing mutant of hGH, (G120R)hGH, which is blocked in its ability to bind Site 2.

Fuh et al., 1992, supra. When a saturating level of (G120R)hGH was added, it was found that about twice as much hormone bound (FIG. 1B), with a calculated stoichiometry of 0.7 (G120R)hGH per immobilized hGHbp (Table 1).

Analysis of the on- and off-rate profiles showed that both wild-type and (G120R)hGH associate at similar rates (Table 1). However, the off-rate for the wild-type was too slow to calculate a reliable dissociation constant. These data are consistent with the proposed sequential binding mechanism; that is, both hormones bound in the same way to the first receptor and hence have nearly the same on-rates. However, the wild-type hormone bound to the second receptor and thus was extremely slow to dissociate.

TABLE 1

Kinetic constants for binding of wild-type or (G120R)hGH to (S237C)hGHbp or (S201C)hGHbp immobilized on the thiol-matrix of the BIAcore ™ biosensor. On-rate and off-rate profiles were measured at 25° C. and analyzed for hGH and (G120R)hGH; average standard errors for on-rate, off-rate, and affinities on the same biosensor chip are 17%, 14%, and 21% of the value reported. Stoichiometries of binding were calculated from data in FIGS. 1B and 2B according to the following formula:

$$\frac{RU_{(max)} \text{hormone}}{RU_{(attached)} \text{hGHbp}} \times \frac{MW_{hGHbp}}{MW_{hormone}}$$

| Hormone | Matrix | Stoichiometry (hormone:hGHbp) | On-rate ($s^{-1}M^{-1}$) | Off-rate ($s^{-1}$) | $k_d$ (nM) |
|---|---|---|---|---|---|
| Wild-type | (S237C)hGHbp | 0.40 | $4.0 \times 10^5$ | $<1.0 \times 10^{-5}$ | ND* |
| G120R | (S237C)hGHbp | 0.70 | $2.6 \times 10^5$ | $4.3 \times 10^{-4}$ | 1.6 |
| Wild-type | (S201C)hGHbp | 0.84 | $3.0 \times 10^5$ | $2.7 \times 10^{-4}$ | 0.9 |
| G120R | (S201C)hGHbp | 0.92 | $1.4 \times 10^5$ | $3.7 \times 10^{-4}$ | 2.7 |

*ND = not determined.

Figure 2B:
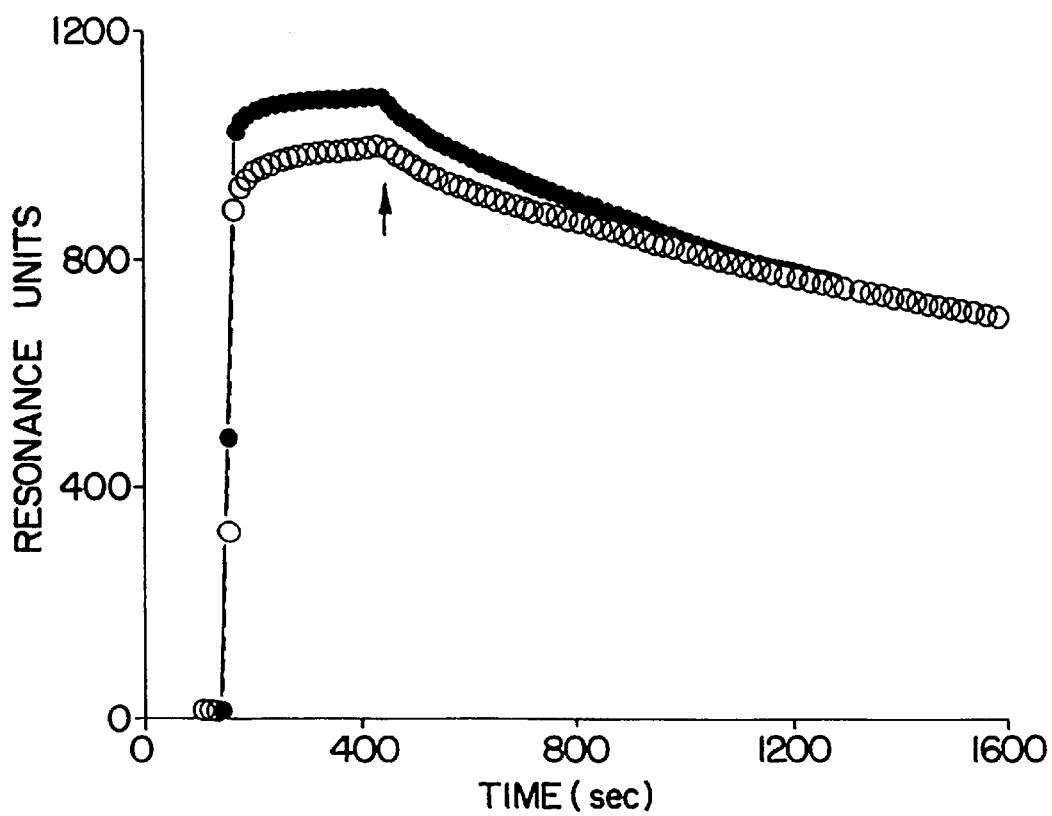

It was desired to investigate in greater detail the binding of mutants in the Site 1 contact epitope alone without the complication of the hGHbp dimerizing on the matrix. According to the x-ray structure of the $hGH(hGHbp)_2$ complex (De Vos et al., supra), the two hGHbps contact each other at Ser201. Therefore, dimerization on the matrix was blocked by replacing Ser201 with Cys and attaching the S201C variant via its single thiol to the activated-thiol matrix. FIG. 2A. Indeed, when saturating levels of hGH were added (FIG. 2B), a maximum stoichiometry of 0.84 hGH per immobilized (S201C)hGHbp (Table 1) was calculated. The (G120R)hGH bound with a stoichiometry of 0.94 per (S201C)hGHbp. By proper placement of the thiol-coupling, it was possible to orient the hGHbp on the matrix to allow for either 1:1 complex formation or 1:2 complex formation. Thus, the solution binding properties of hGH for the hGHbp can be reproduced on the BIAcore™ biosensor. The (G120R)hGH had virtually the same kinetics as hGH on the (S201C)hGHbp-matrix and the same as that of (G120R) hGH on the (S237C)hGHbp-matrix (Table 1). Together these data indicate that the (S201C)hGHbp-matrix is a reliable means of testing variants of hGH for binding to Site 1 alone.

A buried side-chain on hGH was defined as one that contains side-chain atoms whose accessibility to solvent changes when bound to the hGHbp at Site 1. Solvent accessibilities were calculated by rolling a 1.4 angstrom radium probe (Lee and Richards, *J. Mol. Biol.*, 55: 379–400 [1971]) over the surface of hGH when free or bound to one hGHbp through Site 1. For these calculations the x-ray coordinate set was used for the hGH(hGHbp)$_2$ complex. De Vos et al., supra. By this criteria there are 30 side-chains, all larger than alanine, which are buried to some degree upon complexation. Table 2.

TABLE 2

Relative on-rates, off-rates and affinities for alanine substitutions at residues in hGH that are buried to varying degrees at the Site 1 interface. Rate measurements were made using the hGHbp(S201C) matrix at 25° C. as described in Table 1.

| Site 1 contact residue | Changes in accessible area upon binding[1] (Å$^2$) | Vdw contacts[2] (H-bonds, h; salt bridges, s) | Changes in kinetics from wt[3] | | | ΔΔG (kcal/mol) BIAcore ™ (RIA)[4] |
|---|---|---|---|---|---|---|
| | | | off-rate | 1/on-rate | off/on | |
| Wild-type | — | — | (1) | (1) | (1) | (0) |
| M14 | 0.5 (0.6) | 0 | 1.2 | 1 | 1 | +0.1 (+0.5) |
| H18 | 23 (63) | 24 (hN218) | 0.41 | 1.1 | 0.44 | −0.5 (−0.7) |
| H21 | 3.7 (27) | 11 | 1.3 | 1.0 | 1.3 | +0.2 (+0.3) |
| Q22 | −2 (5.8) | 1 | 0.62 | 1.1 | 0.69 | −0.2 |
| F25 | 44 (63) | 21 | 0.47 | 1.0 | 0.47 | −0.4 (−0.2) |
| D26 | 0 (0.1) | 0 | 0.79 | 0.89 | 0.7 | −0.2 (−0.3) |
| Q29 | 4.2 (4.4) | 0 | 0.38 | 0.97 | 0.37 | −0.6 |
| Y42 | 60 (88) | 30 | 1.2 | 1.2 | 1.4 | +0.2 |
| L45 | −1.6 (44) | 7 | 4.3 | 1.8 | 7.9 | +1.2 (+1.4) |
| Q46 | 53 (88) | 16 (hE120) | 0.9 | 1.4 | 1.2 | +0.1 (0) |
| P48 | 3.8 (5.1) | 4 | 1.2 | 1.7 | 2.0 | +0.4 |
| S51 | 0 (0) | 0 | 1.2 | 1.4 | 1.8 | +0.3 |
| E56 | 0.5 (0.9) | 0 | 2.1 | 0.97 | 2.0 | +0.4 (+0.8) |
| P61 | 0 (5.1) | 0 | 7.2 | 1.1 | 7.7 | +1.2 |
| S62 | 1.8 (14) | 1 (hS102) | 1.6 | 0.8 | 1.3 | +0.1 |
| N63 | 7.1 (17) | 2 | 1.2 | 1.4 | 1.7 | +0.3 (+0.7) |
| R64 | 57 (101) | 24 (sD164, sE44) | 7.9 | 2.1 | 16 | +1.6 (+1.8) |
| E65 | 3.3 (3.3) | 0 | 0.69 | 0.66 | 0.45 | −0.5 (−0.3) |
| Q68 | 6.4 (26) | 2 | 3.3 | 0.8 | 2.7 | +0.6 (+1.0) |
| Y164 | −5.7 (24) | 4 | 2.1 | 0.9 | 1.8 | +0.3 (+0.8) |
| R167 | 5.9 (32) | 8 (sE127) | 0.49 | 3.3 | 1.6 | +0.3 (−0.2) |
| K168 | 15 (60) | 12 (hW104mc) | 0.64 | 1.2 | 0.77 | −0.2 (+0.1) |
| D171 | 19 (50) | 16 (sR43) | 4.6 | 0.83 | 3.8 | +0.8 (+1.2) |
| K172 | −6.5 (27) | 15 | 20 | 1.5 | 30 | +2.0 (+1.6) |
| E174 | 17 (25) | 4 (hN218) | 0.33 | 0.61 | 0.21 | −0.9 (−0.9) |
| T175 | −2.1 (47) | 9 (hR43) | 25 | 1.0 | 25 | +2.0 |
| F176 | −14 (5.8) | 4 | 22 | 1.1 | 2 | +1.9 (+1.6) |
| R178 | 41 (70) | 8 (hI165mc, hM170mc) | 24 | 2.5 | 60 | +2.4 (+2.4) |
| I179 | −10 (26) | 9 | 2.9 | 1.3 | 3.9 | +0.8 (+0.6) |

TABLE 2-continued

Relative on-rates, off-rates and affinities for alanine substitutions at residues in hGH that are buried to varying degrees at the Site 1 interface. Rate measurements were made using the hGHbp(S201C) matrix at 25° C. as described in Table 1.

| Site 1 contact residue | Changes in accessible area upon binding[1] (Å$^2$) | Vdw contacts[2] (H-bonds, h; salt bridges, s) | Changes in kinetics from wt[3] | | | ΔΔG (kcal/mol) BIAcore ™ (RIA)[4] |
|---|---|---|---|---|---|---|
| | | | off-rate | 1/on-rate | off/on | |
| R183 | 1.2 (1.5) | 0 | 1.4 | 1.8 | 2.5 | +0.5 (+0.4) |
| E186 | 3.4 (5.6) | 0 | 0.97 | 1.0 | 0.98 | 0 (−0.1) |

[1]Accessible surface area to a 1.4 Å probe was calculated (Lee and Richards, supra) for each side-chain in the wild-type hormone and for wild-type missing atoms beyond the β-carbon (to mimic the alanine mutant) and for their corresponding complexes with the hGHbp using X-ray coordinates. De Vos et al., supra. The change in area buried attributed to the alanine mutation is the difference in accessible area of (free-bound)$_{wt}$-(free-bound)$_{Ala}$. The area only used was that buried beyond the β-carbon because this is the portion of the side-chain removed upon alanine substitution. Shown in parentheses is the area of each side-chain for atoms beyond the β-carbon in hGH that become inaccessible to solvent once the receptor binds.
[2]Total number of van der Waals contacts is the number of receptor atoms within 4.4 Å of any atom beyond the β-carbon of the contact side-chain based on inspection of the hGH(hGHbp)$_2$ complex. Over 80% of the contact distances are 3.8 to 4.2 Å. Groups making hydrogen bonds (h) or salt-bridges (s) are determined by donor-acceptor or complementary charge pairs within 3.3 Å of each other between hGH and the hGHbp. For example, hN218 next to H18 indicates a H-bond between H18 on hGH and N218 of the hGHbp. mc indicates an H-bond to a main-chain amide.
[3]The relative change in off-rate was calculated from $$\frac{k_{off} wt}{k_{off} Ala \, mut} \text{ and for 1/on-rate by } \frac{k_{on} Ala \, mut}{k_{on} wt}$$

The change in K$_d$ from wild-type was calculated as:

$$\frac{K_d(Ala \, mut)}{K_d(wt)} = \frac{K_{off}/k_{on}(mut)}{k_{off}/k_{on}(wt)}$$

[4]The ΔΔG values were calculated as +RT1n $$\frac{K_d(Ala \, mut)}{K_d(wt)}$$

from BIAcore ™ biosensor data or in parentheses from radioimmunoassay data that was previously reported. Cunningham and Wells, supra; Cunningham and Wells, Proc. Nat. Acad. Sci. USA, 88: 3407–3411 (1991).

Figure 3:
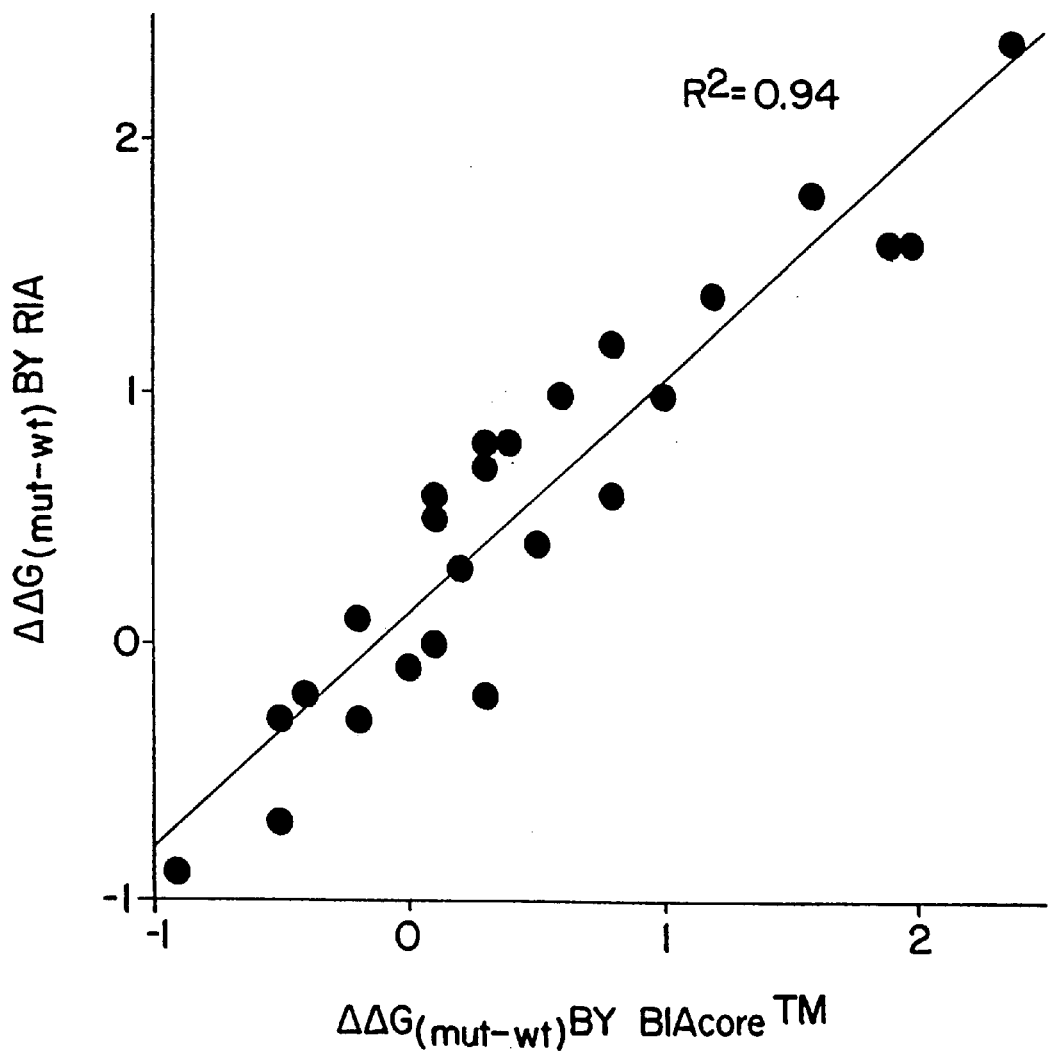
FIG. 3 shows the correlation between the change in the free energy of binding ($\Delta\Delta G_{(mut-wt)}$) calculated for alanine mutants of hGH relative to wild-type hGH when forming a 1:1 complex with the hGHbp from data obtained by RIA (y-axis) or BIAcore™ biosensor (x-axis). Values were taken from Table 2.
Figure 4A:
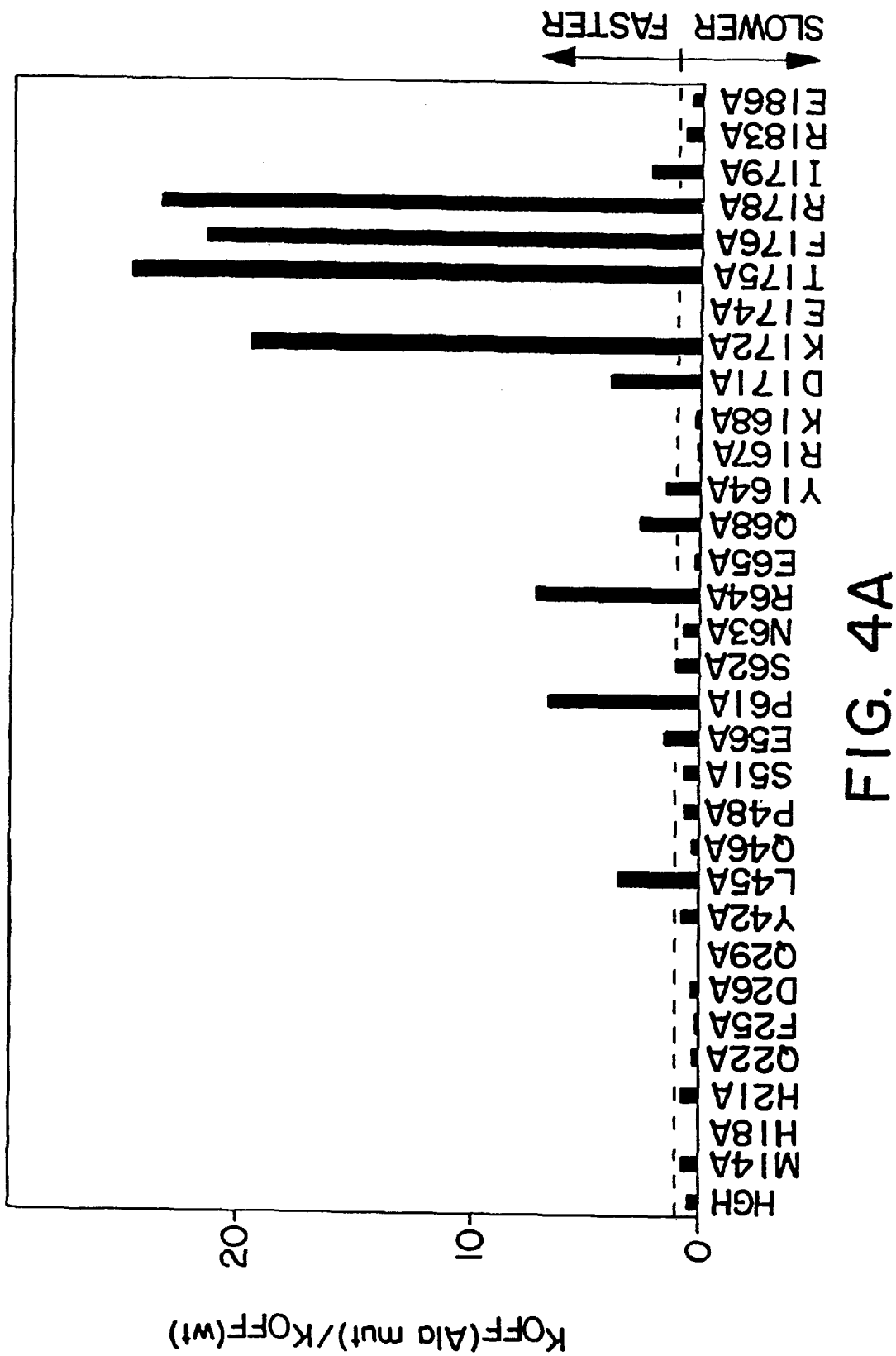
FIGS. 4A and 4B show the relative change in off-rate (FIG. 4A) or on-rate (FIG. 4B) for alanine mutants at contact residues. Data is taken from Table 2.
Figure 4B:
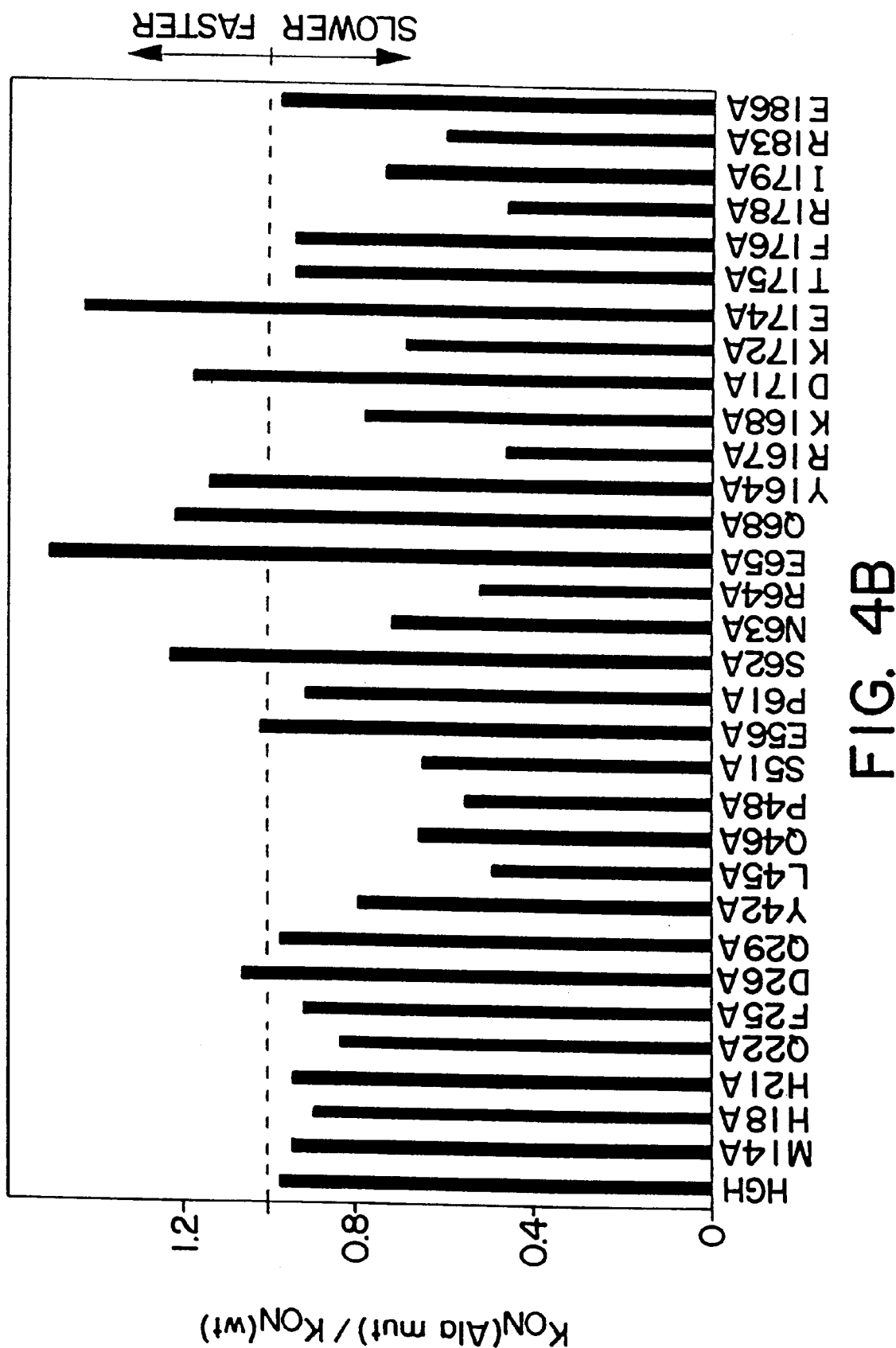

The (S201C)hGHbp-matrix was used to measure the affinities for alanine mutants at the 30 buried residues in the Site 1 interface (Table 2). Previously used was a radioimmunoprecipitation assay (RIA) to measure the binding constants for many of these mutants. Cunningham and Wells, 1989 and 1991, supra. A plot of the change in free energy relative to wild-type for the alanine mutants calculated by RIA data versus BIAcore™ biosensor data shows a tight correlation ($R^2 = 0.94$) with a slope near unity and an intercept close to zero. FIG. 3. Thus, the affinity data acquired on the biosensor matrix closely matches those measured in solution by the RIA. This indicates the matrix is not causing systematic binding artifacts. The average standard error in affinity constant is about 20% for using the BIAcore™ biosensor versus about 30% for the RIA. It is also possible that some dimerization of the hGHbp can occur in the RIA that would lead to systematic errors in affinities; this is prevented using the (S201C)hGHbp-matrix.

Figures 5A, 5B:
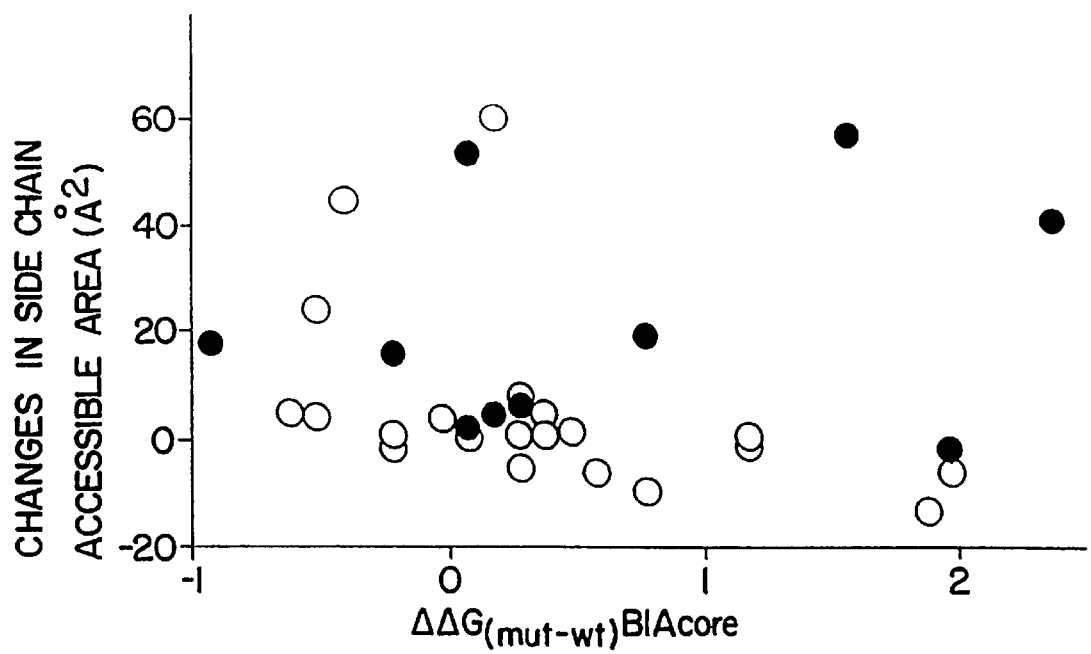
FIGS. 5A and 5B show the relationship between the change in binding affinity upon alanine substitution and the change in buried surface area (Å$^2$) (FIG. 5A) or number of van der Waals contacts (FIG. 5B) for atoms in contact side-chains beyond the β-carbon. Closed circles are for residues buried at the interface that make hydrogen bonds or salt bridges with the receptor at Site 1, and open circles are for residues that do not. Data are plotted from Table 2.

Of the 30 buried side-chains, only 7 (L45, P61, R64, K172, T175, F176, and R178) can account for about 85% of the total change in binding free energy resulting from the alanine substitutions. Another six (P48, E56, Q68, D171, I179, and R183) can essentially account for the remainder (Table 2). Eight other buried side-chains (M14, H21, Q46, S62, N63, Y164, R167, and E186) have essentially no effect on overall affinity (each causing less than 2-fold reduction in affinity). Three other buried side-chains (Q22, D26, and K168) have a small but significant effect on binding affinity. Five side-chains (H18, F25, Q29, E65, and E174) actually hinder binding because when they are converted to alanine, there are enhancements in affinity of 2 to 5-fold. The sum of the reductions in free energies caused by the alanine substitutions (−14.2 kcal/ml) is comparable to the total free energy of binding between hGH and the hGHbp (~12.3 kcal/mol) measured by the BIAcore™ sensor.

Thus, an hGH mutant with changes at H18, Q22, F25, D26, Q29, E65, K168, and E174 has increased binding affinity for hGHbp. The variant with all alanine residues at these positions is calculated to have a binding affinity about 200-fold greater than that of wild-type hGH based on the additivity of individual amino acid changes. In conjunction with the data in Example II herein, it is expected that an Asp at position 18 and/or a Ser at position 174 in this combination mutant would also have a significantly greater binding affinity toward hGHbp than wild-type hGH.

The off-rate effects are much larger than the on-rate effects (Table 2; FIG. 4). Thus, the same seven residues that most affect affinity account for most of the increase in off-rate (up to 25-fold). The conversion of three Arg side-chains (R64, R167, and R178) to Ala produced the greatest reductions in on-rate, but only about 2-fold. The conversion of two Glu side-chains (E65 and E174) to Ala caused the greatest increases in on-rate (nearly 2-fold improved). This indicates that electrostatic interactions are the most important side-chain determinants in guiding the hormone to the receptor.

The side-chains that most affect on-rate are not all the same as those that most affect off-rate. FIG. 4. For example, R167A causes the largest decrease in on-rate but leads to a compensating decrease in off-rate. Many of the alanine mutations at side-chains that dominate the affinity (P61A, K172A, T175A, and F176A) have virtually no effect on the association rate. The preferred combination mutant from these experiments, which has a 200-fold greater binding affinity for the GH receptor than wild-type hGH, resulting from the additivity of each mutation, has the sequence H18A, Q22A, F25A, D26A, Q29A, E65A, K168A, E174A.

Conclusion

The data indicate that only a small set of the buried side-chains at the interface are functionally crucial in binding. Without being limited to any one theory, it is believed that this is not an artifact of the method of analysis. First, the structure of the hGH.hGHbp complex has been solved and the residues buried in Site 1 are virtually identical to those seen in Site 1 for hGH in the hGH(hGHbp)$_2$ complex. De Vos et al., supra. Thus, the fact that the structural epitope is much smaller than the functional epitope is not because of contact differences in binding in the 1:1 versus the 1:2 complex (which is the coordinate set used to define the contact epitope).

Second, analysis of the functional importance of any side-chain by mutational study has the caveat that the mutant protein can exaggerate the effect by imposing a structural disturbance or an unusual steric, electrostatic, or hydrophobic interaction. Systematic replacements of side-chains with alanine are least disruptive to the structure. Wells, *Methods in Enzymol.,* 202: 390–411 (1991). The alanine mutation is the simplest to interpret because it removes atoms without introducing new ones that can create additional unfavorable or favorable interactions. The sum of all the disruptive effects caused by the alanine substitutions (−14.3 kcal/mol) does not dramatically exaggerate the total binding free energy (−12.3 kcal/mol). This indicates that the effects are localized to the individual binding determinants and do not grossly change the whole protein structure or the mode of binding. Given the large number of contact residues, it is also unlikely that single alanine substitutions would change the mode of binding in the complex, which is evidenced by the number of double alanine substitutions that have additive effects on binding, indicating that the sites act independently.

Also identified are some alanine mutations that affect affinity that are buried in the hormone and do not become further buried when the receptor binds. Cunningham and Wells, 1989, supra. For example, P5A, L6A, F10A, and V185A each disrupt affinity by 2- to 4-fold. Each of these side-chains makes contacts between helix 1 and helix 4 that dominate the Site 1 epitope but are not directly involved in binding. Similarly, F54 and I58 disrupt affinity and are buried in the loop region that positions the second mini-helix. This mini-helix contains R64 and other important binding determinants. Thus, some minor effects on binding can result from structural perturbations that are propagated from alanine mutations near but not at the structural epitope. However, the vast majority of residues tested away from the Site 1 structural epitope have no detectable effect on binding when converted to alanine. Cunningham and Wells, 1989, supra.

The alanine-scanning data show only seven of 30 side-chains buried at the interface account for about 85% of the binding energy. Virtually all of the rest can be accounted for by six other side-chains. It has been attempted to correlate a number of structural parameters that can explain why some residues are critical for binding and others are not. The residues are found important for binding cluster in a small region near the center of the structural epitope (mostly toward the end of helix 4). The functionally "null" contact residues tend to be near the periphery, in the center of helix 1 and the beginning of helix 4. This is a region that is critical for binding of hGH to the hPRL receptor (Cunningham and Wells, 1991, supra) and for forming a $(Zn^{+2}.hGH)_2$ storage complex. Cunningham et al., *Science,* 253: 545–548 (1990). Thus, while this area has little apparent role in binding to the hGH receptor, it does have other important functions.

Other systematic structural correlations are more difficult to make. Chothia and Janin, *Nature,* 256: 705–708 (1975) found that a change in buried surface area generally correlated with the free-energy of association between two proteins. The change in buried surface area that would occur upon complex formation for each of the alanine mutants was calculated from the difference in accessibility in the free and bound states between hGH and the alanine mutant. Table 2. However, a plot of the change in buried surface area upon binding versus the change in the free energy of binding when the side-chain is converted to alanine gives a very poor correlation. FIG. 5A. In some cases negative values for change in accessibility were obtained. This is because the missing side-chain in the alanine mutant creates a cavity at the interface, and hence more surface area would be covered upon complex formation. Also calculated was the change in side-chain accessibility that occurs upon binding for atoms beyond the beta-carbon that was the criterion for defining buried side-chains (see value in parentheses in column 2 of Table 2). Yet a plot of these values versus the change in free energy gives no better correlation. A plot of the number of van der Waals contacts made by atoms of hGH beyond the beta-carbon versus the change in affinity when the side-chain is converted to alanine (FIG. 5B) does not show a good correlation either. Neither correlation improves by considering separately the side-chains that are capable of electrostatic interactions.

Horton and Lewis, *Protein Science*, 1: 169–181 (1992) were able to predict affinities for 15 different protein—protein pairs using a semi-empirical method based on buried surface area and functional scaling of atomic salvation parameters (Eisenberg and McLachlan, *Nature*, 319: 199–203 [1986]) for the contact side-chains. Therefore, these scaled atomic salvation parameters were evaluated to see how well they can predict the free-energy changes resulting from the individual alanine substitutions. There was little correlation. Thus, while buried surface area, number of van der Waals contacts, and scaled atomic solvation calculations are useful correlates for general binding affinity, they are poor predictors of the role of individual side-chains in this epitope.

On average, the energetics for electrostatic interactions are considerably weaker than estimates made from mutagenesis of enzyme-substrate complexes. From mutational analysis of tyrosyl-tRNA synthetase, it was estimated that the free energy loss for disrupting a charged H-bond pair is 3.5–5 kcal/mol and for a neutral H-bond pair is 0.5–1.5 kcal/mol. Fersht et al., *Nature*, 314: 235–238 (1985). Seven side-chains from hGH form hydrogen bonds with the hGHbp (H18, Q46, S62, K168, E174, T175, and R178). Five of these are charged H-bonds (Q46, K168, E174, T175, R178), yet the change in binding free energy when they are converted to alanine is only +0.1, −0.2, −0.9, +2.0, and +2.0 kcal/mol, respectively, giving an average value of +0.6 kcal/mol. The change in affinity for mutating the two neutral H-bonding side-chains (H18 and S62) is only −0.5 and +0.1, respectively. Three other side-chains form salt-bridges with the hGHbp (R64, R167, and D171), yet these cause reductions of only +1.6, +0.3, and +0.8 kcal/mol, respectively. These values are less than ones estimated for two engineered salt bridges in subtilisin that range from +1.8 to +2.3 kcal/mol. Wells et al., *Proc. Natl. Acad. Sci. USA*, 84: 1219–1223 (1987). Thus, the strength of the contacts varies widely in the hGH-hGHbp interface and the interactions are considerably weaker when compared with those of small molecule binding sites.

From mutational studies of protein interiors it has been estimated that each buried methylene group contributes −1.0 to −1.5 kcal/mol to the overall free-energy of folding (for recent review see Shortle, *Quart. Rev. Biophys.*, 25: 205–250 (1992), and references therein). Converting a number of hydrophobic side-chains in hGH to alanine caused effects that were very much weaker than would be expected from these studies. For example, the largest effects seen for mutations at hydrophobic side-chains are for L45A, K172A (only the aliphatic portion makes contact with the receptor), F176A, and I179A, which cause reductions in affinity of +1.2, +2.0, +1.9, and +0.8 kcal/mol, respectively. Moreover, several other hydrophobic groups that are more highly or comparably buried upon complex formation (F25, Y42, Y164) have almost no effect when mutated to alanine.

In summary, a striking feature of the 1:2 hGH:receptor complex has been found, i.e., that only a small set of the side-chains from hGH that are buried in Site 1 affect binding affinity when converted to alanine. Thus, the functional epitope defined by alanine-scanning mutagenesis is considerably smaller than the structural epitope defined by buried residues or van der Waals contacts. Some residues that are near but not within the Site 1 epitope can modestly affect binding affinity when converted to alanine, presumably by indirect effects. Finally, most of the functionally important side-chains modulate off-rate, not on-rate, of the hormone to the receptor.

EXAMPLE II

Purpose

It was desired to determine to what degree affinity of the Site 1 of hGH could be enhanced. It was also desired to determine which side-chains of hGH should be mutated to enhance binding affinity—ones that modulate affinity as identified by alanine-scanning mutagenesis, ones identified by crystallography to make contact, or both. Finally, if mutations can substantially enhance affinity, it was desired to learn whether they do so by affecting the on-rate or the off-rate of the mutated hormone.

Summary

Very high affinity variants of hGH were produced by combining affinity-enhanced mutants of hGH that were sorted from five separate libraries in which a total of about $10^6$ protein variants were displayed monovalently on phagemid particles. Altogether 20 different residues in the Site 1 binding site were mutated. Although only small increases in affinity were contributed from each mutant side-chain, these produced additive increases in the free-energy of binding. By this approach, an hGH variant was produced having 15 substitutions that bound receptor about 400-fold tighter than wild-type hGH.

Materials and Methods a) General Procedures

Restriction enzymes, polynucleotide kinase, $T_7$ DNA polymerase, and $T_4$ DNA ligase were obtained from Gibco-BRL or New England Biolabs and used according to the manufacturer's directions. Randomized oligonucleotide cassettes were phosphorylated, annealed, and ligated into constructs as described in Lowman et al., supra, and Lowman and Wells, supra. Sequenase® brand enzyme was purchased from United States Biochemical and used according to the manufacturer's directions for single-stranded sequencing. Sanger et al., supra.

Some site-specific mutants of hGH were constructed by oligonucleotide-directed mutagenesis, using single-stranded template. Kunkel et al., *Methods Enzymol.*, 204: 125–139 (1991). The plasmid phGHam-g3, encoding wild-type hGH fused to the carboxy-terminal domain of M13 geneIII (Lowman et al., supra), was used to construct parental vectors for cassette mutagenesis. Monovalent hGH-displaying phagemid particles were prepared (Lowman and Wells, supra) by electrotransforming *E. coli* XL1-Blue cells (Stratagene), and adding M13K07 helper phage. Vieira and Messing, supra.

DNA molecules encoding the soluble hormones were expressed in *E. coli* (Chang et al., supra), ammonium-sulfate precipitated from osmotically shocked cell supernatants (Olson et al., *Nature*, 293: 408 [1981]), and quantitated by laser densitometry of Coomassie-stained SDS-PAGE gels. Cunningham et al., supra. Some variants were further purified by ion-exchange chromatography on a Mono-Q column (Pharmacia-LKB Biotechnology, Inc.).

(b) Preparation of hGH-phagemid libraries

For mutagenesis of Minihelix-1 (residues 41–46) of hGH, the existing AatII site in phGHam-g3 was destroyed using oligonucleotide #718 (5'-GCC ACC TGA TGT CTA AGA AAC-3') (SEQ. ID NO. 1). Unique SfiI and AatII sites were introduced into phGHam-g3 to create pH0779, using oligonucleotides #782 (5'-TTT GAA GAG GCC TAT ATG GCC AAG GAA CAG AAG-3') (SEQ. ID NO. 2) and #821 (5'-CAG AAC CCC CAT TGA CGT CCC TCT GTT TC-3') (SEQ. ID NO. 3), respectively. The latter oligonucleotide also introduced a +2 frameshift and a TGA stop codon after residue 49. A randomized cassette was constructed from the complementary oligonucleotides #822 (5'-TC CCG AAG GAG CAG NNS NNS TCG TTC NNS NNS AAC CCG CAG ACG T-3') (SEQ. ID NO. 4) and #823 (5'-CTG CGG GTT SNN SNN GAA CGA SNN SNN CTG CTC CTT CGG GAT AT-3') (SEQ. ID NO. 5). The parental DNA (pH0779) was digested with restriction enzymes SfiI and AatII, and the large fragment was purified and ligated with the cassette. The ligation products were electro-transformed into XL1-Blue cells for phagemid preparation in two aliquots, yielding 1×10⁶ independent transformants each, as described by Lowman and Wells, supra.

To construct the Loop-A (residues 54–64) library of hGH, the existing AatII site in phGHam-g3 was destroyed using oligonucleotide #718. UniTue AatII and BstEII restriction sites were introduced in the hGH gene to construct pH0709, using oligonucleotides #719 (5'-AAC CCC CAG ACG TCC CTC TGT-3') (SEQ. ID NO. 6) and #720 (5'-GAA ACA CAA CAG TAA AGG TAA CCT AGA GCT GCT-3') (SEQ. ID NO. 7). The latter oligonucleotide also introduced a +1 frameshift and a TAA stop codon after residue 69. In addition, the unique EcoRI site was destroyed using oligonucleotide #536 (5'-CGT CTT CAA GAG TTC AAC TTC TCC-3') (SEQ. ID NO. 8), to permit restriction-selection against possible contaminating clones from previous libraries (Lowman and Wells, supra). A randomized cassette was constructed from the complementary oligonucleotides #803 (5'-pCC CTC TGT NNS TCA NNS TCT NNS CCG ACA CCC AGT AAT NNS GAG GAA ACA CAA CAG AAG A-3') (SEQ. ID NO. 9) and #804 (5'-pGTT ACT CTT CTG TTG TGT TTC CTC SNN ATT ACT GGG TGT CGG SNN AGA SNN TGA SNN ACA GAG GGA CGT-3') (SEQ. ID NO. 10). The parental DNA (pH0709) was digested with restriction enzymes AatII and BstEII, and the large fragment was purified and ligated with the cassette. The ligation products were electro-transformed into XL1-Blue cells for phagemid preparation in two aliquots, yielding 1.6×10⁶ and 1.0×10⁶ independent transformants.

(c) Combinatorial hGH libraries from hGH-phagemid library pools

DNA from the Helix-1 and the Helix-4b pools (selected for 0, 2, or 4 rounds; Lowman et al., supra) was purified and digested with the restriction enzymes AccI and BstXI. The large fragment from each Helix-1 pool (randomly mutated at F10, M14, H18, and H21) was then purified and ligated with the small fragment from each Helix-4b pool (randomly mutated at R167, D171, T175, I179, in the E174S, F176Y background) to yield the three combinatorial libraries 707A (un-selected Helix-1 and Helix-4b pools), 707B (twice-selected Helix-I pool with twice-selected Helix-4b pool), and 707C (4-times selected Helix-1 pool with 4-times selected Helix-4b pool). Duplicate ligations were also set up with one-tenth to one-half as much vector DNA and designated as 707D, 707E, and 707F, corresponding to the 0-, 2-, and 4-round starting libraries, respectively. All of these variant pools also contained the mutations E174S, F176Y obtained in earlier hGH-phagemid-binding selections. Lowman et al., supra. The ligation products pH0707A–F were processed and electro-transformed into XL1-Blue cells. The number of independent transformants obtained from each pool, based on colony-forming units (CFU), was as follows: 2.4×10⁶ from pH0707A, 1.8×10⁶ from pH0707B, 1.6×10⁶ from pH0707C, 8×10⁵ from pH0707D, 3×10⁵ from pH0707E, and 4×10⁵ from pH0707F. hGH-phagemid particles were prepared and selected for hGHbp-binding over 2 to 7 cycles as described by Lowman et al., supra.

Several variants of hGH were constructed by combining isolated variants from the Helix-1 and Helix-4b libraries. The parental variants were the three tightest-binding from each library: A=H10, G14, N18, N21; B=A10, W14, D18, N21; C=F10, S14, F18, L21; D=N167, S171, S174, Y176, T179; E=E167, S171, S174, Y176, I179; F=N167, N171, S174, Y176, T179. hGH-phagemid DNA was purified and digested with the restriction enzymes EcoRI and BstXI. The large fragment from each Helix-4b variant was then purified and ligated with the small fragment from each Helix-1 variant to yield combined variants with mutations in both Helix-1 and Helix-4b. These variants were designated as AD, AE, AF, BD, BE, BF, CD, CE, CF to indicate the respective pairwise combinations of Helix-1 (A, B, or C) and Helix-4b (D, E, or F) mutations.

A series of five oligonucleotides was used to revert several of the phage-derived mutations in the variant BD to the corresponding wild-type residue: #797 (5'-CTG CGT GCT CAC CGT CTT CAC CAG TTG GCC TTT G-3') (SEQ. ID NO. 11) for D18H, N21H; #798 (5'-GTC AGC ACA TTC CTG CGC ACC-3') (SEQ. ID NO. 12) for Y176F; #799 (5'-CTC TCG CGG CTC TTC GAC AAC GCG ATG CTG CGT GCT-3') (SEQ. ID NO. 13) for A10F, W14M; #800 (5'-TAC TGC TTC AGG AAG GAC ATG GAC AAG GTC AGC-3') (SEQ. ID NO. 14) for N167R, S171D; #801 (5'-CTG CGC ATC GTG CAG TGC-3') (SEQ. ID NO. 15) for T179I; #875 (5'-CTC TCG AGG CTC TTC GAC AAC GCG TGG-3') (SEQ. ID NO. 16) for A10F.

The hGH variant 852d was constructed using BD as template and the following oligonucleotides: #843 (5'-CAG ACC TCC CTC TGT CCC TCA GAG TCT ATT CCG-3') (SEQ. ID NO. 17) for adding F54P; #844 (5'-ACA CCC TCC AAC AAG GAG GAA ACA CAA CAG-3') (SEQ. ID NO. 18) for R64K; #846 (5'-CCA AAG GAA CAG ATT CAT TCA TTC TGG TGG AAC CCC CAG ACC TCC-3') (SEQ. ID NO. 19) for K41I, Y42H, L45W, Q46W. Variant 852b was constructed using the same oligonucleotides with template phGHam-g3.

(d) Radio-immunoprecipitation assays

The equilibrium binding affinity for hGHbp was determined by assaying hGH variants in competition with $^{125}$I-labeled hGH, labeled variant BD, or labeled variant 852d, in binding buffer: 50 mM Tris, pH 7.5, 10 mM $MgCl_2$, 0.1% bovine serum albumin, 0.02% sodium azide. Lowman et al., *J. Biol. Chem.*, 266: 10982–10988 (1991). Immunoprecipitation of the hGH-hGHbp complex was carried out using a monoclonal antibody designated MAb5. Barnard et al., *Endocrinology*, 115: 1805–1813 (1984). Dissociation constants were obtained by Scatchard analysis. Cunningham and Wells, 1989, supra. Variants BD and 852d contain F176Y, which if iodinated could perturb the hormone-receptor interface. However, iodinated BD (cold) was indistinguishable from unlabeled BD in competing with $^{125}$I-labeled BD for binding.

(e) Kinetics assays

Association and dissociation rate constants for hGH variants binding to immobilized hGHbp were obtained by measurement of surface plasmon resonance (SPR) using a Pharmacia BIAcore™ biosensor. In this system, hGHbp is covalently coupled to a dextran matrix attached to a biosensor chip. The hormone is maintained at constant concentration in a liquid phase passing over this surface at a constant flow rate. The instrument measures the mass of protein binding to the matrix in real time by sensing the change in SPR signal due to the change in refractive index near the biosensor surface. Löfås and Johnsson, *J. Chem. Soc. Chem. Commun.*, 21: 1526–1528 (1990).

A variant of hGHbp(S201C) was used as the immobilized species because binding of a second receptor on the matrix is blocked (see Example I). The hGHbp(S201C) was reduced and coupled to the biosensor chip via EDC/NHS activation of the dextran layer and 2-(2-pyridinyldithio) ethaneamine hydrochloride (PDEA) (activated thiol) chemistry to a level of 1000–2000 RU's, using 10 mM sodium acetate (pH 5.0); reagents and procedures were obtained from Pharmacia Biosensor. Binding and elution steps were carried out at a flow rate of 3–20 μL/min in PBS buffer (pH 7.4) containing 0.05% Tween-20.

The density of the hGHbp coupled to the matrix affects the absolute but not relative $k_{on}$ and $k_{off}$ values by up to two-fold for wild-type hGH. Thus, when different biosensor chips were used the kinetic parameters for the wild-type hGH were determined so that they could be normalized for comparing different mutants whose kinetic parameters can have been measured on different biosensor chips. The relative kinetic values so obtained were consistent over different flow-cells, and calculated affinity measurements correlated well with the results of the radio-immunoprecipitation assay. Dissociation rate constants were obtained by plotting $\ln(R_o/R_t)$ vs t; association rate constants were obtained by plotting [Slope of $(dR_t/dt)$ vs. $R_t$] against hormone concentration (Karlsson et al., supra), or by plotting $\ln(dR_t/dt)$ against hormone concentration using the BIAcore™ biosensor kinetics evaluation software (Pharmacia Biosensor). Equilibrium dissociation constants, $K_d$'s, were calculated as $k_{off}/k_{on}$. Standard deviations, $\sigma_{on}$ for $k_{on}$ and $\sigma_{off}$ for $k_{off}$, were obtained from measurements with 2 or more series of 2-fold or 3-fold dilutions ($k_{on}$) or with 2 or more concentrated ($\geq 5$ μM) hormone samples ($k_{off}$). The resulting errors ($\epsilon([K])$ in calculated $K_d$'s were estimated according to the following formulas using the total derivative of $K=f(k_{on}, k_{off})$: (for a discussion, see Bevington, supra)

$$\epsilon[K] = [(\delta K/\delta k_{off})^2 (d[k_{off}])^2 + (\delta K/\delta k_{on})^2 (d[k_{on}])^2]^{1/2} \quad (1)$$

$$\epsilon[K] = [(k_{on})^{-2} (\sigma_{off})^2 + (k_{off})^2 (k_{on})^{-4} (\sigma_{on})^2]^{1/2}. \quad (2)$$

Results (a) Residues in the hGH-receptor binding functional epitope

Figure 6A:
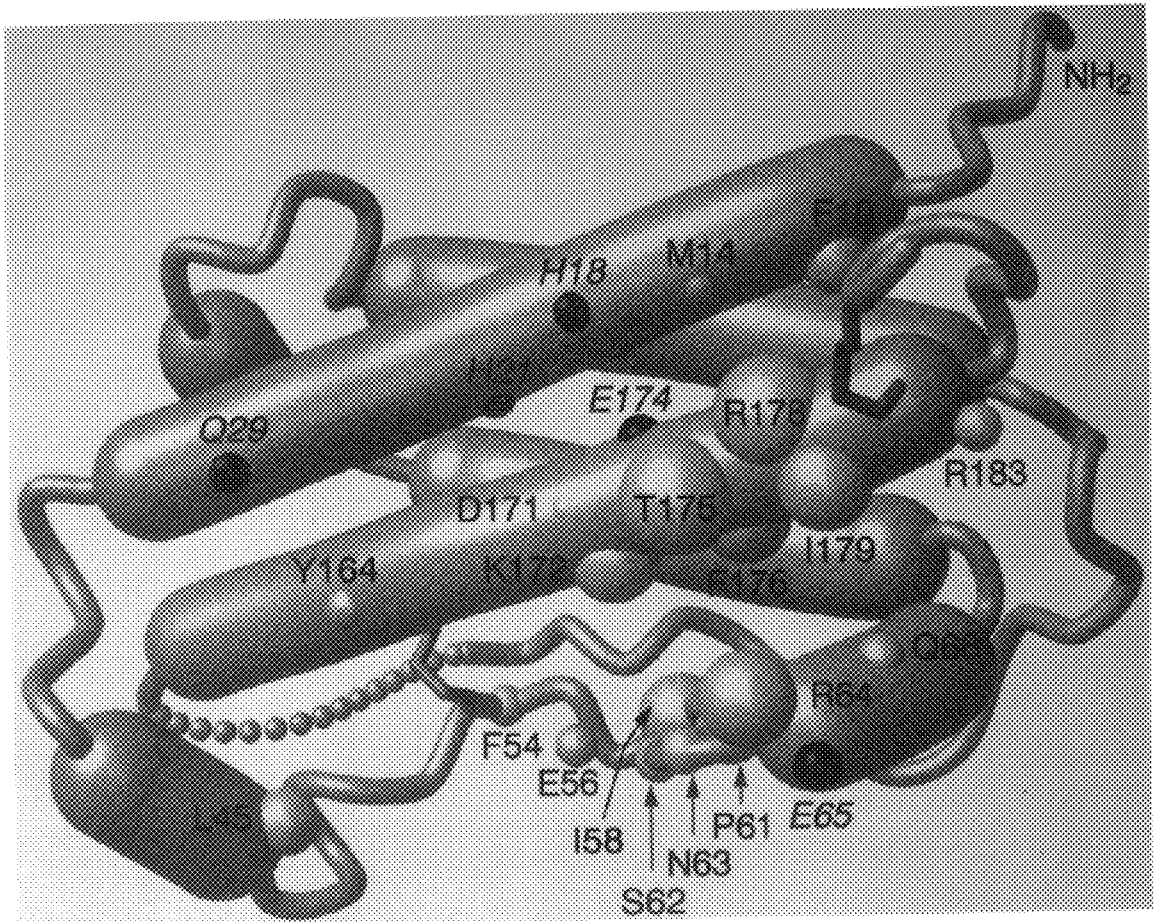
FIGS. 6A, 6B, and 6C show a comparison of receptor binding epitopes defined by alanine-scanning mutagenesis, x-ray crystal structure, or phage display, respectively.
Figure 6B:
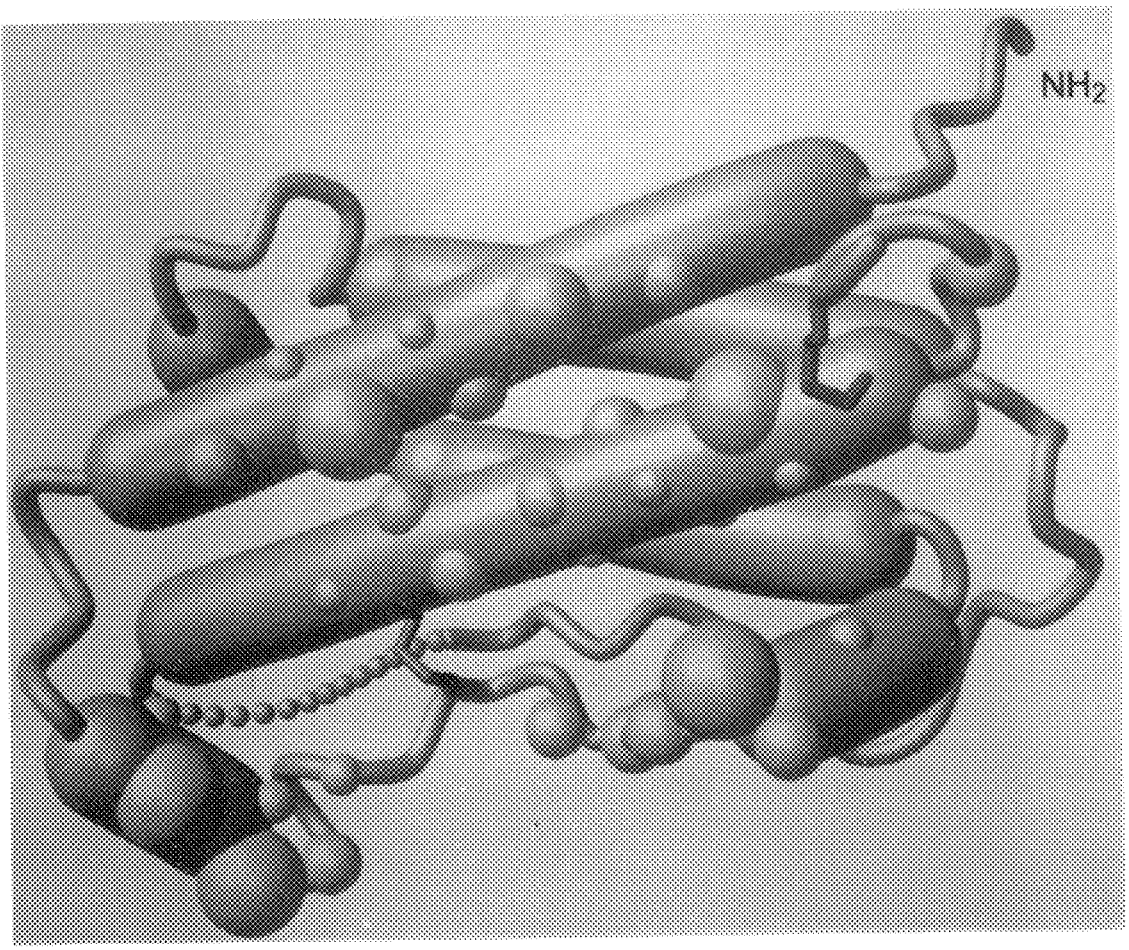
Figure 6C:
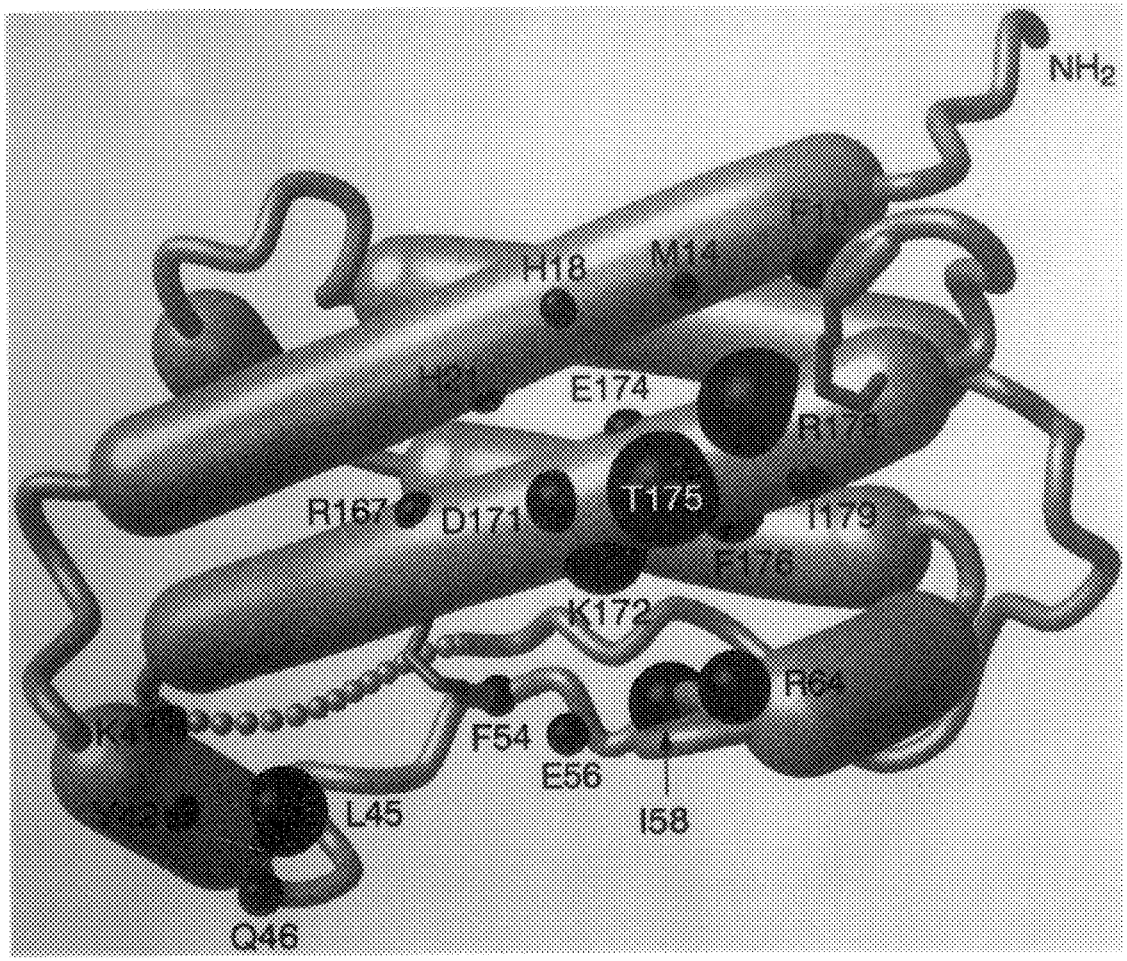

Structural analysis of the hGH(hGHbp)$_2$complex (de Vos et al., supra) identified over 30 side-chains in Site 1 of hGH that undergo some degree of burial when the first receptor binds (FIG. 6B). Although most of these were tested as alanine mutants prior to the structural elucidation (Cunningham and Wells, 1989, supra; 1991, supra), four residues (K41, Y42, L45 and Q46) in the first minihelix (Minihelix-1) were not evaluated. Therefore, these residues were converted singly to alanine and the effects on binding affinity were measured either by competitive displacement with [$^{125}$I]-hGH and immunoprecipitation (Cunningham and Wells, 1989, supra) or using the BIAcore™ biosensor from Pharmacia. Both methods gave comparable affinity measurements, as shown in Example I.

The side-chains of Y42 and Q46 became highly buried upon receptor binding, yet alanine replacements caused less than a two-fold reduction in affinity (Table 3). Leu 45 makes fewer contacts with the receptor than Y42 or Q46, yet the L45A mutant causes a 10-fold reduction in affinity. Lys41 makes a salt-bridge with Glu127 of the receptor. The DNA encoding the K41A mutant did not express well enough to obtain material for an affinity measurement; however, DNA encoding a more conservative variant, K41Q, did express sufficiently well. This variant had a 2.6-fold lower affinity than wild-type hGH. Thus, the Minihelix-1 region is clearly part of the functional epitope in hGH Site-1 (FIG. 6A). With these data and those of Example I, the effects have been measured for at least one replacement (mostly alanines) at residues whose side-chains become buried when the first receptor binds at Site 1.

TABLE 3

Receptor binding affinities of hGH alanine mutants in wild-type background, measured by BIAcore ™ (†) or by RIA (unmarked) and normalized relative to the RIA value for wild-type hGH as measured by Cunningham et al., 1989, supra. Alanine or glutamine mutations were made to test the contributions of side-chains in the Minihelix-1 region of wild-type hGH. For comparison with the structural epitope, the number of van der Waals contacts with receptor is also shown, derived from the crystal structure of the hGH(hGHbp)$_2$ complex.

| Variant | Number of van der Waals Contacts | $\dfrac{K_d(mut)}{K_d(pM)}$ | $K_d$ (hGH) |
|---|---|---|---|
| hGH(wild-type) | — | 340 | 1 |
| K41A | — | NE | NE |
| K41Q | 7 | 880 ± 84 | 2.6 |
| Y42A | 30 | 540 ± 80 | 1.6 |
| L45A | 7 | 3400 ± 330 | 10 |
| Q46A | 16 | 320 ± 20 | 0.9 |

(b) Design and analysis of random mutant libraries

Figure 7:
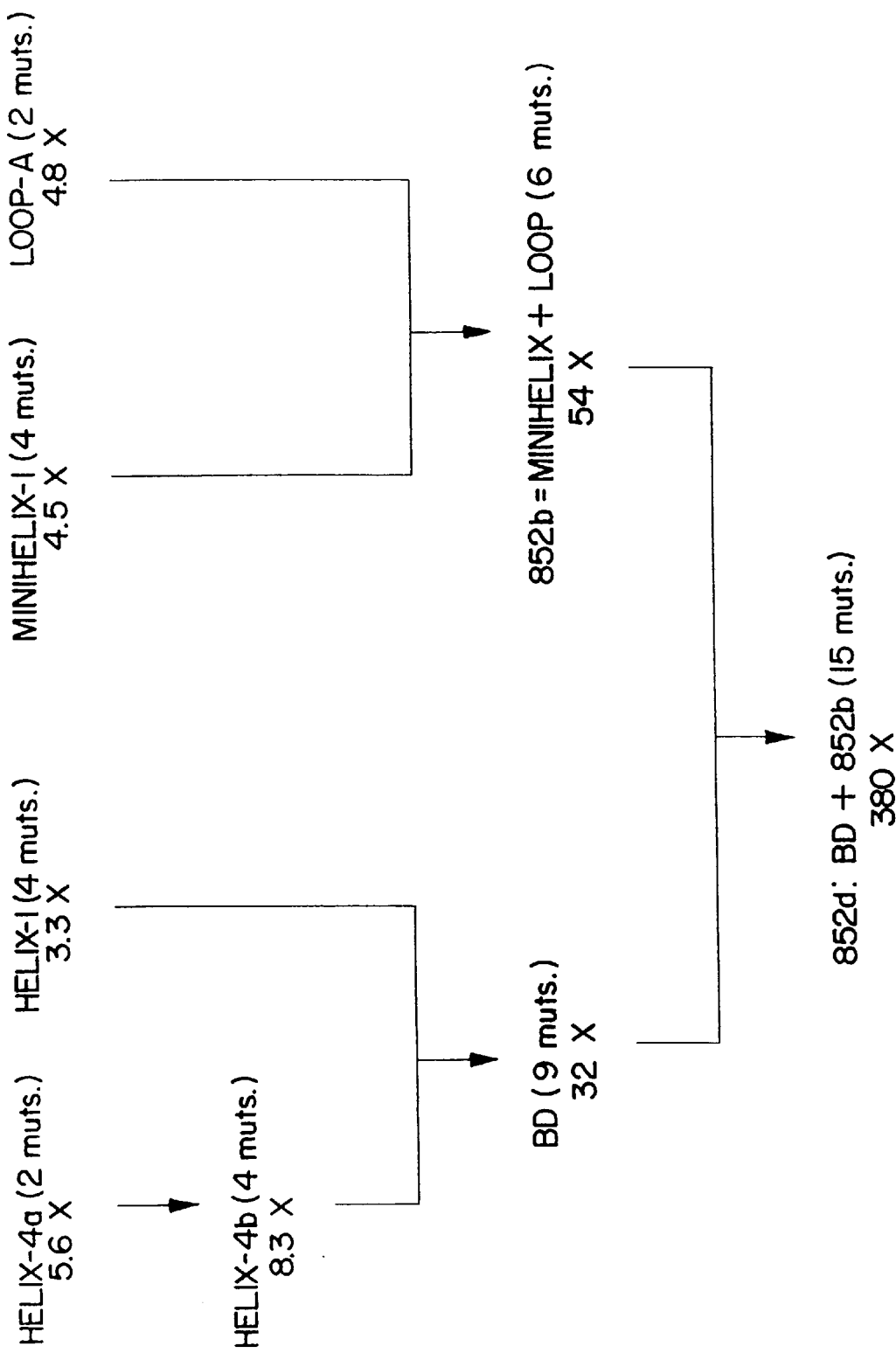
FIG. 7 shows the strategy for combining phage-derived mutations that enhance receptor binding affinity. The best selectants are shown with the fold increase in affinity over wild-type. The number of mutations from wild-type found in each of these variants is also shown (e.g., 4 muts.). Libraries randomized at four codons each in helix-1, helix-4, minihelix-1, or the loop connecting helices 1 and 2, were sorted separately. Two mutations (E174S/F176Y) identified in Helix-4a were used as background for additional randomization and selection at other helix-4 sites (Helix-4b; Lowman et al., supra). The mutations identified in Helix-1 and Helix-4b were combined to yield the BD variant; mutations in Minihelix-1 and Loop-A were combined to yield variant 852b. Finally, mutations from these two variants were combined to yield variant 852d.

Five separate libraries were sorted in which four residues within the structural and/or functional Site 1 epitope were randomized (FIG. 7). Restricting each library to 4 random codons allowed sampling of most of the possible variants (about $2 \times 10^5$ protein sequences generated from about $1 \times 10^6$ DNA sequences) within the limits of the library size (average of about $1 \times 10^7$ independent transformants).

Previously, a library (called Helix-4a) was produced in which residues K172, E174, F176 and R178 were randomized and displayed on monovalent phagemid particles. Lowman et al., *Biochemistry*, supra. After 3 cycles of binding selection, the tightest binding mutant (E174S, F176Y) had an affinity about 5-fold higher than wild-type hGH. These two mutants were fixed in a second library (called Helix-4b) in which R167, D171, T175, and I179 were randomly mutated in the E174S, F176Y background. After 6 rounds of selection a pentamutant (R167D, D171S, E174S, F176Y, I179T) was isolated that bound about 8-fold tighter than wild-type hGH. In a separate library (called Helix-1) residues F10, M14, H18 and H21 were randomly mutated. After 4 rounds of selection a tetramutant (F10A, M14W, H18D, H21N) was isolated that bound 3-fold tighter than wild-type hGH.

Here, the phage selection studies were expanded to the loop connecting helices 1 and 2. The four contact residues in Minihelix-1 (K41, Y42, L45 and Q46) were randomized and representative clones were sequenced after 2 to 7 rounds of binding selection (Table 4). Some residues were highly over-represented at given positions compared to what was expected from the frequency of those residues in the starting library. For example, about 35% of the clones contained a Q46W mutation. This was 7.6 standard deviation units above a random chance occurrence for Trp in the library. This is a good way to score the pool of selectants to establish a consensus sequence because it accounts for the expected codon bias and sampling statistics. By this criteria there was a mild preference for K41R, a slight preference for Y42R or Y42Q, a strong preference for L45W or L45 and a stronger preference for Q46W.

TABLE 4

Consensus residues identified after sorting hGH-phagemid libraries. The most frequently occurring residues from phage-displayed libraries are shown, based on fractional representation ($P_f$) among all sequenced clones after 2 to 7 rounds of binding selection. Expected frequencies ($P_e$) were calculated from the number of NNS codons for each amino acid theoretically in the starting library. Standard deviations ($\sigma_n$) were calculated as $\sigma_n = [P_e(1 - P_e)/n]^{1/2}$. Only residues for which the fraction found exceeded the fraction expected by at least $2\sigma_n$ are shown (i.e., $[(P_f - P_e)/\sigma_n] \geq 2$). For the Minihelix-1 library, n = 17 sequences; Loop-A library, n = 26; Combinatorial library (Helix-1), n = 68; Combinatorial library (Helix-4b), n = 56.

| Residue | | $P_e$ | $\sigma_n$ | $P_f$ | $\dfrac{P_f - P_e}{\sigma_n}$ |
|---|---|---|---|---|---|
| Minihelix-1: | | | | | |
| K41 | R | .094 | .071 | .35 | 3.7 |
|  | F | .031 | .042 | .12 | 2.0 |
| Y42 | R | .094 | .071 | .24 | 2.0 |
|  | Q | .031 | .042 | .18 | 2.0 |
| L45 | W | .031 | .042 | .24 | 4.8 |
|  | L | .094 | .071 | .41 | 4.5 |
| Q46 | W | .031 | .042 | .35 | 7.6 |
|  | F | .031 | .042 | .12 | 2.0 |
|  | Y | .031 | .042 | .12 | 2.0 |
| Loop-A: | | | | | |
| F54 | P | .062 | .047 | .73 | 14.1 |
| E56 | D | .031 | .034 | .19 | 4.7 |
|  | W | .031 | .034 | .19 | 4.7 |
|  | Y | .031 | .034 | .12 | 2.5 |
| I58 | I | .031 | .034 | .31 | 8.1 |
|  | V | .062 | .047 | .23 | 3.5 |
| R64 | K | .031 | .034 | .81 | 22.8 |
| Combinatorial (Helix-1): | | | | | |
| F10 | A | .062 | .03 | .41 | 12.0 |
|  | F | .031 | .02 | .25 | 10.4 |
|  | H | .031 | .02 | .16 | 6.2 |
| M14 | W | .031 | .02 | .26 | 11.1 |
|  | S | .094 | .04 | .26 | 4.8 |
|  | Y | .031 | .02 | .09 | 2.7 |
|  | N | .031 | .02 | .09 | 2.7 |
|  | H | .031 | .02 | .07 | 2.0 |
| H18 | D | .031 | .02 | .43 | 18.8 |
|  | F | .031 | .02 | .12 | 4.1 |
|  | N | .031 | .02 | .10 | 3.4 |
| H21 | N | .031 | .02 | .46 | 20.2 |
|  | H | .031 | .02 | .13 | 4.8 |
| Combinatorial (Helix-4b): | | | | | |
| R167 | N | .031 | .02 | .63 | 25.6 |
|  | K | .031 | .02 | .13 | 4.1 |
| D171 | S | .094 | .04 | .64 | 14.1 |
|  | D | .031 | .02 | .14 | 4.8 |
|  | N | .031 | .02 | .13 | 4.1 |
| T175 | T | .062 | .03 | 1.0 | 29.1 |
| I179 | T | .062 | .03 | .66 | 18.6 |
|  | N | .031 | .02 | .13 | 4.1 |

A second library (called Loop-A) was constructed in which F54, E56, I58 and R64 were randomly mutated. Alanine replacements caused a 4- to 20-fold reduction in affinity depending on the side-chain (FIG. 6A). Despite the fact that R64 is the only one of these residues that makes direct contact with the receptor (FIG. 6B), all positions showed a moderate to very strong preference for a particular residue that was usually different from the wild-type. R64K was the most preferred (found in 81% of the clones); it is known that R64K alone causes a ~3-fold improvement in binding affinity. Cunningham et al., *Science,* 247: 1461–1465 (1990). After this the order of preference went F54P>I58T>E56D or E56W.

The binding affinities for many of these mutants were analyzed by expressing the free hormone in a non-suppressor host that terminates translation at the amber codon at the end of hGH and the start of the geneIII domain. Lowman et al., *Biochemistry,* supra. Virtually every clone tested, between 3 to 7 rounds of binding selection from the Minihelix-1 library, had affinities greater than wild-type hGH (Table 5). The best was K41I, Y42H, L45W, Q46W, which was 4.5-fold improved in affinity over wild-type hGH. This DNA sequence is expected to occur randomly at a frequency of one in a million clones, which demonstrates the power of the affinity selection. Similar results were obtained from the Loop-A library with the best isolates being F54P, R64K and F54P, E56D, I58T, R64K, which are about 5-fold improved over wild-type hGH.

TABLE 5

Binding data for individual hGH clones mutated in (A) the Minihelix-1 or (B) Loop-A. Affinity constants were measured by competition binding to hGHbp versus $^{125}$I-labeled hGH. Wild-type hGH affinity is from Cunningham and Wells, 1989, supra. The fold increase in affinity over hGH for binding hGHbp is shown as the ratio $K_d$(hGH)/$K_d$(Mutant). Some clones were not analyzed (ND). Identical affinities were assumed for equivalent variants ($^\dagger$). Clones with spurious mutations (E65V$^\dagger$; S57Y$^\S$; N47Y$^\P$; P48S$^@$) are indicated.

A. Minihelix-1 library

| | Residue Position | | | | $K_d$ | $K_d$ (hGH)/ |
|---|---|---|---|---|---|---|
| Clone | 41 | 42 | 45 | 46 | (pM) | $K_d$ (mut) |
| hGH | K | Y | L | Q | 340 | 1 |
| 3 cycles | | | | | | |
| 833A.2 | V | S | L | W | 190 ± 26 | 1.8 |
| 833B.2 | L | R | L | W | 190 ± 23 | 1.8 |
| 833A.1 | F | R | L | Y | 160 ± 23 | 2.2 |
| 833B.1 | V | F | L | R | 150 ± 19 | 2.3 |
| 833A.4 | A | I | Q | W | ND | ND |
| 833B.4 | L | Y | V | R | ND | ND |
| 833B.3 | Y | W | G | Y | ND | ND |
| 833A.3 | F | L | V | L | ND | ND |
| 5 cycles | | | | | | |
| 835A.5 | G | T | W | T | 270 ± 80 | 1.3 |
| 835A.6 | I | H | W | W | 76 ± 29 | 4.5 |
| 835A.3 | R | R | L | F | ND | ND |
| 835A.7 | M | R | W | R | ND | ND$^\P$ |
| 835A.4 | R | T | A | V | ND | ND$^@$ |
| 7 cycles | | | | | | |
| 873B.5 | R | Q | L | W | 140 ± 20 | 2.4 |
| 873B.6 | R | Q | L | W | 140 ± 20 | 2.4$^\dagger$ |
| 873A.5 | R | T | A | V | ND | ND$^@$ |
| 873B.2 | R | S | W | F | ND | ND |
| consensus: | R | R | W | W | | |
| | Q | L | | | | |

B. Loop-A library

| | Residue Position | | | | $K_d$ | $K_d$ (hGH)/ |
|---|---|---|---|---|---|---|
| Clone | 54 | 56 | 58 | 64 | (pM) | $K_d$ (mut) |
| hGH | F | E | I | R | 340 | 1 |
| 3 cycles | | | | | | |
| 783B.4 | P | D | T | R | 210 ± 110 | 1.6 |
| 783B.7 | P | Y | I | K | 170 ± 30 | 2.0 |
| 783B.2 | H | W | L | K | 83 ± 25 | 4.2 |

TABLE 5-continued

Binding data for individual hGH clones mutated in (A) the Minihelix-1 or (B) Loop-A. Affinity constants were measured by competition binding to hGHbp versus $^{125}$I-labeled hGH. Wild-type hGH affinity is from Cunningham and Wells, 1989, supra. The fold increase in affinity over hGH for binding hGHbp is shown as the ratio $K_d$(hGH)/$K_d$(Mutant). Some clones were not analyzed (ND). Identical affinities were assumed for equivalent variants (†). Clones with spurious mutations (E65V†; S57Y§; N47Y¶; P48S@) are indicated.

| | | | | | | |
|---|---|---|---|---|---|---|
| 783A.4 4 cycles | M | R | L | K | ND | ND‡ |
| 786A.2 | G | W | V | R | 660 ± 140 | 0.50 |
| 786A.3 | F | W | V | R | 630 ± 120 | 0.53 |
| 786B.3 | S | H | L | K | 620 ± 120 | 0.56§ |
| 786B.6 | P | W | L | R | 520 ± 100 | 0.67 |
| 786A.6 | P | L | D | K | 460 ± 100 | 0.74 |
| 786B.5 | P | T | V | K | 250 ± 40 | 1.4 |
| 786B.2 | P | Y | I | K | 170 ± 30 | 2.0† |
| 786A.5 | P | L | Q | K | 120 ± 30 | 2.8 |
| 786A.4 | P | D | T | K | 61 ± 8 | 5.6 |
| 786A.1 | P | T | P | K | ND | ND |
| 786A.7 | P | A | L | K | ND | ND |
| 786B.7 6 cycles | P | C | I | K | ND | ND |
| 816B.6 | R | D | I | R | 350 ± 250 | 1.0 |
| 816B.4 | P | T | V | K | 250 ± 40 | 1.4† |
| 816B.1 | P | D | I | K | 180 ± 40 | 1.9 |
| 816B.2 | P | Y | I | K | 170 ± 30 | 2.0† |
| 816A.4 | P | E | I | K | 73 ± 16 | 4.8 |
| 816A.6 | P | E | I | K | 73 ± 16 | 4.8† |
| 816A.5 | P | D | T | K | 61 ± 8 | 5.6† |
| 816A.1 | E | W | V | K | ND | ND |
| 816A.2 | P | M | V | K | ND | ND |
| 816A.3 | P | L | Q | K | ND | ND |
| consensus: | P | D W | I | K | | |

(c) Improving affinity using additivity principles

According to additivity principles, mutations in non-interacting parts of a protein should combine to produce simple additive changes in the free energy of binding (Wells, 1990, supra). Therefore, it was sought to improve hGH binding through Site-1 by combining the substitutions isolated from phage-display libraries (FIG. 7). The three tightest-binding variants of hGH from the Helix-1 library (A=F10H, M14G, H18N, H21N, B=F10A, M14W, H18D, H21N, and C=M14S, H18F, H21L) were joined to each of the three tightest binding variants found in the Helix-4b library (D=R167N, D171S, E174S, F176Y, I179T, E=R167E, D171S, E174S, F176Y, and F=R167N, D171N, E174S, F176Y, I179T). All constructs were obtained in yields approaching that of wild-type hGH except for those containing variant A. Variant A and recombinants AD, AE, AF migrated as dimers (MW about 44 kDa) in non-reducing SDS-PAGE and as monomers (MW about 22 kDa) when reduced. Although these proteins did not contain an additional Cys residue, disulfide exchange could occur if they first formed non-covalent dimers. In fact, hGH is known to form a weak dimeric complex involving residues in helices 1 and 4. Cunningham et al., Science, 253, 1991, supra. Nevertheless, because these proteins formed disulfide dimers they were not pursued further. Variant C is also produced predominantly in disulfide dimer form too; however, the CD, CE, CF recombinants did not form a significant amount of dimer.

All the recombinants analyzed showed cumulative enhancements in affinity over the parental components (Table 6). The BD variant had the greatest affinity, which was 30-fold tighter than wild-type hGH. The tightest-binding variant from the Minihelix-1 library (K41I, Y42H, L45W, Q46W) and one of the tightest from the Loop-A library (F54P, R64K) were combined to produce the hexamutant, hGH 852b, whose affinity was about 40-fold higher than wild-type hGH. This was put together with the BD recombinant to yield the hGH variant, 852d, which bound about 400-fold tighter than wild-type hGH. Assuming simple additivity, it was expected that this variant would bind about 600-fold tighter than hGH from the product of the improvements in affinity by the individual components; this calculated value is reasonably close to the result. The 852d variant retained as wild-type only five of the 20 residues randomized (E56, I58, K172, T175, R178).

TABLE 6

Equilibrium binding constants of recombined hGH variants. Binding constants were measured by competitive displacement of either $^{125}$I-labeled wild-type hGH, BD, or 852d, using hGHbp and Mab5 (Cunningham and Wells, 1989, supra). The fold improvement in binding affinity is expressed as $K_d$(hGH)/$K_d$(variant). Some affinities (†) are from Lowman et al., Biochemistry, supra. Helix-1 variants are B = (F10A, M14W, H18D, H21N), and C = (M14S, H18F, H21L). Helix-4 variants are D = (R167N, D171S, E174S, F176Y, I179T), E = (R167E, D171S, E174S, F176Y), and F = (R167N, D171N, E174S, F176Y, I179T). BD, BF, CD, CE, CF represent combinations of these mutations. 852b = (K41I, Y42H, L45W, Q46W, F54P, R64K), and 852d = BD + 852b.

| Variant name | $K_d$ (pM) | $\frac{K_d(hGH)}{K_d(variant)}$ |
|---|---|---|
| hGH | 340 ± 50 | 1 |
| B' | 100 ± 30 | 3.4 |
| C' | 680 ± 190 | 0.5 |
| D' | 40 ± 20 | 8.5 |
| E' | 40 ± 20 | 8.5 |
| F' | 60 ± 30 | 5.7 |
| BD | 10 ± 3 | 34 |
| CD | 11 ± 3 | 31 |
| CE | 14 ± 8 | 24 |
| BF | 16 ± 5 | 21 |
| CF | 21 ± 11 | 16 |
| 852b | 7.9 ± 2.4 | 43 |
| 852d | 0.9 ± 0.3 | 380 |

(d) Combinatorial libraries of hGH

Despite the simple additivity found in combining mutants from libraries sorted independently, complex additivity has been observed for some neighboring substitutions (e.g., F176Y interacting with E174S). Lowman et al., Biochemistry, supra. Some side-chains mutated from helix 1 (F10, M14, H18, H21) can potentially contact those mutated in helix 4 (R167, D171, T175, and I179). Therefore, a combinatorial approach to sorting mutants derived from the Helix 1 and Helix-4b libraries (Huse et al., Science, 246: 1275–1281 [1989]; Clackson et al., Nature, 352: 624–628 [1991]) was investigated. Independent binding selections were carried out on the Helix-1 and Helix-4b libraries for 0, 2, or 4 cycles. DNA from the Helix-1 pool was ligated together with DNA from the Helix-4b library that was sorted for binding to the hGHbp for the same number of rounds. The three combinatorial libraries were then sorted an additional 2 to 7 cycles and 68 representative clones were sequenced (Table 7).

TABLE 7 hGH variants from hormone-phagemid binding selection of combinatorial libraries. All variants contain (E174S, F176Y), except for those with the wild-type Helix 4 sequence (-), which were non-recombinants. Libraries 707A, 707B and 707E, or 707C were sorted for 2 to 7 cycles for binding to hGHbp (see text). The numbers listed under P indicate the fractional occurrence among the sequenced clones. The numbers listed under # designate each independent isolate (e.g., pH0714A.1 is the first sequence). Some affinities are from Lowman et al., Biochemistry, supra; equivalent variants are assumed to have identical affinities ($^\dagger$). Several variants appeared as >10% disulfide dimers ($^\ddagger$). One clone contained an amber (TAG = Gln in SupE strains) codon ($^\S$), one contained a spurious mutation, E174N ($^\P$), and one ($^@$) contained two spurious mutations (L15R, K168R). Some variants were not expressed (NE) or not analyzed (ND).

| $K_d$ (p$\underline{M}$) | $K_d$ (hGH)/ $K_d$ (mut) | Clone | P | # | F10 | M14 | H18 | H21 | R167 | D171 | T175 | I179 |
|---|---|---|---|---|---|---|---|---|---|---|---|---|
| | | | | | Helix 1 | | | | Helix 4b | | | |

(A) Combinatorial of unselected libraries:
After 4 cycles (pH0714A; 5 sequences):

| $K_d$ (p$\underline{M}$) | $K_d$ (hGH)/$K_d$ (mut) | Clone | P | # | F10 | M14 | H18 | H21 | R167 | D171 | T175 | I179 |
|---|---|---|---|---|---|---|---|---|---|---|---|---|
| A | 0.60 | 1 | | | H | G | N | N | N | S | T | N | ND | |
| B | 0.40 | 4 | | | A | N | D | A | N | N | T | N | 50 ± 40 | 6.8$^{\dagger@}$ |

(B) Combinatorial of 2x-selected libraries:
After 2 cycles (pH0712B; 7 sequences):

| $K_d$ | $K_d$(hGH)/mut | Clone | P | # | F10 | M14 | H18 | H21 | R167 | D171 | T175 | I179 |
|---|---|---|---|---|---|---|---|---|---|---|---|---|
| A | 0.14 | | 1 | F | S | F | G | H | S | T | T | ND | |
| B | 0.14 | | 2 | H | Q | T | S | A | D | T | T | ND | |
| C | 0.14 | | 4 | H | G | N | N | N | A | T | T | ND | |
| D | 0.14 | | 5 | F | S | F | L | S | D | T | T | ND | |
| E | 0.14 | | 6 | A | S | T | N | — | — | — | — | ND | |
| F | 0.14 | | 7 | Q | Y | N | N | H | S | T | T | 74 ± 30 | 4.6 |
| G | 0.14 | | 6 | W | G | S | S | — | — | — | — | ND | |

After 2 cycles (pH0712E; 8 sequences):

| | | | | | | | | | | | | | |
|---|---|---|---|---|---|---|---|---|---|---|---|---|---|
| H | 0.13 | | 1 | F | L | S | S | K | N | T | V | ND | |
| I | 0.13 | | 2 | W | N | N | S | H | S | T | T | 160 ± 70 | 2.1 |
| J | 0.13 | | 3 | A | N | A | S | N | S | T | T | ND | |
| K | 0.13 | | 4 | P | S | D | N | — | — | — | — | ND | |
| L | 0.13 | | 5 | H | G | N | N | N | N | T | T | ND | |
| M | 0.13 | | 6 | F | S | T | G | — | — | — | — | ND | |
| N | C.13 | | 7 | M | T | S | N | Q | S | T | T | ND | |
| O | 0.13 | | 8 | F | S | F | L | T | S | T | T | ND | |

After 4 cycles (pH0714B; 6 sequences):

| | | | | | | | | | | | | | |
|---|---|---|---|---|---|---|---|---|---|---|---|---|---|
| A | 0.17 | | 1 | A | W | D | N | — | — | — | — | 100 ± 30 | 3.3$^\dagger$ |
| B | 0.17 | | 2 | A | W | D | N | H | S | T | N | ND | |
| C | 0.17 | | 3 | M | Q | M | N | N | S | T | T | NE$^\S$ | |
| D | 0.17 | | 4 | H | Y | D | H | R | D | T | T | ND | |
| E | 0.17 | | 5 | L | N | S | H | — | — | — | — | 820 ± 200 | 0.4$^\dagger$ |
| F | 0.17 | | 6 | L | N | S | H | T | S | T | T | 34 ± 19 | |

After 6 cycles (pH0716B; 8 sequences):

| | | | | | | | | | | | | | |
|---|---|---|---|---|---|---|---|---|---|---|---|---|---|
| A | 0.38 | | 2 | A | W | D | N | — | — | — | — | 100 ± 30 | 3.3$^\dagger$ |
| B | 0.13 | | 4 | A | W | D | N | N | S | T | S | ND | |
| C | 0.13 | | 7 | A | W | D | N | K | D | T | T | ND | |
| D | 0.13 | | 1 | A | T | S | N | N | S | T | T | ND | |
| E | 0.13 | | 3 | M | A | D | N | N | S | T | T | 68 ± 46 | 5.0$^{\ddagger\dagger}$ |
| F | 0.13 | | 5 | H | Y | D | H | N | S | T | T | ND | |

(pH0716E; 8 sequences):

| | | | | | | | | | | | | | |
|---|---|---|---|---|---|---|---|---|---|---|---|---|---|
| G | 0.38 | | 1 | A | H | A | S | N | S | T | T | ND | |
| H | 0.25 | | 7 | F | S | L | A | N | S | T | I | ND | |
| I | 0.13 | | 3 | H | Y | D | H | Y | S | T | S | ND | |
| J | 0.13 | | 4 | V | L | D | H | N | S | T | T | ND | |
| K | 0.13 | | 6 | A | W | D | N | N | N | T | I | ND$^\P$ | |

After 7 cycles (pH0717B; 12 sequences):

| | | | | | | | | | | | | | |
|---|---|---|---|---|---|---|---|---|---|---|---|---|---|
| A | 0.33 | | 1 | A | W | D | N | N | A | T | T | 12 ± 6 | 28 |
| B | 0.17 | | 6 | A | W | D | N | — | — | — | — | 100 ± 30 | 3.3$^\dagger$ |
| C | 0.08 | | 11 | A | W | D | N | N | S | T | N | ND | |
| D | 0.06 | | 13 | A | W | D | N | R | N | T | T | ND | |
| E | 0.08 | | 14 | A | W | D | N | K | S | T | S | ND | |
| F | 0.08 | | 2 | F | S | T | G | — | — | — | — | ND | |
| G | 0.08 | | 7 | I | Q | E | H | N | S | T | T | 16 ± 10 | 21 |
| H | 0.08 | | 15 | H | Y | D | H | N | S | T | T | ND | |

(pH0717E; 8 sequences):

| | | | | | | | | | | | | | |
|---|---|---|---|---|---|---|---|---|---|---|---|---|---|
| I | 0.50 | | 1 | F | S | L | A | N | S | T | V | 32 ± 5 | 11 |
| J | 0.25 | | 13 | A | H | A | S | N | T | T | T | ND | |
| K | 0.13 | | 14 | A | W | D | N | A | N | T | T | ND | |
| L | 0.13 | | 11 | H | Y | D | H | Y | S | T | S | ND | |

TABLE 7-continued hGH variants from hormone-phagemid binding selection of combinatorial libraries. All variants contain (E174S, F176Y), except for those with the wild-type Helix 4 sequence (-), which were non-recombinants. Libraries 707A, 707B and 707E, or 707C were sorted for 2 to 7 cycles for binding to hGHbp (see text). The numbers listed under P indicate the fractional occurrence among the sequenced clones. The numbers listed under # designate each independent isolate (e.g., pH0714A.1 is the first sequence). Some affinities are from Lowman et al., Biochemistry, supra; equivalent variants are assumed to have identical affinities (†). Several variants appeared as >10% disulfide dimers (‡). One clone contained an amber (TAG = Gln in SupE strains) codon (§), one contained a spurious mutation, E174N (¶), and one (@) contained two spurious mutations (L15R, K168R). Some variants were not expressed (NE) or not analyzed (ND).

| $K_d$ (p$\underline{M}$) | $K_d$ (hGH)/ $K_d$ (mut) | Clone | P | # | Helix 1 | | | | Helix 4b | | | |
|---|---|---|---|---|---|---|---|---|---|---|---|---|
| | | | | | F10 | M14 | H18 | H21 | R167 | D171 | T175 | I179 |
| | | | | Combinatorial of 4x-selected libraries: After 4 cycles (pH0714C; 6 sequences): | | | | | | | | |
| A | 0.67 | 2 | F | S | F | L | K | D | T | T | 150 ± 70 | 2.3† |
| B | 0.17 | 1 | F | S | F | L | N | S | T | T | 11 ± 3 | 31† |
| C | 0.17 | 5 | M | A | D | N | N | S | T | T | 68 ± 46 | 5.0‡† |

Overall, the highest affinity variants isolated from any of these three combinatorial sorts resembled those previously isolated by independent sorting of the Helix-1 and Helix-4b libraries. Lowman et al., *Biochemistry*, supra. For example, the highest affinity mutants isolated previously from the Helix-1 library were F10A, M14W, H18D, H21N (Helix-1.B) and F10H, M14G, H18N, H21N (Helix-1.A); these bound about 3.3-fold and 2.4-fold tighter than wild-type hGH, respectively. The Helix 1.A sequence was recovered in 60% of the clones from Combinatorial Library A, and in 13% of the clones isolated in early rounds of sorting from Combinatorial Library B. The Helix-1.B sequence predominated in later rounds of sorting the Combinatorial Library B. Most of these were independent clones (not siblings or contaminants), because they had different DNA sequences and usually differed in the mutants selected in helix 4.

Similar results were obtained with selectants in helix 4. When the Helix-4b library was independently sorted, a number of sequences were obtained containing R167N, D171S or N, T175 (conserved), and I179T. Lowman et al., *Biochemistry*, supra. These were the same residues that tended to be selected in Combinatorial Libraries A, B and C. In fact, one of the best mutants previously isolated (R167N, D171S, T175, I179T) was commonly isolated by combinatorial sorting and predominated especially in the later rounds.

Some sequences sorted by combinatorial means were very different from ones selected from the two independent libraries; but this could arise for statistical reasons. For example, the Helix-1 and Helix-4b libraries contain about $10^6$ different DNA sequences, and if combined (without pre-selection) would contain $10^{12}$ possible combinations. Transformation efficiencies limit the sampling size to less than or equal to ~$10^7$ independent clones. Thus, the selection of the same sequences is remarkable given the high diversity of sequences possible in these libraries and the mild improvements in affinity being selected for.

The affinities for a number of these isolates were measured (Table 7). All had improved binding affinity (2- to 29-fold) compared to wild-type hGH. Most were improved over E174S, F176Y, which was present in all the starting clones, and independently caused a 5.6-fold increase in affinity over wild-type hGH. Lowman et al., *Biochemistry*, supra. The highest affinity variants were generally isolated from later rounds of sorting and were highly abundant in those pools. For example, the highest affinity mutant tested was clone 717B.1, which was isolated after seven rounds of sorting of Combinatorial Library B. This isolate represented a third of the clones in that pool. Remarkably, this clone is identical to the BD variant (Table 6), except that instead of D171S it contained the conservative substitution, D171A. Not surprisingly, the 717B.1 and BD variants bound with comparable affinities (12 pM and 10 pM, respectively). These data indicate that combinatorial and additive strategies yield comparable solutions for successful optimization of affinity.

(e) Testing the importance of individual side-chains in affinity maturation

The contribution of some of the phage-improved residues to the binding affinity was evaluated by introducing them into wild-type hGH, or by converting them back to the wild-type residue in the affinity-matured BD variant (Table 8). The K41I, Y42H, L45W, Q46W variant bound 4.5-fold tighter than wild-type hGH. Each of the single mutants in hGH caused 1.7- to 2.5-fold reductions in affinity. This indicates that the combination of mutations at this site is critical for the affinity improvements. These residues lie on adjacent positions on one face of the minihelix-1.

TABLE 8

Testing the contributions of individual side-chains identified by phage display. Receptor binding affinities of variants were measured by BIAcore ™ (†) or by RIA (unmarked) and normalized to the RIA value for hGH as determined by cunningham and Wells, 1989, supra. Point mutations were made to test the contributions of individual side-chains found after phage sorting. The fold decrease in affinity is expressed as $K_d$ (revertant)/$K_d$(parent), where parent is the background used for mutagenesis.

| Point mutants in wild-type background: | | |
|---|---|---|
| | $k_d$ (p$\underline{M}$) | $K_d$(mut)/$K_d$(hGH) |
| hGH(wild-type) | 340 ± 50 | 1 |
| †K41I | 580 ± 140 | 1.7 |
| †Y42H | 860 ± 50 | 2.5 |
| †L45W | 722 ± 60 | 2.1 |
| †Q46W | 780 ± 100 | 2.3 |

TABLE 8-continued

Testing the contributions of individual side-chains identified by phage display. Receptor binding affinities of variants were measured by BIAcore ™ (†) or by RIA (unmarked) and normalized to the RIA value for hGH as determined by cunningham and Wells, 1989, supra. Point mutations were made to test the contributions of individual side-chains found after phage sorting. The fold decrease in affinity is expressed as $K_d$ (revertant)/$K_d$(parent), where parent is the background used for mutagenesis.

Revertants in BD background:

|  | $k_d$ (pM) | $\frac{K_d(mut)}{K_d(BD)}$ |
|---|---|---|
| BD | 10 ± 3 | 1 |
| D18H, N21H | 12 ± 9 | 1.1 |
| A10F, W14M | 13 ± 5 | 1.2 |
| †A10F | 13 ± 4 | 1.3 |
| N167R, S171D | 17 ± 8 | 1.6 |
| T179I | 18 ± 9 | 1.7 |
| Y176F | 49 ± 21 | 4.6 |

Affinity improvements caused by substitutions in the BD variant were tested by mutating them back to the wild-type residue either individually or in pairs (when the residues were adjacent) (Table 8). This showed that seven of the nine substitutions contribute only very subtle improvements in binding (1.1 to 1.7-fold). Even the most dominant effect, F176Y, imparts only a 4.6-fold improvement in binding. Nonetheless, the product of these effects in the octamutant, F10A, M14W, H18D, H21N, R167N, D171S, F176Y, I179T, predicted a 16-fold improvement in affinity versus wild-type hGH This compares to the 34-fold enhancement measured for the BD variant that contains in addition E174S.

(f) Effects of affinity maturation on the kinetics of binding

In Example I, the BIAcore™ biosensor device was used to measure the kinetics of binding for alanine mutants produced at residues in hGH that become buried at Site 1 upon receptor binding. For a better understanding of the molecular basis for affinity improvements selected here, the BIAcore™ biosensor was used to measure their kinetics of binding to the hGHbp (Table 9). In general, as the affinity from wild-type hGH was increased, the off-rate decreased with little change in on-rate. In fact, in going from wild-type to the highest affinity mutant, 852d, there was a >60-fold decrease in the off-rate and only a 4-fold increase in the on-rate. (The off-rate was too slow to measure accurately, but if it was calculated from the $K_d$ measured by RIA and the on-rate, the off-rate would be 100-fold slower than wild-type hGH.) The hGH binding site had previously been recruited into a homolog of hGH, human placental lactogen (hPL). This differs in sequence by 15% from hGH and binds ~2000-fold weaker. Lowman et al., *J. Biol. Chem.*, supra. The recruited hPL variant has kinetic parameters for binding that are similar to hGH (Table 9). Like the affinity-matured hGH variant, this mutant shows much larger improvements in off-rate (~100-fold) compared to on-rate (about 10-fold) relative to wild-type hPL. The fact that off-rate is most affected among the phage selectants indicates that the sorting was performed under conditions approaching equilibrium.

TABLE 9

Binding kinetics of hGH variants. BIAcore ™ biosensor measurements were carried out with immobilized hGHbp(S201C) in PBS buffer + 0.05% Tween-20. The BIAcore ™ biosensor $K_d$ is calculated from $k_{off}/k_{on}$, except for hPL, for which $k_{on}$ and $K_d$ were measured and $k_{off}$ was calculated (†). The ratio of $K_d$'s indicates the fold increase in binding affinity vs. wt-hGH according to the BIAcore ™ biosensor data. Mutant combinations in hGH are designated by Roman numerals. The hPL (0274) contains V4I, D56E, M64R, E174A, M179I.

| Mutant | $K_{on}/10^4$ $M^{-1}s^{-1}$ | $k_{off}/10^{-5}$ $s^{-1}$ | $K_d$ (nM) | $\frac{K_d(hGH)}{K_d(mut)}$ |
|---|---|---|---|---|
| hPL | 3.2 | 6000† | 1800 | 0.0006 |
| hPL(0274) | 43 | 49 | 1.1 | 0.79 |
| hGH (822a1) {10Y, 14E, 18R, 21G} | 40 | 53 | 1.3 | 0.93 |
| hGH | 24 | 34 | 1.4 | 1 |
| I. hGH (835a6) {41I, 42H, 45W, 46W} | 13 | 6.9 | 0.52 | 2.7 |
| II. hGH {816a4} {54P, 64K} | 21 | 6.6 | 0.31 | 4.5 |
| III. hGH (852b) {I + II} | 36 | 5.1 | 0.14 | 10 |
| IV. hGH (BD) | 20 | 3.0 | 0.15 | 9.3 |
| hGH (852d) {III + IV} | 98 | ≤0.6 | ≤0.006 | ≥230 |

Conclusion

Regions of hGH were randomly mutated that were thought to be important either because they were in contact with the receptor or because when converted to alanine they affected binding affinity. Thus, an average random mutant from these libraries should be dramatically reduced in binding affinity from wild-type hGH. Yet after only a few rounds of selection, isolates bound with similar and often higher affinity than wild-type hGH. The clones isolated usually exhibited consensus sequences that were different from the wild-type (Table 4).

Very small improvements in affinity led to rapid and almost exclusive convergence in these libraries. For example, the R64K mutant separately binds only about 3-times tighter than wild-type hGH (Cunningham et al., 1990, supra). Yet after just three cycles of binding selection R64K dominated the library (Table 5). Similarly, I179T contributed only a 1.7-fold improvement in affinity (Table 8). However, when sorted separately in the Helix-4b library of Lowman and Wells, supra, or combinatorially with mutants in Helix 1 (Tables 4 and 7) it was found that I179T was almost exclusively selected. Strong selection for these subtle improvements in affinity emphasizes the power of this technique for rescuing the highest affinity variants in the pool.

Not all variants are displayed on the phage (see Wells and Lowman, *Current Opinion in Struct. Biol.*, 2: 597–604 [1992]). This is because mutants that are misfolded or unstable can be either digested by proteases, aggregated, or blocked in secretion or assembly on phage. Although there does not appear to be a strong bias against particular DNA sequences, there is a clear selection against Cys-containing mutants, which selection has been previously noted for hGH mutants (Lowman and Wells, supra). The number of codons simultaneously mutated was deliberately limited to four (about $10^6$ DNA sequences) so that there would be a good chance of having each represented in the starting pool of phagemids (about $10^7$ independent transformants).

Less than half of the side-chains that become buried at Site 1 by the first receptor significantly affect binding affinity when converted to alanine [Example I, FIG. 1A]. The minihelix-1 contact residues provide a good example of this.(Table 3). The Y42 and Q46 side-chains make more van der Waals contacts and undergo more burial alone than K41 and L45 combined. Yet, Y42A and Q46A have almost no effect upon binding compared to the mutations at K41 and L45.

Figure 8A:
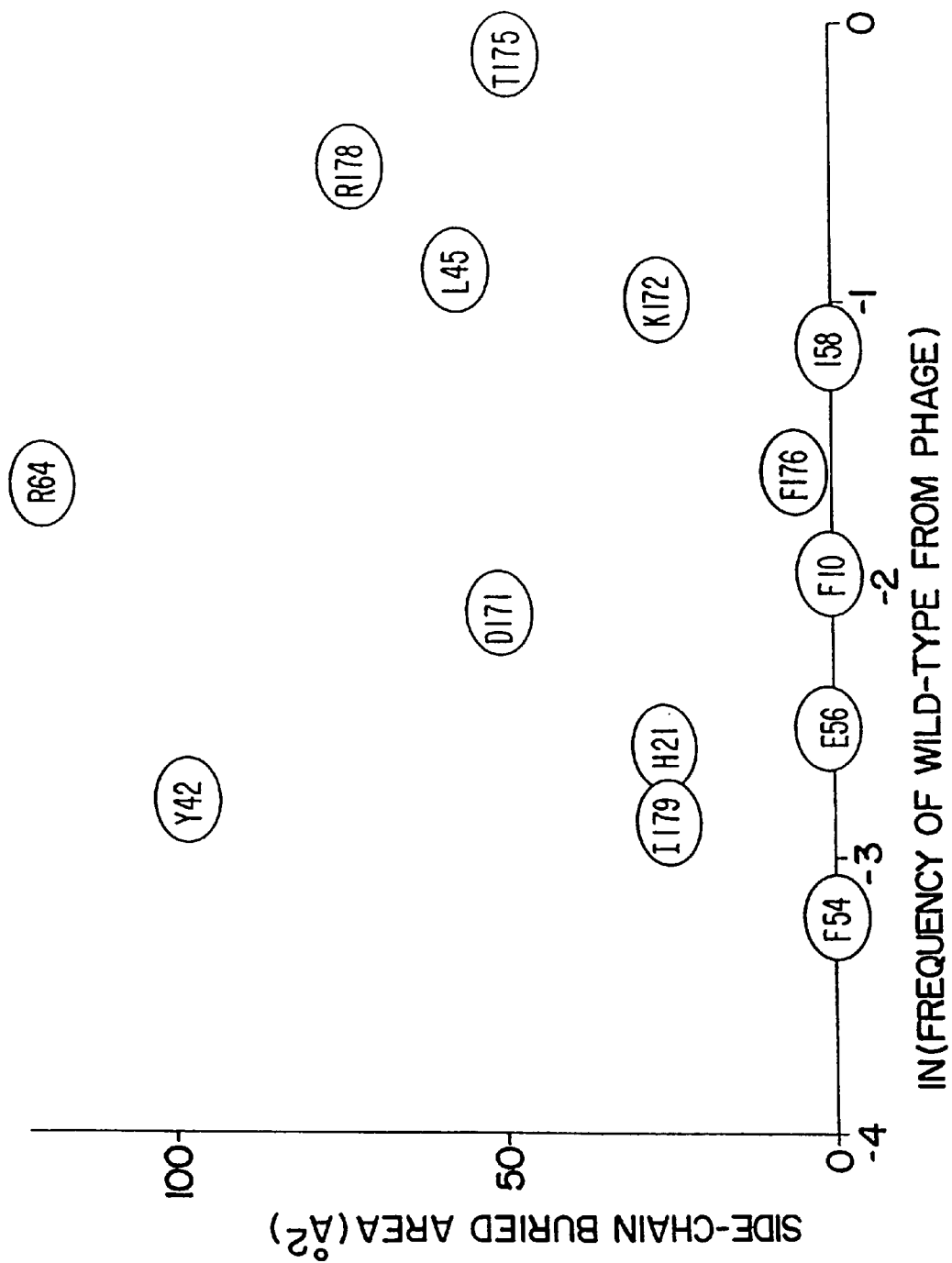
Figure 8B:
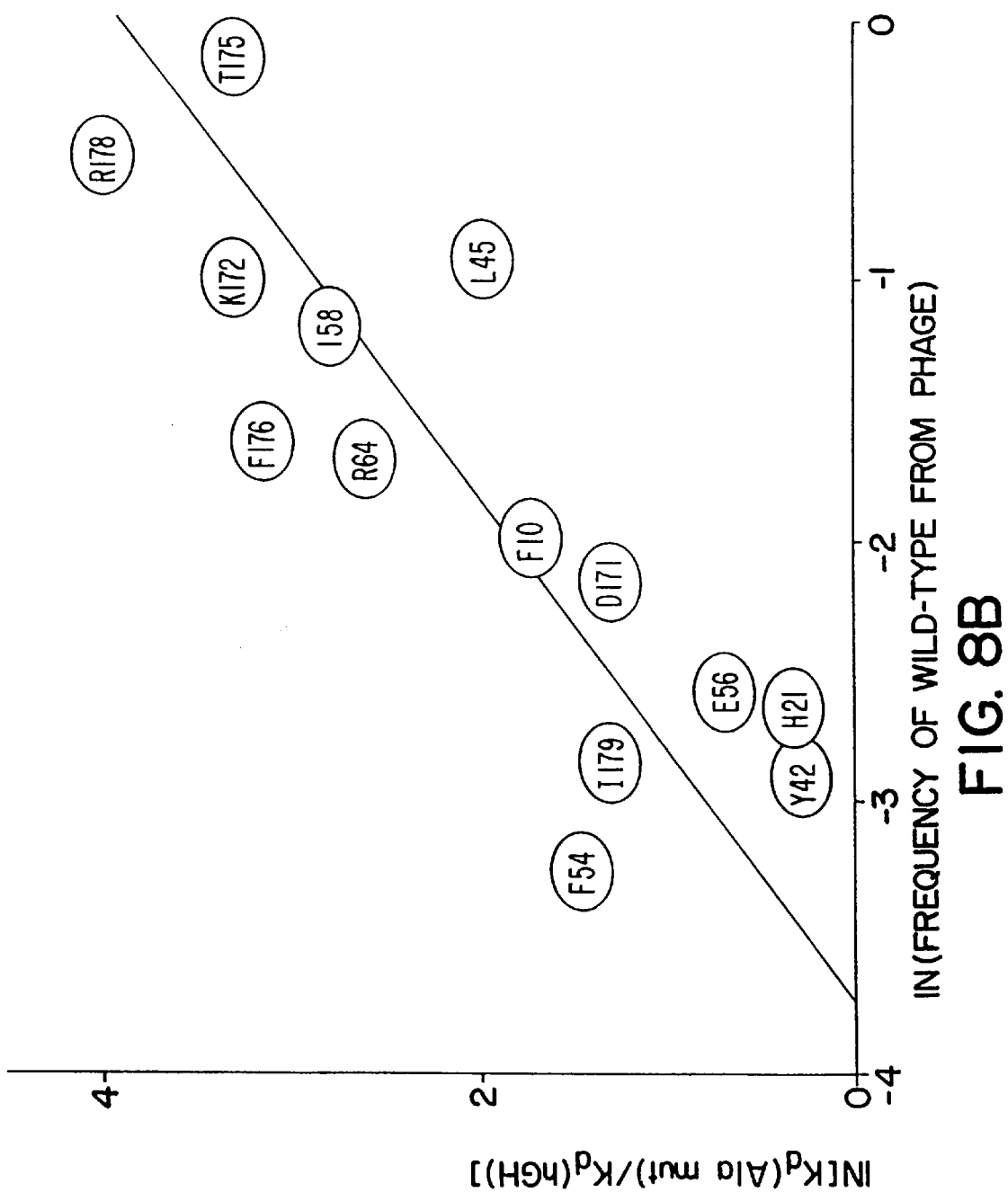
Figure 9:
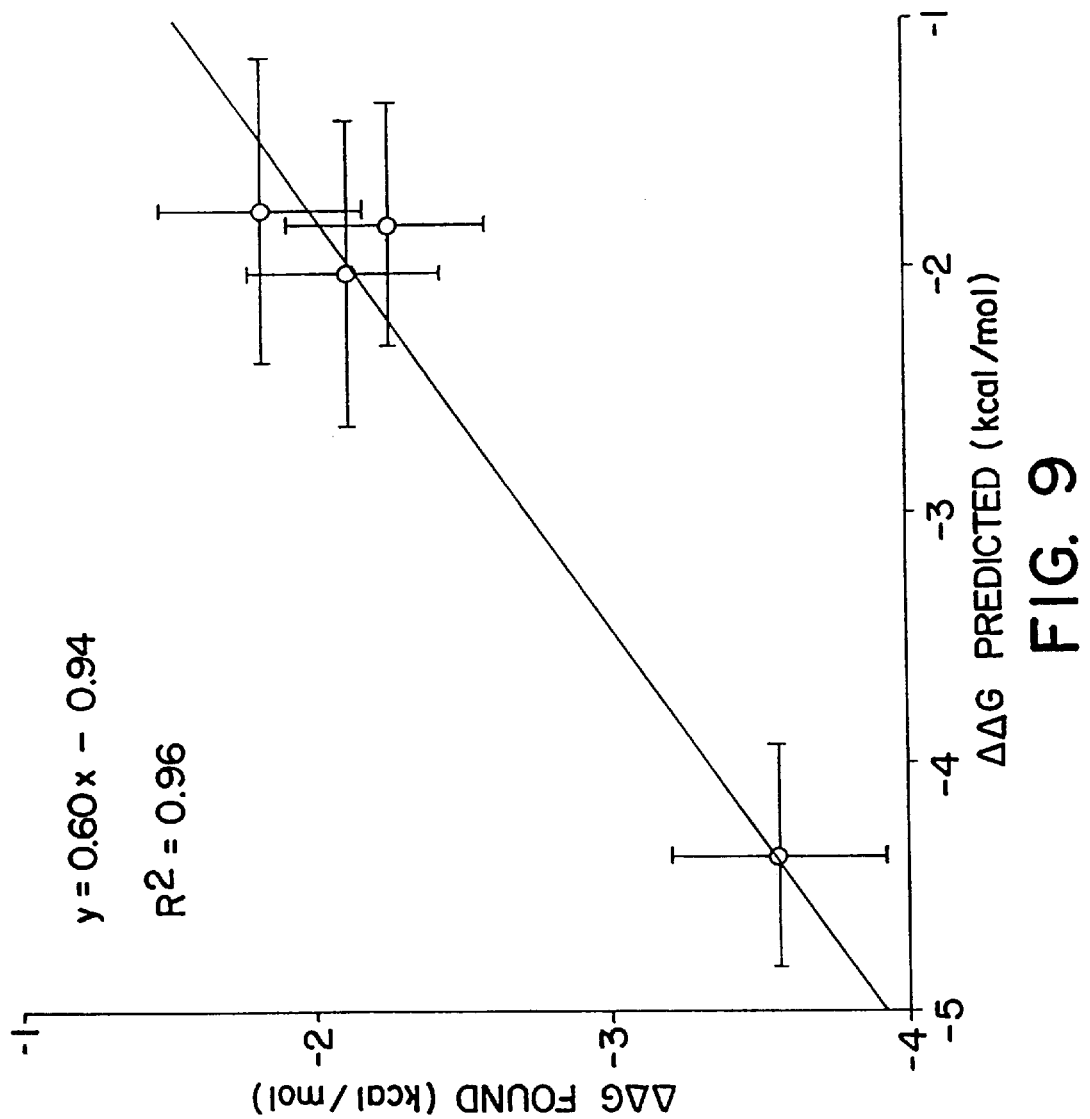
FIG. 9 discloses the additivity of phage-derived mutations. The change ($\Delta\Delta G$) in free energy of binding versus that of wild-type hGH was compared with the sum of $\Delta\Delta G$ for component mutations. The points shown correspond to the combinations of (1) variant BD vs. [B plus D]; (2) variant 852b vs. [minihelix-1 plus loop-A]; (3) variant BF vs. [B plus F]; and (4) variant 852d vs. [BD plus 852b]. Error bars were estimated from standard deviations using a propagation of errors calculation. Bevington, *Data Reduction and Error Analysis for the Physical Sciences*, pp. 56–65 (McGraw-Hill, New York, 1969). The line shown is y=−0.94+0.60x; R$^2$=0.96.

These studies indicate that functionality is not easily assessed by the extent to which a side-chain makes contact with the receptor. Another way to evaluate this is to correlate the conservation of wild-type residues after binding selection with the extent to which they are buried by the receptor. As shown in FIG. 8A, overall there is essentially no correlation ($R^2$=0.022) with the conservation of wild-type residues from phagemid libraries. This is also evident by comparing FIG. 6B and FIG. 6C. However, the three most conserved side-chains (T175, R178, L45) all have substantial contact with receptor.

There is a reasonable correlation ($R^2$=0.71) between the reduction in affinity as assessed by alanine-scanning mutagenesis and side-chain conservation following phage sorting (FIG. 8B; compare FIG. 6A and FIG. 6C). A roughly linear correspondence is seen (y=3.9+1.0 x). If data from the Combinatorial libraries are included, R167 is added, and the correlation falls to 0.65. The trend for functional importance versus conservation argues for considering functional information for choosing residues to randomize over considerations of structure (FIG. 8A).

These data indicate that functionality determined by alanine-scanning mutagenesis is similar to that determined by sequence conservation after binding selection. However, there is no correlation ($R^2$=0.005) between the frequency of conservation of given residues among natural variant growth hormones and conservation following binding selection from phage-display libraries (FIG. 8C). In nature the functional constraints on growth hormone are not fixed as they are by the in vitro binding selection.

Many of the selected residues at functionally important and highly buried sites, either at the interface or in the hormone itself, tend to be retained as the wild-type residue or a close homolog. For example, all five of the residues that are most conserved as the wild-type after extensive phage sorting (E56, I58, K172, T175, and R178) are completely buried in the complex; converting them to alanine caused 4- to 60-fold reductions in affinity (Cunningham and Wells, 1989, supra). When substitutions were tolerated at these positions they were typically similar to the wild-type residue. For example, the highest affinity selectants contained either Asp or Glu at position 56, beta-branched residues at position 58, Lys or Arg at 172, Thr or Ser at 175, and Lys or Arg at 178 (Table 5; Lowman et al., *Biochemistry,* supra).

There is another group of functionally important residues that become highly buried upon receptor binding (K41, L45, R64, D171 and I179). When these were randomized, improved substitutes were found that tended to be similar in character to the wild-type residue. For example, K41 was often replaced with Arg; L45 was substituted with large hydrophobic side-chains; R64 was most frequently substituted by Lys; D171 was optimally replaced by Asn and sometimes Ser; I179 was usually substituted by β-branched residues (Tables 4, 5, and 7; Lowman et al., *Biochemistry,* supra). Thus, improvements can be made at functionally important residues buried at the interface—they tend to be toward an isosteric side-chain or one of similar chemical character.

Two of the residues that were randomized (H18 and E174) had enhanced binding affinity when converted to alanine and were completely buried in the complex. These almost always sorted to something smaller than the wild-type residue. For example, the preferred substitution for H18 was Asp or Asn, and for E174 was Ala, Ser or Thr. Lowman et al., *Biochemistry,* supra. The packing at these positions, called hindrance determinants, is energetically unfavorable.

Another class of residues (H21, Y42, Q46 and R167) are highly buried at the interface but have little or no effect on binding affinity when converted to alanine. These residues rarely sort back to the wild-type residue. For example, H21 tended to sort to Asn; Y42 often came back as Arg or Gln; Q46 preferred Trp, and R167 often sorted to Asn (Tables 4, 5, and 7; Lowman et al., *Biochemistry,* supra). Despite the consensus found at these buried residues the affinity enhancements made from them were very small (Table 8). Thus, it appeared more difficult to obtain improvements in affinity from contact residues that were functionally inert.

The last group of residues (F10, M14, and F54) are virtually buried in the folded hormone and affect binding affinity by 2- to 4-fold when converted to alanine, presumably by indirect structural effects. Surprisingly, radical substitutions were tolerated here that show consensus sorting (Tables 4, 5, and 7; Lowman et al., *Biochemistry,* supra). For example, F54P was almost the sole solution in the Loop-A library. Phe 54 is 84% buried in the hormone and 10 Å away from making contact with the receptor. It is estimated that the F54P mutant enhances affinity by a factor of about 1.6 fold based on the fact that the double mutant (F54P, R64K) is improved in binding by 4.8 fold (Table 5), and the R64K mutant alone enhances binding by a factor of ~3 (Cunningham et al., 1991, supra). Residues 10 and 14 tend to co-vary, which is not surprising given their adjacent positions along helix 1. In general, the sum of the volumes of these two side-chains in the selectants tended to be the same or smaller than F10 plus M14. This is consistent with their tightly packed arrangement.

Although it is possible to rationalize the general features of these mutants by combining the functional and structural data, there are always unusual mutants that come through the sorting. For example, I179 was almost always conservatively replaced by a β-branched side-chain (especially Ile or Thr), but I179S also appeared (Table 7). Similarly, L45 was almost always replaced by a large side-chain (Leu or Trp), but L45A was also found (Table 5). Provided they are able to fold, such variants can be expected to persist through many rounds of selection at a background level, even though they can fail to improve or can even weaken binding affinity.

These studies indicate guidelines for affinity maturation of binding interfaces using monovalent phage display. A starting point toward efficient optimization of affinity is a complete alanine scan of the relevant interface. One cannot easily search more than 5 or 6 codons exhaustively (Lowman and Wells, supra); therefore, the library needs to be focused on residues where one can hope to improve affinity. It is also possible to limit the codon choices (see, e.g., Arkin and Youvan, *Bio/Technology,* 10: 297–300 [1992]), but this makes assumptions about what can or can not be useful substitutions. This is more reasonable to do if one has detailed knowledge of the structural interface a priori.

The residues whose the most obvious improvements in affinity occurred were those that were shown by alanine-scanning mutagenesis to most affect binding. For example, the largest improvements in affinity came from R64K, E174S, and F176Y. E174A was known to enhance affinity, but R64A and F176A caused large reductions in affinity. Thus, despite the fact that the most highly conserved residues in the phage sorting were those that were most important by alanine-scanning mutagenesis, there were still-improved variants to be found.

The functional data can be more important for targeting residues for optimization than the structural data. For example, several residues that are not in contact with the receptor (F10, M14, and F54), but affected binding when converted to alanine, produced affinity enhancements when randomly mutated. Moreover, some residues in contact with the receptor, but of little functional significance by alanine-scanning mutagenesis (Y42, Q46), failed to improve affinity when phage mutations were examined as point mutations (Table 8).

Ideally, one should randomize residues that can contact each other in the same mutagenesis step so that they are allowed to co-vary. Co-variance was seen in the Helix-1, Minihelix-1, and Helix 4a libraries when residues were close enough to interact. Sorting libraries by combinatorial means is especially useful in situations where mutations can lead to complex additive effects. For example, if side-chain replacements cause large conformational changes, as they can in flexible loops in antibodies, combinatorial sorting would allow for improvements by searching randomly for the best combinations of mutant heavy and light chains. Huse et al., supra; Clackson et al., supra; Collet et al., *Proc. Natl. Acad. Sci. USA*, 89: 10026–10030 (1992).

Nonetheless, improvements in hGH tended to occur by simple additive effects both between libraries and within libraries and even when the side-chains can interact. Practically, this means that one can randomize many residues independently and combine them in the end to obtain high-affinity variants. Fundamentally, it indicates that the interactions between side-chains, even neighboring ones, often have little effect, or can be compensated for without significant effect, on the free energy of binding receptor. See also, Lowman and Wells, *J. Mol. Biol.*, 234:564–578 (1993), which is hereby incorporated by reference in its entirety.

EXAMPLE III

The B2036 Variant

A further variant GH polypeptide was constructed with the intent of reducing potential immunogenicity by limiting the number of substituted residues in the polypeptide, yet maintaining enhanced binding affinity at site 1. A second goal of this experiment was to limit the number of lysine residues occurring in the molecule, especially occurring at sites important in the binding of GH to its receptor, thereby rendering the variant a better candidate for modification with polyethylene glycol ("pegylation"), while preserving enhanced affinity of the variant for its receptor.

Thus, using the data described above for the generation of the "supermutant" 852d, a further variant, B2036, was constructed using the techniques described above. 852d has the following substitutions:

F10A, M14W, H18D, H21N, K41I, Y42H, L45W, Q46W, F54P, R64K, R167N, D171S, E174S, F176Y, I179T.

In contrast, the variant constructed (B2036) here has the following substitutions:

H18D, H21N, G120K, R167N, K168A, D171S, K172R, E174S, I179T.

The G120K substitution was added to generate a better antagonist candidate, although other substitutions at that position are acceptable. Any amino acid can be substituted at G120 to generate an antagonist; more preferably, the substitution is lysine, arginine, tryptophan, tyrosine, phenylalanine, or glutamate. The R64K substitution was omitted so as to protect site I binding residues from pegylation. Similarly, the K168A and the K172R substitutions were added to B2036 to reduce the number of sites available for pegylation at the hormone-receptor site I binding interface. In contrast, the G120K substitution makes available an additional lysine for pegylation while providing an effective site 2 block.

The remaining substitutions in 852d were omitted from the construction of B2036 to reduce possible antigenicity of the variant in humans. Although some reduction in affinity is expected in comparison to 852d, the expected affinity of B2036 for its receptor is still substantially greater than wild type and is desirable for use as an antagonist.

It is expected that B2036 could be further modified by restoring the glycine at residue 120, thereby generating a candidate for use as an agonist that is expected to have reduced antigenicity in humans in comparison with 852d. Similarly, such a candidate would be more optimally pegylated, as the number of lysine residues within the site I interface is decreased in comparison with the "supermutant".

EXAMPLE IV

The B2024 Variant

A further variant GH polypeptide was constructed with the intent of reducing potential immunogenicity by limiting the number of substituted residues in the polypeptide, yet maintaining enhanced binding affinity at site 1. A second goal of this experiment was to limit the number of lysine residues occurring in the molecule, especially occurring at sites important in the binding of GH to its receptor, thereby rendering the variant a better candidate for modification with polyethylene glycol ("pegylation"), while preserving enhanced affinity of the variant for its receptor.

Thus, alanine mutations were combined by site-directed mutagenesis to produce a growth hormone variant having a slower "off rate" from the growth hormone receptor than wild type growth hormone. Variant B2024 thus has the following sequence:

H18A, Q22A, F25A, D26A, Q29A, E65A, K168A, E174A, G120K.

The G120K substitution was added to make a better antagonist candidate, although other substitutions at that site are acceptable. Any amino acid can be substituted at G120 to generate an antagonist; more preferably, the substitution is lysine, arginine, tryptophan, tyrosine, phenylalanine, or glutamate.

It is expected that B2024 could be further modified by restoring the glycine at residue 120, thereby generating a candidate for use as an agonist that is expected to have reduced antigenicity in humans. Similarly, such a candidate would be more optimally pegylated in comparison with 852d, as the number of lysine residues within the site I interface is decreased in comparison with the "supermutant".

EXAMPLE V

Production of the B2036 Variant

The B2036 variant was produced according to the following exemplary protocol.

Methods
(a) Expression Vector and Host Cells

Figure 10:
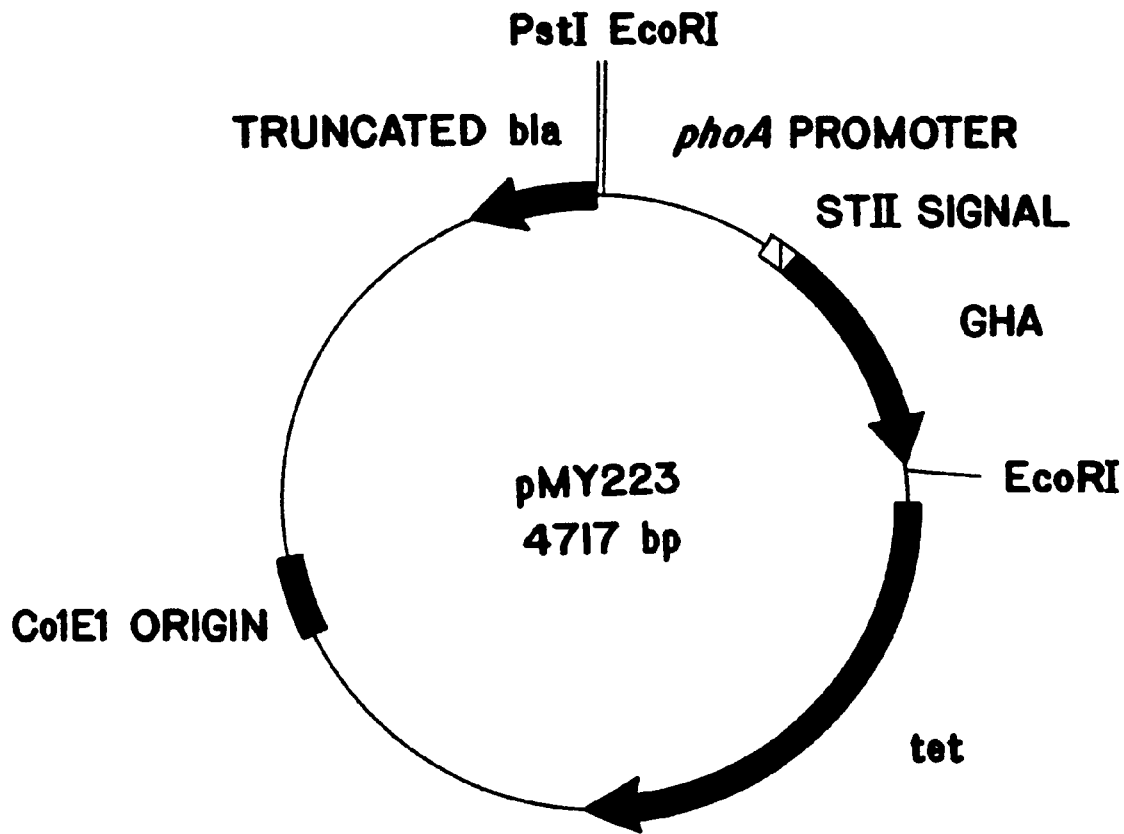
FIG. 10 shows a plasmid map for an exemplary vector used to express an antagonist hGH variant of the present invention (the B2036 variant), as described in Example V.

The vector used for expression of the B2036 variant in *E. Coli* was pMY233 (FIG. 10). Plasmid pMY223 is based on the well-characterized plasmid pBR322 and is similar to the hGH production plasmid pHGH4R (Chang, et al., *Gene*, 55:189–196 [1987]), except that the B2036 coding sequence replaces the hGH coding sequence. pMY223 encodes resistance to tetracycline antibiotics, but unlike pBR322 is sensitive to β-lactam antibiotics (penicillin, ampicillin, etc).

The amino acid differences between the B2036 variant encoded by pMY223 and the wild-type human growth hormone sequence are shown in Table 10, along with the codons at these sites.

TABLE 10

Sequence differences between the B2036 variant encoded by pMY223 and wild-type hGH

| Wild-type amino acid | Amino acid # | B2036 amino acid | B2036 codon |
|---|---|---|---|
| His | 18 | Asp | GAC |
| His | 21 | Asn | AAC |
| Gly | 120 | Lys | AAG |
| Arg | 167 | Asn | AAC |
| Lys | 168 | Ala | GCG |
| Asp | 171 | Ser | AGC |
| Lys | 172 | Arg | AGG |
| Glu | 174 | Ser | AGC |
| Ile | 179 | Thr | ACC |

The B2036 variant is expressed from a 1106-bp expression cassette cloned into a PstI-EcoRI restriction site. The expression cassette contains a single copy of the B2036 variant coding sequence fused in frame to the 23-residue heat stable enterotoxin (STII) signal peptide (Picken, et al., *Infection and Immunity*, 42:269–275 [1986]). Transcription of B2036 variant is directed by the *E. coli* phoA promoter (Chang et al., *Gene*, 44:121–125 [1986]). A translation initiation site is provided by the STII Shine-Dalgarno sequence. Translation begins with the STII signal peptide, which directs translocation of the B2036 variant across the cytoplasmic membrane into the periplasmic space. The STII signal peptide is then removed by *E. coli* leader peptidase. The mature protein folds into its correct conformation in the periplasm and both disulfide bonds are formed.

Plasmid pMY223 was constructed by a three-way ligation of fragments from plasmids pB2036 and pHGH4R. More specifically, a 565 base pair (bp) NsiI-PvuII fragment of pB2036 containing the B2036 variant coding sequence was ligated to the NsiI-BamHI backbone and the 405 bp PvuII-BamHI fragment of pHGH4R.

Plasmid pB2036 was derived from plasmid pS0643, also known as phGHam-g3 (the construction of which is described in Lowman et al., *Biochemistry*, 30:10832–10838 [1991]), which was the starting plasmid employed in the phage display studies described in Example II. pB2036 differs from pSO643 in that the B2036 coding sequence replaces the hGH coding sequence.

The host cell for expression of the B2036 variant was *E. coli* 33B6, which is a derivative of *E. coli* W3110 (see *Escherichia coli* and *Salmonella typhimurium*: Cellular and Molecular Biology, 2:1190–1219 [Washington, D.C.: American Society for Microbiology, 1987]). The complete genotype of 33B6 is ΔfhuA phoAΔE15 Δ(argF-lac)169 deoC2 degP41(ΔPstI-Kan$^r$) IN(rrnD-rrnE)1 ilvG2096 (Val$^R$). The derivation of 33B6 is described below.

The starting strain, *E. coli* W3110, is a derivative of *E. coli* K-12 that is F$^-$ and lambda-resistant. It has been shown to carry an inversion of the chromosome between rrnD and rrnE.

The fhuA gene (previously designated tonA) was deleted from W3110 by imprecise excision of Tn10 following its insertion into the fhuA gene. The resulting strain, 1A2, is resistant to bacteriophages T1, T5, and ø80.

Two deletion mutations, phoAΔE15 and Δ(argF-lac)169, were simultaneously introduced into 1A2 by P1 cotransduction with a linked Tn5 insertion in the proC gene. Precision excision of the transposon restored the proc gene. The phoAΔE15 mutation eliminates alkaline phosphatase expression, and the Δ(argF-lac)169 mutation is responsible for the Lac- phenotype of this strain, 7C1.

The deoC2 mutation, which eliminated deoxyribose phosphate aldolase expression, was introduced by P1 cotransduction. The deoc locus is genetically linked to the threonine biosynthetic locus. A threonine auxotroph was created by Tn10 insertion and imprecise excision. The threonine auxotroph was then transduced to threonine prototrophy with P1 phage grown on a deoC2 mutant. Presence of the deoC2 mutation was confirmed by the inability of the resulting strain, 16C9, to grow on 0.2% thymidine as a carbon source.

The degP41(ΔPstI-Kan$^r$), a mutation in the gene for a periplasmic protease, was introduced by transduction. This mutation was constructed in vitro by replacing a section of the degP gene with a kanamycin resistance gene. This is not a transposon, but allows for selection of the deletion using kanamycin resistance. The resulting strain is 23E3.

The ilvG2096 (Val$^r$) mutation was introduced by homogenotization. This mutation repairs a frameshift that causes the wild-type K-12 to be sensitive to valine. Strain 23E3 was transformed with plasmid pAH29, containing the ilvG2096 (Val$^r$) marker and an ampicillin resistance gene. Strain 33B6, which had spontaneously lost the plasmid and which had acquired the ilvG2096(Val$^r$) locus, was identified by screening ampicillin sensitive clones for valine resistance. The important characteristics of the final strain, 33B6, are that it is resistant to l1 phage, it does not overproduce alkaline phosphatase when phosphate is depleted (which is the condition used to induce product synthesis), it lacks a protease, and it is not susceptible to valine toxicity.

(b) Fermentation

A slurry of 33B6 cells containing the pMY223 vector (hereinafter "33B6/pMY223 cells") for expressing the B2036 variant was produced as follows.

An amino acid feed for 1000-L fermentation was prepared by aseptically mixing the following components:

3.2 kg Yeast extract;

24 kg HY-CASE AMINO (Quest, Int'l, Hoffman Estates, Ill.);

50 g Methionine;

Deionized water to 135 L.

The following components were transferred to a 1000-L fermentor capable of delivering 3–5 mM $O_2$/L-min:

1.0 L FERMAX ADJUVANT 27 antifoam agent (OSI Specialties Group, Witco Corp., South Charleston, W.V.);

1820.0 g Sodium phosphate dibasic;

910.0 g Sodium phosphate monobasic dihydrate;

3500.0 g Ammonium sulfate;

700.0 g Sodium citrate dihydrate;

1050.0 g Potassium chloride;

700.0 L Deionized water.

The fermentor was sterilized at 121° C. for 30 minutes. After cooling, the following were aseptically transferred into the sterilized fermentor:

50 kg of the amino acid feed described above;

7.7 L 1 M Magnesium sulfate;

350 ml 2.7% Ferric chloride;

350 ml Trace element solution;

2 L 5 mg/ml Tetracycline alcohol;

1 L 50% Glucose.

The fermentor was run at 37° C. and pH was maintained at approximately pH 7.3 (i.e., between 7.0 and 7.5) with sufficient aeration and agitation to provide between 3 and 5 mM $O_2$/L-min.

33B6/pMY223 cells were aseptically transferred to the fermentor as an 8-L inoculum with an optical density (OD) at 600 nm of 15. The fermentor was run, feeding sufficient glucose to meet the culture's demand (but avoiding glucose accumulation in the fermentor) and maintaining the dissolved oxygen at 30% or more of air saturation. pH was controlled using 15 N ammonium hydroxide or 24% sulfuric acid, and FERMAX ADJUVANT 27 was used to control foaming. When the culture reached an OD at 600 nm of 20, the amino acid feed was begun at about 0.06 kg/minute.

At approximately 32 hours after inoculation, the culture was inactivated by heat killing at 60° C. for 30 seconds. A cell slurry was then harvested by centrifugation and frozen in granules.

(c) Cell Extraction and Clarification

Frozen granules from the fermentation harvest (hereinafter the "cell pellet") were stored at −60° C. or below prior to use. 5 L extract buffer (6 M urea, 0.02 M Tris, pH 7.65, at room temperature) per kg cell pellet was added to a jacketed extraction tank. The cell pellet was slowly added to the extract buffer, with stirring. Foaming was minimized. The suspension was mixed at 4° C. until all of the pellet was in solution. The pH was adjusted to 8.0 and the solution was mixed at 4° C. for two hours to form an extract. 3 L water per liter of extract and 10 ml 5% polyethylene imine (PEI), pH 8.0, per liter of extract were added, with stirring.

The extract was clarified by passage through an Alfa Laval AX213 continuous flow centrifuge. The extract was continuously agitated to maintain the suspension and was fed at a rate of approximately 20 liters per minute (LPM) into the centrifuge. The supernatant was collected in a jacketed receiving tank, set to maintain the temperature at 4° C. When the entire extract had been fed through the centrifuge, approximately 75 L of purified water (4° C.), was fed through she centrifuge to recover the clarified *E. coli* extract from the centrifuge.

(d) Anion Exchange Chromatography I

The clarified *E. coli* extract was purified on a column of DEAE TRISACRYL LS PLUS (volume=0.36 L/kg cell paste), run at 4° C. Before loading, the column was washed and equilibrated with equilibration buffer (0.05 M Tris-HCl, pH 8.0, 4° C.). The column was then loaded with the clarified *E. coli* extract and washed with at least three column volumes of equilibration buffer until the UV absorbance of the eluent was at or near baseline. The column was eluted with elution buffer (3 M urea, plus MES, MOPS, Tris-HCl, TEA-HCl, glycine and glycylglycine, each at 18 mM, pH 5.0). Column loading, washing, and elution were carried out at a nominal flow rate for all chromatography steps in this example. Fractions of the UV-absorbing eluent were collected and analyzed by SDS-PAGE. Those fractions containing the B2036 variant were pooled.

(e) Anion Exchange Chromatography II

The DEAE TRISACRYL LS PLUS pool was pH-adjusted and purified on a column of DEAE SEPHAROSE FAST FLOW (volume=1.47 L/kg cell paste). The pH of the DEAE TRISACRYL LS PLUS pool was adjusted to about 7.2 with 2% sodium hydroxide at 4° C. The column was washed and equilibrated with equilibration buffer (0.05 M Tris HCl, pH 8.0, 4° C.). The column was then loaded with the pH-adjusted pool and washed with at least three column volumes of equilibration buffer until the UV absorbance of the eluent was at or near baseline. The column was eluted with elution buffer (3 M urea, plus MES, MOPS, Tris-HCl, TEA-HCl, glycine and glycylglycine, each at 18 mM, pH 5.0), and fractions of the UV-absorbing eluent were collected and analyzed by SDS-PAGE. Those fractions containing the B2036 variant were pooled.

(f) Q SEPHAROSE FAST FLOW Chromatography

The DEAE SEPHAROSE FAST FLOW pool was pH-adjusted and further purified on a Q SEPHAROSE FAST FLOW column (volume=0.43 L/kg cell paste), run at 4° C. The pH of the DEAE SEPHAROSE FAST FLOW pool was adjusted to 7.2 with 2% sodium hydroxide at 4° C. The column was equilibrated with equilibration buffer (0.05 M Tris, pH 8.0) and loaded with the pH-adjusted pool. The column was washed with one column volume of equilibration buffer and eluted with a linear gradient starting at 0.05 M NaCl, 0.05 M Tris, pH 8.0 and ending with 0.20 M NaCl, 0.05 M Tris, pH 8.0, using three column volumes of each buffer. Fractions were collected and analyzed by SDS-PAGE, and those fractions containing B2036 variant were pooled.

(g) PHENYL TOYOPEARL 650M Chromatography

After conditioning, the Q SEPHAROSE FAST FLOW pool was further purified on a PHENYL TOYOPEARL 650M column (volume=0.50 L/kg cell paste), run at room temperature. The Q SEPHAROSE FAST FLOW pool was conditioned with conditioning buffer (1.2 M sodium sulfate, 0.05 M Tris, pH 7.2) by adding a volume of conditioning buffer equivalent to 1.5 times the volume of the Q SEPHAROSE pool and stirring the resultant solution for about 15 minutes. The solution was then brought to room temperature. The column was equilibrated with three column volumes of equilibration buffer (0.75 M sodium sulfate, 0.05 M Tris, pH 7.2) through a 0.22$\mu$ inlet filter. The entire conditioned pool was then loaded onto the column through a 0.3$\mu$ Pall Profile inlet filter. The column was eluted with a linear gradient starting with 0.75 M sodium sulfate, 50 mM Tris, pH 7.2 and ending with 50 mM Tris, pH 7.5. Three column volumes of each buffer were used. Fractions were collected and analyzed by SDS-PAGE, and those fractions containing the B2036 variant were pooled.

(h) SEPHADEX G-25 Chromatography

A SEPHADEX G-25 column was used to reduce the salt in the PHENYL TOYOPEARL pool by exchanging the B2036 variant into 0.05 M Tris buffer. The column was run at 4° C. The volume of the load was restricted to a maximum of 30% of the total bed volume of the column. The column was equilibrated with three column volumes of equilibration buffer (0.05 M Tris, pH 7.2) and then loaded with the PHENYL TOYOPEARL pool. The column was eluted with 0.05 M Tris, pH 7.2. When the OD at 280 nm began to increase, the pool was collected until the OD 280 fell to near baseline.

(i) DEAE SEPHAROSE FAST FLOW Chromatography

The SEPHADEX G-25 pool was further purified on a DEAE SEPHAROSE FAST FLOW column (volume=0.04 L/g protein), run at 4° C. The column was equilibrated with a minimum three column volumes of equilibration buffer (0.05 M Tris, pH 8.0). The column was then loaded with the SEPHADEX G-25 pool. The load limit for the column was 25 g protein per liter of resin. The column was eluted with approximately ten column volumes of elution buffer (2 M urea plus MES, MOPS, Tris-HCl, TEA-HCl, glycine, and glycylglycine, each at 17 mM, pH 5.0). When the OD at 280 nm of the eluent reached a value of 0.1, fractions were collected until the OD 280 fell below a value of 0.5. The fractions were analyzed by SDS-PAGE, and fractions containing the B2036 variant were pooled.

(j) Concentration by Q SEPHAROSE FAST FLOW Chromatography

The DEAE SEPHAROSE FAST FLOW pool was concentrated on a Q SEPHAROSE FAST FLOW column (volume=0.07 L/g of protein), run at 4° C. The column was equilibrated with at least four column volumes of 0.1 M HEPES, pH 7.7. The entire DEAE SEPHAROSE FAST FLOW pool was loaded onto the column, and the column was washed with at least four column volumes of buffer. The column was eluted with approximately two column volumes of elution buffer (0.1 M HEPES, 0.22 M NaCl, pH 7.7). When the OD at 280 nm of the eluent exceeded 2.0, the pool was collected until the OD 280 fell below 2.0.

Results

The B2036 variant was essentially free of host cell impurities and any known significant degraded forms of the variant as determined by SDS-PAGE using Coomassie blue stain.

EXAMPLE VI

Production of the B2024 Variant

The B2024 variant was produced according to the following exemplary protocol.

Methods (a) Expression Vector and Host Cells

The B2024 variant was expressed in *E. coli* 33B6 using plasmid pMY216, which is the same as pMY223 (described in Example V), except that pMY216 contains the B2024 coding sequence instead of the B2036 coding sequence.

(b) Fermentation

A slurry of 33B6 cells containing the pMY223 vector (hereinafter "33B6/pMY216 cells") for expressing the B2024 variant was produced as follows.

The following components were transferred to a 60-L fermentor capable of delivering 3–6 MM $O_2$/L-min:

60.0 ml FERMAX ADJUVANT 27 antifoam agent (OSI Specialties Group, Witco Corp., South Charleston, W.V.);

156.0 g Sodium phosphate dibasic;

78.0 g Sodium phosphate monobasic dihydrate;

300.0 g Ammonium sulfate;

60.0 g Sodium citrate dihydrate;

90.0 g Potassium chloride;

36.0 L Deionized water.

The fermentor was sterilized at 121° C. for 30 minutes. After cooling, the following were aseptically transferred into the sterilized fermentor:

600.0 ml 1 M Magnesium sulfate;

60.0 ml 2.7% Ferric chloride;

60.0 ml Trace element solution;

120.0 ml 5 mg/ml Tetracycline alcohol;

90 ml 50 Glucose;

6.0 L 10% NZ Amine A (Quest, Int'l, Hoffman Estates, Ill.);

Deionized water to 48 L.

The fermentor was run at 37° C. and pH was maintained at approximately pH 7.0 (i.e., between 6.8 and 7.2) with sufficient aeration and agitation to provide between 3 and 6 mM $O_2$/L-min.

33B6/pMY216 cells were aseptically transferred to the fermentor as an 1-L inoculum with an optical density (OD) at 600 nm of 4. The fermentor was run, maintaining the dissolved oxygen at 0% of air saturation for as long as possible and feeding sufficient glucose to meet the culture's demand, but avoiding glucose accumulation in the fermentor. Glucose was fed so that any acetate formed was reconsumed in a short time (usually less than a half hour, but not more than two hours). pH was controlled using 12 N ammonium hydroxide containing 47 g/L L-leucine or 24% sulfuric acid, and FERMAX ADJUVANT 27 was used to control foaming.

At approximately 40 hours after inoculation, the culture was inactivated by heat killing at 60° C. for 30 seconds. A cell paste was then harvested by centrifugation and frozen.

(c) Cell Extraction and Clarification

Frozen cell paste from the fermentation harvest was stored at −60° C. or below prior to use. The cell paste was thawed overnight at 4° C. 5 L extract buffer (6 M urea, 0.02 M Tris, pH 8.5, at 4° C.) per kg cell paste was added to the cell paste. The cells were homogenized in the buffer using an ULTRATURREX homogenizer (Tekmar, Cincinnati, Ohio) with stirring, minimizing foaming. The temperature was maintained at 4° C., and the suspension was mixed until all of the cells were in suspension. The pH was adjusted to approximately 8.1. The solution was mixed at 4° C. for two hours to form an extract. 1 L water per liter of extract and 20 ml 5% PEI, pH 8.0, per liter of extract were added, with stirring.

The extract was clarified by passage through an Alfa Laval BTPX205 continuous flow centrifuge. The extract was continuously agitated to maintain the suspension and was fed at a rate of approximately 2 LPM into the centrifuge. The supernatant was collected in a receiving tank at 4° C. When the entire extract had been fed through the centrifuge, approximately 5–10 L of purified water (4° C.), was fed through the centrifuge to displace the clarified *E. coli* extract from the centrifuge. The clarified extract was diluted with purified water (4° C.) until the conductivity measured less than 2.0 mS.

(d) Anion Exchange Chromatography

The clarified *E. coli* extract was purified on a column of DEAE TRISACRYL LS PLUS (volume=0.50 L/kg cell paste) in series with a DEAE SEPHAROSE FAST FLOW column (volume=2.6 L/Kg cell paste), both run at 4° C. Before loading, the columns were washed and equilibrated with equilibration buffer (0.02 M Tris-HCl, pH 8.5, 4° C.). The DEAE TRISACRYL LS PLUS column was then loaded with the clarified *E. coli* extract. The columns were washed with at least three column volumes of equilibration buffer until the UV absorbance of the eluent was at or near baseline. The DEAE TRISACRYL LS PLUS column was then disconnected from the DEAE SEPHAROSE FAST FLOW column. The B2024 variant was eluted from the DEAE SEPHAROSE FAST FLOW column with a pH gradient elution buffer (3 M urea, plus MES, MOPS, Tris-HCl, TEA-HCl, glycine, and glycylglycine, each at 10 mM, pH 5.0). Column loading, washing, and elution were carried out at a nominal flow rate for all chromatography steps in this example. Fractions containing the B2024 variant were pooled, based on the optical absorbance of the elution and SDS-PAGE analysis of the fractions.

(e) Q SEPHAROSE FAST FLOW Chromatography

The DEAE SEPHAROSE FAST FLOW pool was pH-adjusted and further purified on a Q SEPHAROSE FAST FLOW column (volume=0.67 L/kg cell paste), run at 4° C. The pH of the DEAE SEPHAROSE FAST FLOW pool was adjusted to pH 8.5 with 2% sodium hydroxide at 4° C. The column was equilibrated with equilibration buffer (0.02 M Tris, pH 8.5), loaded with the pH-adjusted pool, and was eluted with a linear gradient starting at 0.02 M Tris, pH 8.5 and ending with 0.10 M NaCl, 0.08 M MES, pH 6.5, using 2.5 column volumes of each buffer. Fractions were collected and analyzed by SDS-PAGE, and those fractions containing B2024 variant were pooled.

(f) PHENYL TOYOPEARL 650M Chromatography

After conditioning, the Q SEPHAROSE FAST FLOW pool was further purified on a PHENYL TOYOPEARL 650M column (volume=0.20 L/kg cell paste), run at room temperature. The Q SEPHAROSE FAST FLOW pool was conditioned with conditioning buffer (2 M ammonium sulfate, 0.04 M Tris, pH 7.2) by adding a volume of conditioning buffer equivalent to the volume of the Q SEPHAROSE pool and stirring the resultant solution until uniform. The solution was then brought to room temperature. The column was equilibrated with two to three column volumes of equilibration buffer (1.0 M ammonium sulfate, 0.02 M Tris, pH 7.2). The entire conditioned pool was then loaded onto the column, and the column was eluted with a linear gradient starting with 1 M ammonium sulfate, 20 mM Tris, pH 7.2 and ending with purified water. Four column volumes of each buffer were used. Fractions were collected and analyzed by SDS-PAGE, and those fractions containing the B2024 variant were pooled.

(g) SEPHADEX G-25 Chromatography

A SEPHADEX G-25 column was used to reduce the salt in the PHENYL TOYOPEARL pool by exchanging the B2024 variant into 0.02 M Tris buffer. The column was run at 4° C. The volume of the load was restricted to a maximum of 30% of the total bed volume of the column. The column was equilibrated with three column volumes of equilibration buffer (0.02 M Tris; pH 8.0) and then loaded with the PHENYL TOYOPEARL pool. The column was eluted with 0.02 M Tris, pH 8.0. When the OD at 280 nm increased to approximately 0.2, the pool was collected until the OD 280 fell below 0.2.

(h) DEAE SEPHAROSE FAST FLOW Chromatography

The SEPHADEX G-25 pool was further purified on a DEAE SEPHAROSE FAST FLOW column (volume=0.04 L/g protein), run at 4° C. The column was equilibrated with a minimum three column volumes of equilibration buffer (0.02 M Tris, pH 8.0). The G-2 pool was diluted with an equal volume of water for irrigation, and the resulting solution was mixed until uniform and then loaded onto the column. The column was eluted with approximately ten column volumes of elution buffer (2 M urea plus MES, MOPS, Tris-HCl, TEA-HCl, glycine, and glycylglycine, each at 10 mM, pH 5.0). When the OD at 280 nm of the eluent reached a value of 0.1, fractions were collected until the OD 280 fell below a value of 0.5. The fractions were analyzed by SDS-PAGE, and fractions containing the B2024 variant were pooled.

(i) Concentration by DEAE SEPHAROSE FAST FLOW Chromatography

The DEAE SEPHAROSE FAST FLOW pool was concentrated on a DEAE SEPHAROSE FAST FLOW column (volume=0.06 L/g protein) run at 4° C. The column was equilibrated with at least four column volumes of 0.02 M Tris, pH 8.0. The entire DEAE SEPHAROSE FAST FLOW pool was loaded onto the column, and the column was washed with at least two column volumes of 0.02 M MES buffer, pH 6.5. The column was eluted at with approximately two column volumes of 0.1 M NaCl, 0.02 M MES, pH 6.5, followed by two column volumes of 0.15 M NaCl, 0.02 M MES, pH 6.5. When the OD at 280 nm of the eluent exceeded 2.0, the pool was collected until the OD 280 fell below 2.0.

Results

The B2024 variant was essentially free of host cell impurities and any known significant degraded forms of the variant as determined by SDS-PAGE using Coomassie blue stain.

EXAMPLE VII

Pegylation of the B2036 Variant With PEG(5000)

M-SPA-PEG(5000) was used to pegylate the B2036 hGH variant. Pegylation of the B2036 variant was carried out according to the following protocol, which is also suitable for pegylation of wild-type hGH and other hGH variants, such as the B2024 variant.

Methods (a) Pegylation Reaction

Purified B2036 variant, produced as set forth in Example IV, was reacted with M-SPA-PEG(5000) (Shearwater Polymers, Inc., Huntsville, Ala.), which was added as a solid to the B2036 variant preparation. The reaction was allowed to proceed at room temperature with constant stirring. Briefly, the B2036 variant preparation was diluted with 0.1 M HEPES, pH 7.7, to a final protein concentration of 10 mg B2036 variant/ml and allowed to come to room temperature. The pH of the room temperature solution was about 7.5. Solid M-SPA-PEG(5000) was added to the preparation, with stirring, to a concentration of 20 g/L. The pH was maintained at 7.5±0.1. The reaction was complete within two hours after the addition of M-SPA-PEG(5000).

(b) Hydrophobic Interaction (PHENYL TOYOPEARL 650M) Chromatography

The pegylated B2036 variant preparation was conditioned and then purified on a PHENYL TOYOPEARL 650M column (volume=0.13 L/g B2036 variant), run at room temperature. The pegylated B2036 variant preparation was conditioned by adding a volume of citrate conditioning solution (0.8 M sodium citrate, 0.05 M Tris, pH 7.7) equivalent to the volume of the pegylated B2036 variant preparation and stirring the resultant solution for about 15 minutes at room temperature. The column was equilibrated at room temperature with at least one column volume of equilibration buffer (0.40 M sodium citrate, 0.05 M Tris, pH 7.5). The conditioned pegylated B2036 variant preparation was then loaded onto the column. The column was eluted with a four column volume linear gradient starting with 0.40 M sodium citrate, 50 mM Tris, pH 7.5, and ending with 50 mM Tris, pH 7.5. Column loading, washing, and elution were carried out at a nominal flow rate for all chromatography steps in this example. Fractions were collected and analyzed by SDS-PAGE, and those fractions containing the PEG-B2036 variant conjugate were pooled.

(c) Ultrafiltration/Diafiltration

The PHENYL TOYOPEARL pool was concentrated approximately three-fold and then diafiltered against six volumes of 0.025 M sodium acetate, pH 4.0, using an ultrafiltration system equipped with a 10 kD regenerated cellulose membrane (Millipore, Bedford, Mass.).

The first step of the concentration was a total recycle with the filtrate open mode using the PHENYL TOYOPEARL pool. The recycle was done for about 15 minutes, with the goal of reducing the concentration of PEG-B2036 variant in the filtrate to less than 3% of the feed concentration. The actual concentration of the PHENYL TOYOPEARL pool was initiated with the UF mode (i.e, with the retentate directed to a recycle tank, and the filtrate directed to drain) . A transition from the initial recycle to the UF mode was done automatically without a feed pump shutdown, and without any change in the feed rate or retentate pressure. The concentration was continued until a three-fold reduction in retentate volume was achieved. The concentrated PHENYL TOYOPEARL pool was diafiltered against six volumes of 0.025 M sodium acetate, pH 4.0, in the DF mode (i.e., with the retentate directed to the recycle tank, filtrate directed to drain, and buffer transferred into the recycle tank). A transition from the UF mode to the DF mode is done automatically without a feed pump shutdown.

After the Phenyl Toyopearl pool was diafiltered and concentrated, a low pressure drop ($\Delta P$) recycle was done in a total recycle with the filtrate closed mode. The retentate valve was fully open during this step. The feed rate was maintained to give a 5 PSI pressure drop. The recirculation was done for at least 10 minutes. The product transfer mode was then used to transfer the contents of the ultrafiltration system into a pool tank. The transfer was done in two steps. The first step involved draining the retentate in the recycle tank through a valve, with the membrane unit isolated. In the second step, the ultrafiltration set-up was completely emptied, using a low-pressure stream of inert gas to pusall the product out of the system and into the pool tank.

(d) Cation Exchange (S SEPHAROSE FAST FLOW) Chromatography

The pegylated B2036 variant was further purified by cation exchange chromatography on an S SEPHAROSE FAST FLOW column, loading no more than 7 g protein/L resin. The column was equilibrated at room temperature with at least three column volumes of 0.025 M sodium acetate, pH 4.0. The entire PEG-B2036 variant UF/DF pool was then loaded onto the column, and the column was eluted with a seven column volume linear gradient starting with 0.025 M sodium acetate, pH 4.0, and ending with 0.25 M NaCl, 0.025 M sodium acetate, pH 4.0. After the OD at 280 nm began to increase, fractions were collected and analyzed by SDS-PAGE and mass spectrometry. Those fractions containing PEG-hGH conjugates containing four to five PEG groups were pooled.

(e) Ultrafiltration/Diafiltration

The S SEPHAROSE FAST FLOW pool was concentrated to approximately 10 g/L using an ultrafiltration system equipped with a 10 kD regenerated cellulose membrane (Millipore, Bedford, Mass.). Concentration, low pressure drop recycle, and product transfer steps were performed as described in the "Ultrafiltration/Diafiltration" section above to achieve a seven-fold reduction in retentate volume.

(f) SEPHADEX G-25 Chromatography

A SEPHADEX G-25 column, run at 4° C., was used to exchange the PEG-B2036 variant preparation into formulation buffer (18.0 g/L mannitol, 0.68 g/L glycine, 5 mM sodium phosphate, pH 7.4). The volume of the load was restricted to 25% of the total bed volume of the column. The column was washed with one column volume of purified water for irrigation, followed by equilibration with at least 1.5 column volumes of formulation buffer. The entire PEG-B2036 variant UF pool was then loaded onto the column, and the column was eluted with formulation buffer. When the OD at 280 nm exceeded 0.5, fractions were collected until the OD 280 fell below approximately 0.5. The SEPHADEX G-25 pool was then diluted with formulation buffer to a concentration of 5.0 mg/ml.

Results

The stoichiometries of PEG per hGH variant were assessed by mass spectrometry on a VESTEC laser desorption ionization mass spectrometer (PerSeptive Biosystems, Inc., Framingham, Mass.). The results indicated that the preparation contained primarily conjugates containing four and five PEG groups (PEG-4/5-B2036).

EXAMPLE VIII

Pegylation of the B2036 Variant With PEG(20,000)

The B2036 variant was pegylated with PEG(20,000) according to the following exemplary protocol.

B2036 variant, purified as described in Example V, was buffer exchanged into 0.05 M sodium phosphate, pH 7.5, using a G-25 SEPHADEX PD-10 column (Pharmacia, Piscataway, N.J.). The B2036 variant solution was then diluted to a protein concentration of 10 mg/ml. 60 mg of M-SPA-PEG(20,000) (Shearwater Polymers, Inc. Huntsville, Ala.) was weighed out in a tube, and 6 ml of the B2036 variant solution was added. The reaction was incubated at room temperature for 75 minutes. The reaction mixture was buffer exchanged into 25 mM sodium acetate, pH 4.0, using a G-25 SEPHADEX PD 10 column.

The resultant PEG(20,000)-B2036 variant solution was applied to a SP SEPHAROSE HP column (Pharmacia) that had been washed with 25 mM sodium acetate, pH 4.0, until the column was equilibrated. The column was loaded with the PEG (20,000)-B2036 variant solution at a concentration of 4.1 mg/ml resin at room temperature.

The column was then eluted with a linear gradient consisting of 25 mM sodium acetate, pH 4.0, to 0.5 M sodium chloride in 25 mM sodium acetate, pH 4.0, using five column volumes of each buffer. Fractions were collected and analyzed by SDS gel electrophoresis, using 2–15% polyacrylamide prepoured Daiichi gels (Owl Scientific, Cambridge, Mass.). Fractions containing a PEG(20,000)-B2036 form having a single PEG(20,000) molecule conjugated to each B2036 molecule were pooled and concentrated by ultrafiltration using a CENTRIPREP 10 concentrator (Amicon, Inc., Beverly, Mass.). The CENTRIPREP 10 concentrator was centrifuged at 8,000 rpm in a SORVALL RT6000B centrifuge (Dupont Instruments, Newtown, Conn.) at 16° C. The retentate was removed and further concentrated using a CENTRICON 10 concentrator (Amicon, Inc). The concentrator was centrifuged at 6500 rpm in a SORVALL RC-5B centrifuge at 16° C.

The concentrated PEG(20,000)-B2036 variant was then buffer exchanged into formulation buffer (18.0 g/L mannitol, 0.68 g/L glycine, 5 mM sodium phosphate, pH 7.4) using a G-25 SEPHADEX PD-10 column at room temperature.

EXAMPLE IX

Pegylation of the B2036 Variant With Y-PEG

The B2036 variant was pegylated with a branched-chain PEG having two 10,000 D chains (PEG2(20,000)) according to the following exemplary protocol.

B2036 variant, purified as described in Example V, was buffer exchanged into 0.05 M sodium phosphate, pH 7.5, using a G-25 SEPHADEX PD-10 column (Pharmacia, Piscataway, N.J.). The B2036 solution was then diluted to a protein concentration of 10 mg/ml. 100 mg of NHS-PEG2 (20,000) (Shearwater Polymers, Inc.) was weighed out in a tube, and 4 ml of the B2036 solution was added. The reaction was incubated at room temperature for 90 minutes. The reaction mixture was buffer exchanged into 25 mM sodium acetate, pH 4.0, using a G-25 SEPHADEX PD 10 column.

The resultant PEG2(20,000)-B2036 variant solution was applied to a SP SEPHAROSE HP column (Pharmacia) that had been washed with 25 mM sodium acetate, pH 4.0, until the column was equilibrated. The column was loaded with the PEG (20,000)-B2036 variant solution at a concentration of 2.75 mg/ml resin at room temperature. The column was then eluted with a linear gradient consisting of 25 mM sodium acetate, pH 4.0, to 0.5 M sodium chloride in 25 mM sodium acetate, pH 4.0, using five column volumes of each buffer. Fractions were collected and analyzed by SDS gel electrophoresis, using 2–15% polyacrylamide prepoured Daiichi gels (Owl Scientific, Cambridge, Mass.). Fractions containing a PEG2(20,000)-B2036 form having a single PEG2(20,000) molecule conjugated to each B2036 molecule were pooled and concentrated by ultrafiltration using a CENTRICON 10 concentrator (Amicon, Inc., Beverly, Mass.). The concentrator was centrifuged at 6500 rpm in a SORVALL RC-5B centrifuge at 16° C. (Dupont Instruments, Newtown, Conn.).

The concentrated PEG2(20,000)-B2036 variant was buffer exchanged into formulation buffer (18.0 g/L mannitol, 0.68 g/L glycine, 5 mM sodium phosphate, pH 7.4) using a G-25 SEPHADEX PD-10 column at room temperature.

EXAMPLE X

Pegylation Sites in PEG-4/5-B2036

The sites of PEG modification of a PEG-4/5-B2036 variant preparation produced as described in Examples V and VII were analyzed by tryptic mapping. Purified PEG-4/5-B2036 variant samples (1 mg/ml in 1 M $CaCl_2$, 0.1 M sodium acetate, 10 mM Tris, pH 8.8) were incubated with bovine trypsin (Worthington Biochemical Corp., Freehold, N.J.) at a protein weight ratio of 1:40 (trypsin:PEG-4/5-B2036 variant) as described in Kohr, W. J. et al., *Anal. Biochem.*, 122:348–359 (1982). The trypsin was added at time 0 and again at four hours of digestion. After incubation for eight hours at 37° C., digestion was stopped by adding phosphoric acid to pH 2, and samples were stored at 4° C.

Digested samples (100 μg) were loaded onto a 15×0.46 cm C-18 column (5-μm bead, 100-Å pore size; NUCLEOSIL, Alltech Associates, Deerfield, Ill.) in 0.1% aqueous trifluoroacetic acid and eluted with a gradient from 0 to 60% acetonitrile over 120 minutes at a flow rate of 0.4 ml/min at 40° C. The elution of tryptic peptides was monitored by absorbance at 214 nm.

The conjugation of a PEG group to a tryptic peptide was detected by the reduction in size of the corresponding peak on a chromatogram, as compared to the chromatogram produced from a tryptic digestion of the non-pegylated protein. The results indicated that the order of reactivity of the primary amines (measured as percent modification of primary peptides), from most reactive to least reactive is:

F1>K145, K140, K38, K158>K120, K70.

K41 and K115 were determined to be unreactive, based on the failure to detect modified versions of the corresponding tryptic peptides. Residues 168 and 172 in the B2036 variant were not capable of reacting with PEG because the lysines at these positions were replaced with different amino acids. None of the most reactive residues are in Site 1. In fact, the three Site 1 lysines present in wild-type hGH (K41, K168, and K172) are unreactive (K41) or absent from B2036 (K168 and K172). Thus, pegylation of the B2036 variant does not directly block Site 1 binding.

EXAMPLE XI

Cell-Based Assay of Agonist Activity of Pegylated B2036

A PEG-4/5-B2036 variant preparation produced as described in Examples V and VII was tested for activity in the cell-based dimerization assay described in Fuh, G. et al., *Science*, 256:1677–1680 (1992) and Colosi, P. et al., *J. Biol. Chem.*, 268:12617–12629 (1993). To produce the cells employed in this assay, the full-length hGH receptor was stably transfected into a premyeloid cell line, FDC-P1 (Colosi, P. et al., *J. Biol. Chem.*, 268:12617–12629 [1993]), which can then be induced to proliferate in the presence of hGH. The cells were maintained in RPMI medium with 10% fetal bovine serum and 2–5 nM hGH. Cells were fasted for four hours in medium without hGH, and then incubated with increasing concentrations of hGH variant for 10 hours at 37° C. The cells were given a pulse of [*H]thymidine for four hours, lysed, and DNA synthesis analyzed by the amount of radioactively bound to nitrocellulose filters. Fuh, G. et al., *Science*, 256:1677–1680 (1992). Neither B2036 nor PEG-4/5-B2036 stimulated cell proliferation at any concentration ranging from 0.001 to 1.0 μg/ml hGH variant.

EXAMPLE XII

Cell-Based Assay of Antagonist Activity of Pegylated B2036

In a study designed to test antagonist activity, the non-pegylated B2036 variant and PEG-4/5-B2036 variant preparation, produced as described in Examples V and VII, were incubated with 11 ng/ml recombinant hGH and increasing concentrations of variant ($10^4$ cells/0.2 ml total assay volume). The concentration of variant required to block 50% of the recombinant hGH-stimulated cell proliferation, i.e., the half-maximal inhibitory concentration ($IC_{50}$), was calculated for both variants. The $IC_{50}$ for non-pegylated B2036 was 0.19 μg/ml, whereas the $IC_{50}$ for PEG-4/5-B2036 was 13.01 μg/ml.

In a separate experiment, the assay was repeated ($5 \times 10^3$ cells/0.15 ml total assay volume) to compare the antagonist activity of a PEG-4/5-B2036 variant preparation with that of PEG(20,000)-B2036 variant and PEG2(20,000)-B2036 variant. These pegylated variants were produced as described in Examples VII, VIII, and IX, respectively. The $IC_{50}$ for each pegylated variant is set forth in Table 11.

TABLE 11

| Variant | $IC_{50}$ (μg/ml) |
| --- | --- |
| PEG-4/5-B2036 | 15.25 |
| PEG(20,000)-B2036 | 0.25 |
| PEG2(20,000)-B2036 | 1.74 |

EXAMPLE XIII

In Vivo Antagonist Activity of hGH Variants

The effect of daily injections of antagonist hGH variants on IGF-I levels was studied in Rhesus monkeys. The hGH variants tested were a variant containing a G120K substitution and the B2036 and B2024 variants. In addition, pegylated forms of these variants, having four to five molecules of PEG(5000), were tested. Daily doses of 0.25 mg/kg hGH variant preparation, formulated in 18.0 g/L mannitol, 0.68 g/L glycine, 5 mM sodium phosphate, pH 7.4, were injected subcutaneously into two adolescent male Rhesus monkeys per treatment group. IGF-1 levels were determined by immunoassay, as described in *Amer. J. Primatology*, 11:53–62 (1986).

Figure 11:
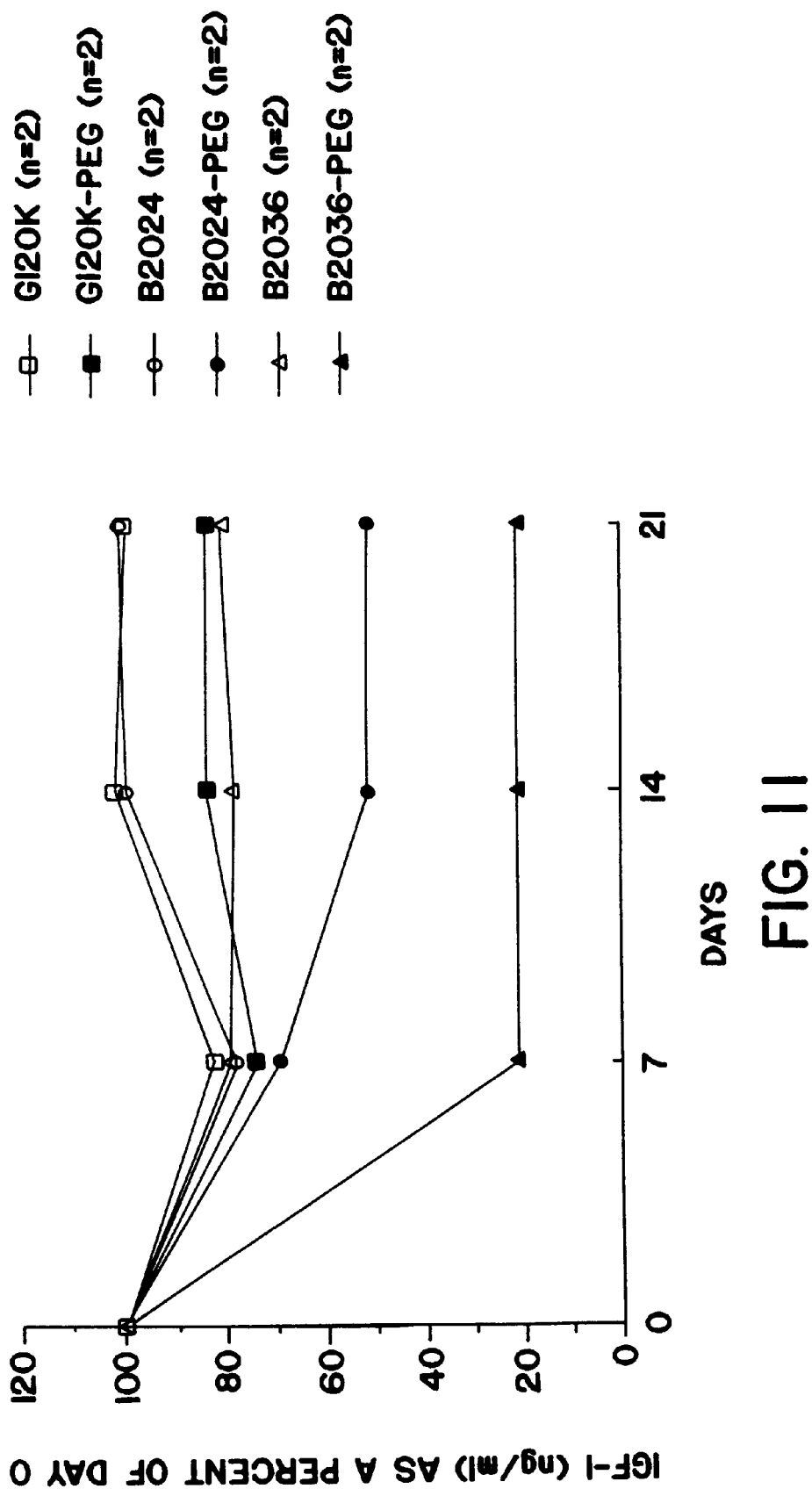
FIG. 11 shows the effect of daily subcutaneous injections (0.25 mg/kg) of various antagonist hGH variants of the present invention on insulin-like growth factor-I (IGF-I) levels in Rhesus monkeys. Both pegylated and non-pegylated forms of the variants were tested. See Example XIII.

The results are shown in FIG. 11. Decreases in IGF-I levels were observed at seven days after administration for all monkeys treated with an hGH variant, with the most significant decrease observed in monkeys treated with PEG-4/5-B2036. By 14 days, IGF-I levels had returned to pretreatment levels in monkeys treated with the G120K variant and the B2024 variant. Reduced IGF-I levels were observed in monkeys treated with the pegylated forms of the G120K and B2024 variants and with the non-pegylated B2036 variant. The 14-day IGF-1 levels for monkeys treated with PEG-4/5-B2036 variant preparation were the same as on day seven. 21-day IGF-I levels were approximately the same as seven-day IGF-I levels for all treatment groups.

EXAMPLE XIV

In Vivo Antagonist Activity of PEG-4/5-B2036 Variant Preparation

Single-Dose Pharmacodynamics

The effect of a single injection of a PEG-4/5-B2036 variant preparation on IGF-I levels was studied in Rhesus monkeys. A single dose of 1 mg/kg PEG-4/5-B2036 variant preparation, produced as described in Examples V and VII and formulated in 18.0 g/L mannitol, 0.68 g/L glycine, 5 mM sodium phosphate, pH 7.4, was injected either intravenously or subcutaneously into adolescent male Rhesus monkeys. The placebo was 0.5 ml formulation buffer administered subcutaneously. IGF-1 levels were determined as in Example XIII.

Figure 12:
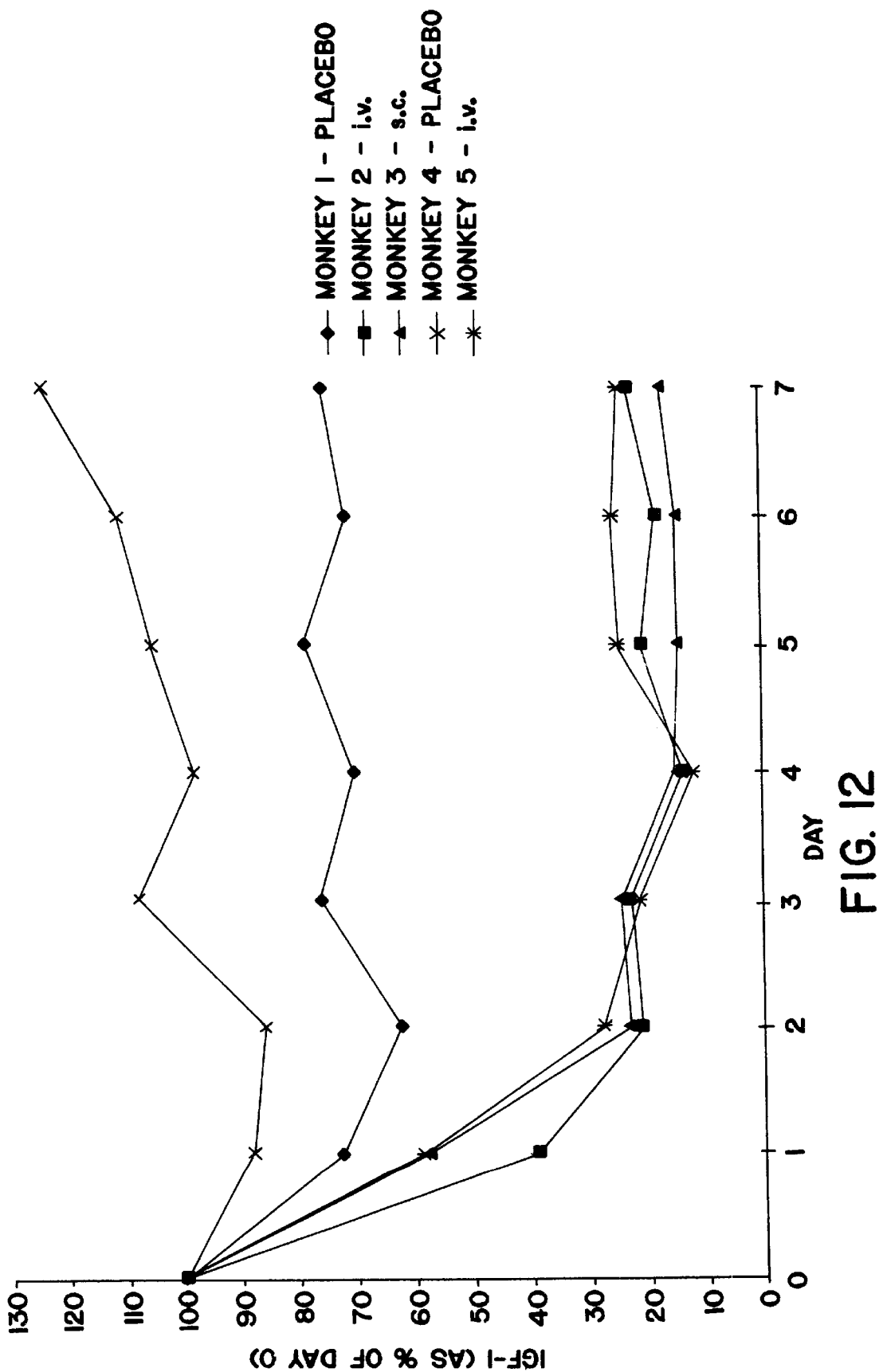
FIG. 12 shows the single-dose pharmacodynamics of a pegylated antagonist hGH variant (B2036) preparation injected intravenously or subcutaneously into Rhesus monkeys. Antagonist effect was measured as percent reduction in IGF-I level. See Example XIV.

The results are shown in FIG. 12. Regardless of route of administration, the IGF-I levels of all monkeys treated with the PEG-4/5-B2036 variant preparation were reduced at one day after administration, continued to decrease until four days after administration, and remained low throughout the seven-day study.

What is claimed is:

1. A method for inhibiting growth hormone action in a patient comprising administering to the patient an effective amount of a human growth hormone variant comprising the following set of amino acid substitutions:
H18A, Q22A, F25A, D26A, Q29A, E65A, K168A, E174A, and further comprising a substitution at G120.

2. The method of claim 1, wherein the patient has acromegaly.

3. The method of claim 1, wherein the patient has a tumor comprising tumor cells expressing receptors that bind human growth hormone.

4. The method of claim 1, wherein the patient has diabetic retinopathy.

5. The method of claim 1 wherein the human growth hormone variant is conjugated to one or more chemical groups that increase the actual molecular weight of the human growth hormone variant to between about 40 and about 100 kilodaltons.

6. The method of claim 5 wherein said chemical group is poly(ethylene glycol).

7. The method of claim 6 where the human growth hormone variant is conjugated to between about four and about six molecules of poly(ethylene glycol).

8. The method of claim 1 wherein the substitution at G120 is selected from G120R, G120K, G120W, G120Y, G120F, and G120E.

9. The method of claim 8 wherein the substitution at G120 is G120K.

10. The method of claim 9 wherein the human growth hormone variant is conjugated to one or more chemical groups that increase the actual molecular weight of the human growth hormone variant to between about 40 and about 100 kilodaltons.

11. The method of claim 10 wherein said chemical group is poly(ethylene glycol).

12. The method of claim 11 where the human growth hormone variant is conjugated to between about four and about six molecules of polyethylene glycol.

* * * * *